US012808086B2

(12) United States Patent

Suga et al.

(10) Patent No.: US 12,808,086 B2

(45) Date of Patent: Nov. 24, 2026

(54) LIBRARY CONSTRUCTION METHOD, CYCLIC PEPTIDE, FXIIA BINDER AND IFNGR1 BINDER

(71) Applicant: The University of Tokyo, Tokyo (JP)

(72) Inventors: Hiroaki Suga, Tokyo (JP); Takayuki Katoh, Tokyo (JP)

(73) Assignee: The University of Tokyo, Tokyo (JP)

(*) Notice: Subject to any disclaimer, the term of this patent is extended or adjusted under 35 U.S.C. 154(b) by 1186 days.

(21) Appl. No.: 17/788,990

(22) PCT Filed: Dec. 25, 2020

(86) PCT No.: PCT/JP2020/048981

§ 371 (c)(1),
(2) Date: Jun. 24, 2022

(87) PCT Pub. No.: WO2021/132661

PCT Pub. Date: Jul. 1, 2021

(65) Prior Publication Data

US 2023/0117920 A1 Apr. 20, 2023

(30) Foreign Application Priority Data

Dec. 27, 2019 (JP) ................................ 2019-239426
Aug. 6, 2020 (JP) ................................ 2020-134234

(51) Int. Cl.
*C40B 50/06* (2006.01)
*C12N 15/10* (2006.01)

(52) U.S. Cl.
CPC .......... *C40B 50/06* (2013.01); *C12N 15/1072* (2013.01)

(58) Field of Classification Search
None
See application file for complete search history.

(56) References Cited

U.S. PATENT DOCUMENTS

| | | | |
|---|---|---|---|
| 2018/0118786 | A1 | 5/2018 | Heinis |
| 2019/0077805 | A1 | 3/2019 | Vazquez |

(Continued)

FOREIGN PATENT DOCUMENTS

| | | |
|---|---|---|
| EP | 3040417 | 7/2016 |
| JP | 2011523634 | 8/2011 |

(Continued)

OTHER PUBLICATIONS

European Search Report and Written Opinion received in EP20906717 mailed Apr. 19, 2024.

(Continued)

*Primary Examiner* — Christian C Boesen

(74) *Attorney, Agent, or Firm* — Suzannah K. Sundby, Esq.; Canady + Lortz LLP

(57) ABSTRACT

The purpose of the present invention is to provide a method of producing a library including two or more cyclic peptides, wherein at least one of the cyclic peptides included in the library has a structure composed of 4 to 30 amino acids or derivatives thereof and contains, in the structure, at least one selected from cyclic β-, γ-, and δ-amino acids (cAAs), including a step of preparing an mRNA library encoding a peptide having a sequence represented by the formula (1); $-(Xaa)_{n1}-$ [in the formula (1), Xaas are each an arbitrary amino acid or derivative thereof, at least one Xaa is one selected from cyclic β-, γ-, and δ-amino acids (cAAs) and n1 is an integer of 2 to 28] and a step of using the mRNA library to express the peptide in a cell-free translation system and produce a library.

13 Claims, 16 Drawing Sheets

Specification includes a Sequence Listing.

(56) References Cited

U.S. PATENT DOCUMENTS

| | | | |
|---|---|---|---|
| 2020/0040372 | A1 | 2/2020 | Tanaka |
| 2020/0308572 | A1 | 10/2020 | Suga |

FOREIGN PATENT DOCUMENTS

| | | |
|---|---|---|
| JP | 2019503340 | 2/2019 |
| WO | 2018085921 | 5/2018 |
| WO | 2018128828 | 7/2018 |
| WO | 2018143145 | 8/2018 |
| WO | 2019077887 | 4/2019 |

OTHER PUBLICATIONS

Katoh & Suga, Ribosomal Incorporation of Consecutive Beta-Amino Acids, Sep. 26, 2018, pp. 12159-12167, vol. 140, No. 38, Publisher: J Am Chem Soc.

Kiss et al., Highly functionalized cyclic—amino acid moieties as promising scaffolds in peptide research and drug design, Sep. 1, 2017, pp. 1441-1455, vol. 49, No. 9, Publisher: Amino Acids.

Maini et al., Incorporation of—amino acids into dihydrofolate reductase by ribosomes having modifications in the peptidyltransferase center, Mar. 1, 2013, pp. 1088-1096, vol. 21, No. 5, Publisher: Bioorganic and Medicinal Chemistry.

Mortenson et al., Evaluation of—Amino Acid Replacements in Protein Loops: Effects on Conformational Stability and Structure, Mar. 16, 2018, pp. 604-612, vol. 19, No. 6, Publisher: Chembiochem.

Richardson et al., In vitro genetic code reprogramming and expansion to study protein function and discover macrocyclic peptide ligands, Oct. 1, 2018, pp. 172-179, vol. 46, Publisher: Curr Opin Chem Biol.

Wilbs et al., Improving the Binding Affinity of in-Vitro-Evolved Cyclic Peptides by Inserting Atoms into the Macrocycle Backbone, Dec. 14, 2016, pp. 2299-2303, vol. 17, No. 24, Publisher: Chembiochem.

International Search Report received in PCT/JP2020/048981 mailed Mar. 9, 2021.

Written Opinion received in PCT/JP2020/048981 mailed Mar. 9, 2021.

Fontanillo et al., Synthesis of Highly Selective Submicromolar Microcystin-Based Inhibitors of Protein Phosphatase (PP)2A over PP1, Nov. 2, 2016, pp. 13985-13989, vol. 55, No. 45, Publisher: Angew Chem Int Ed Engl.

[Fig. 1]
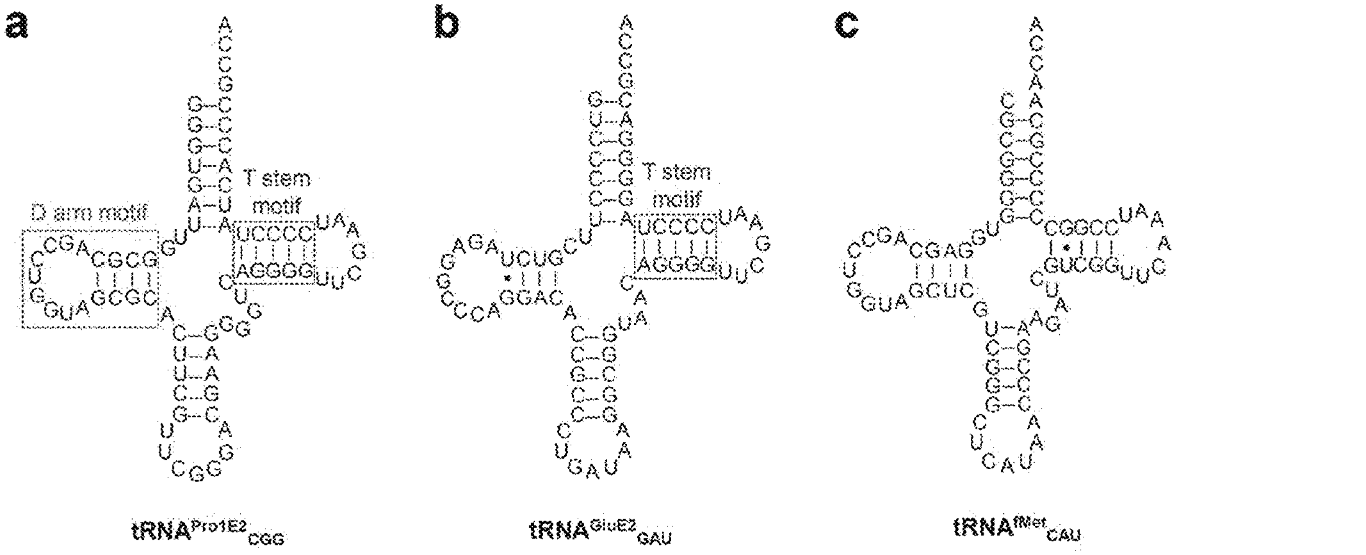
[Fig. 2]
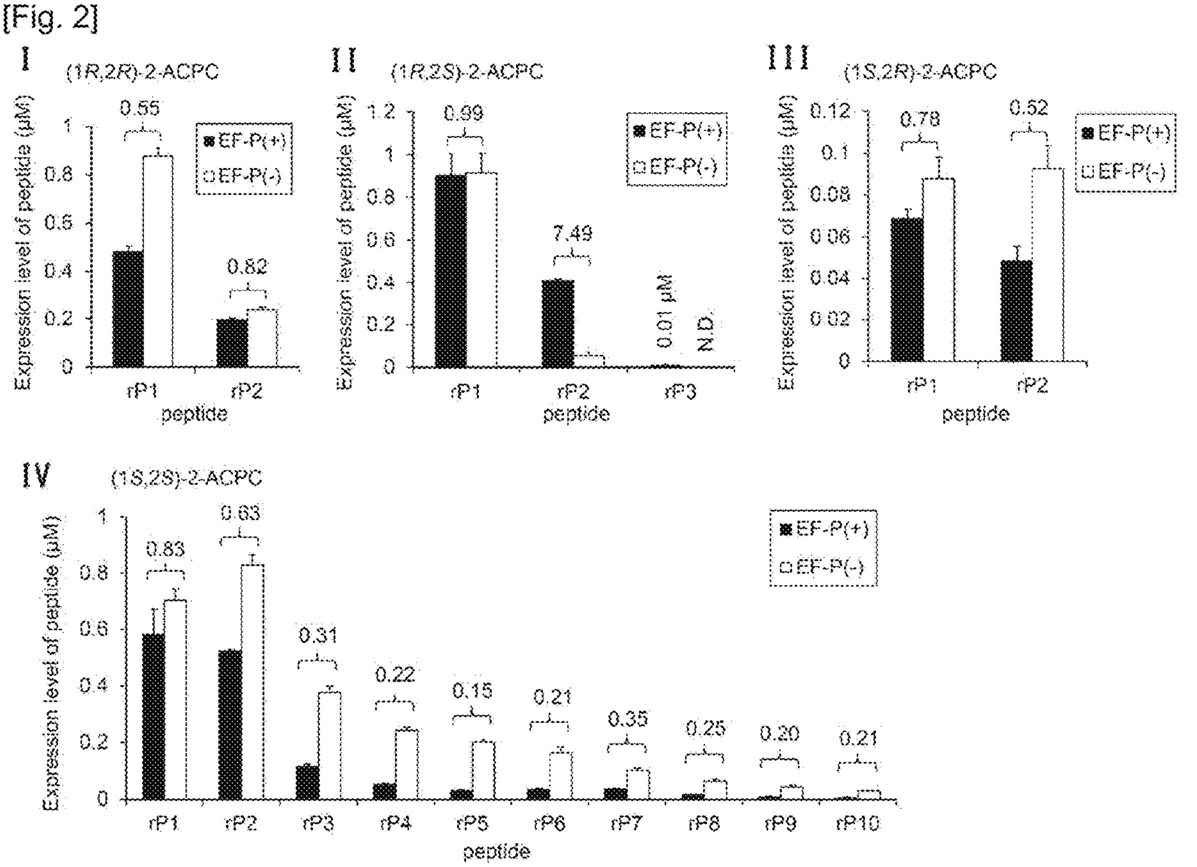

[Fig. 3]
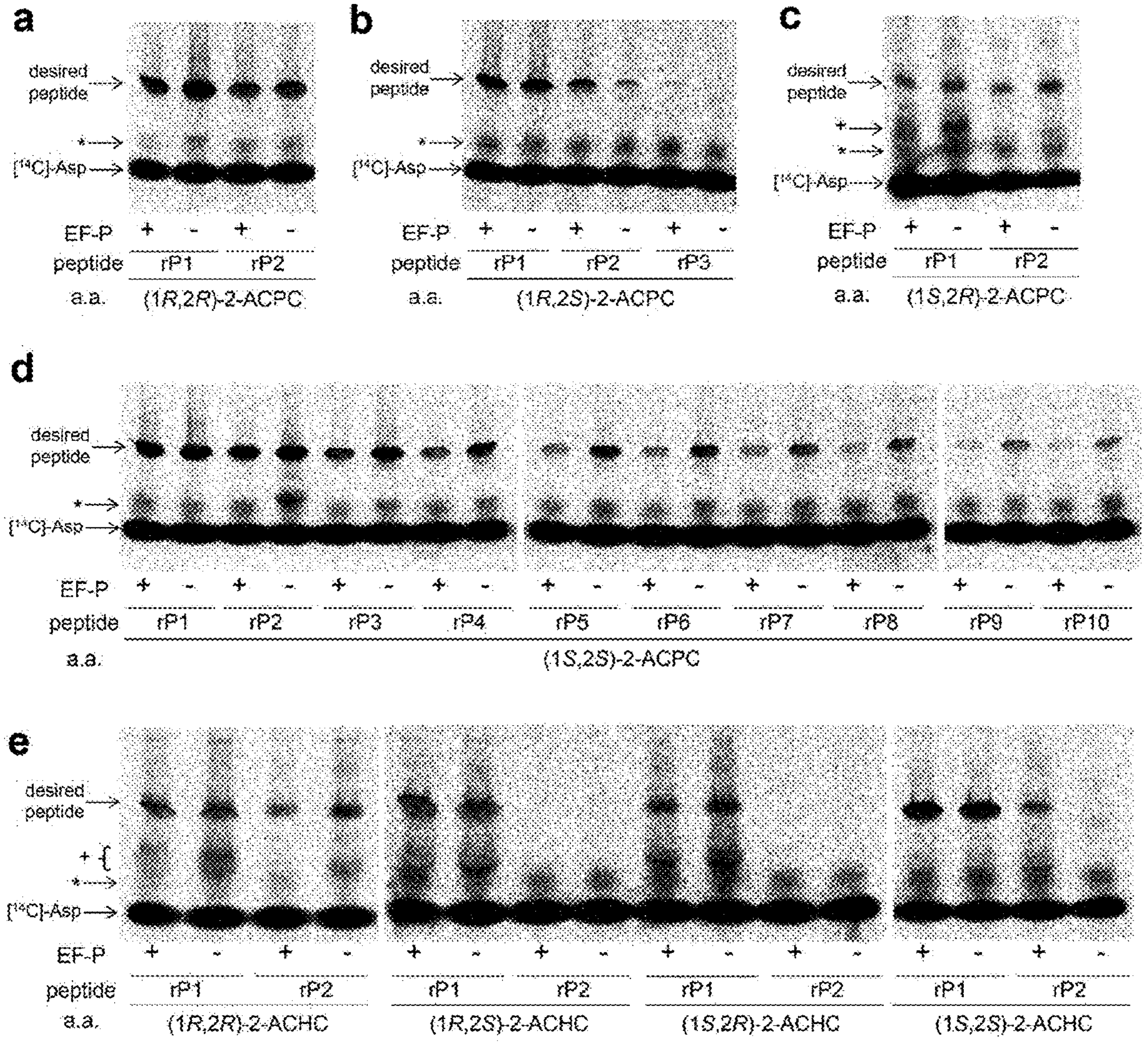

[Fig. 4]
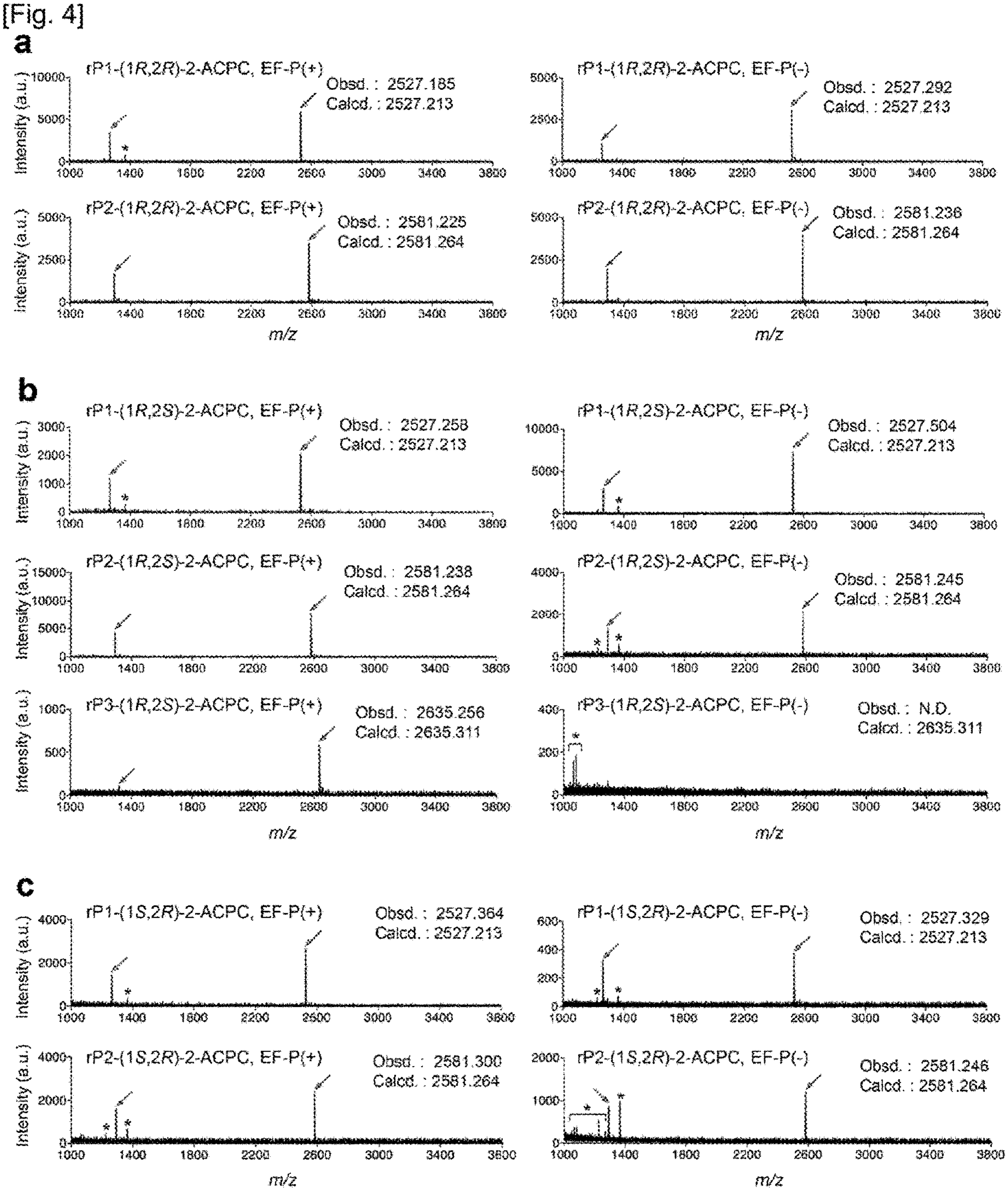

[Fig. 5]
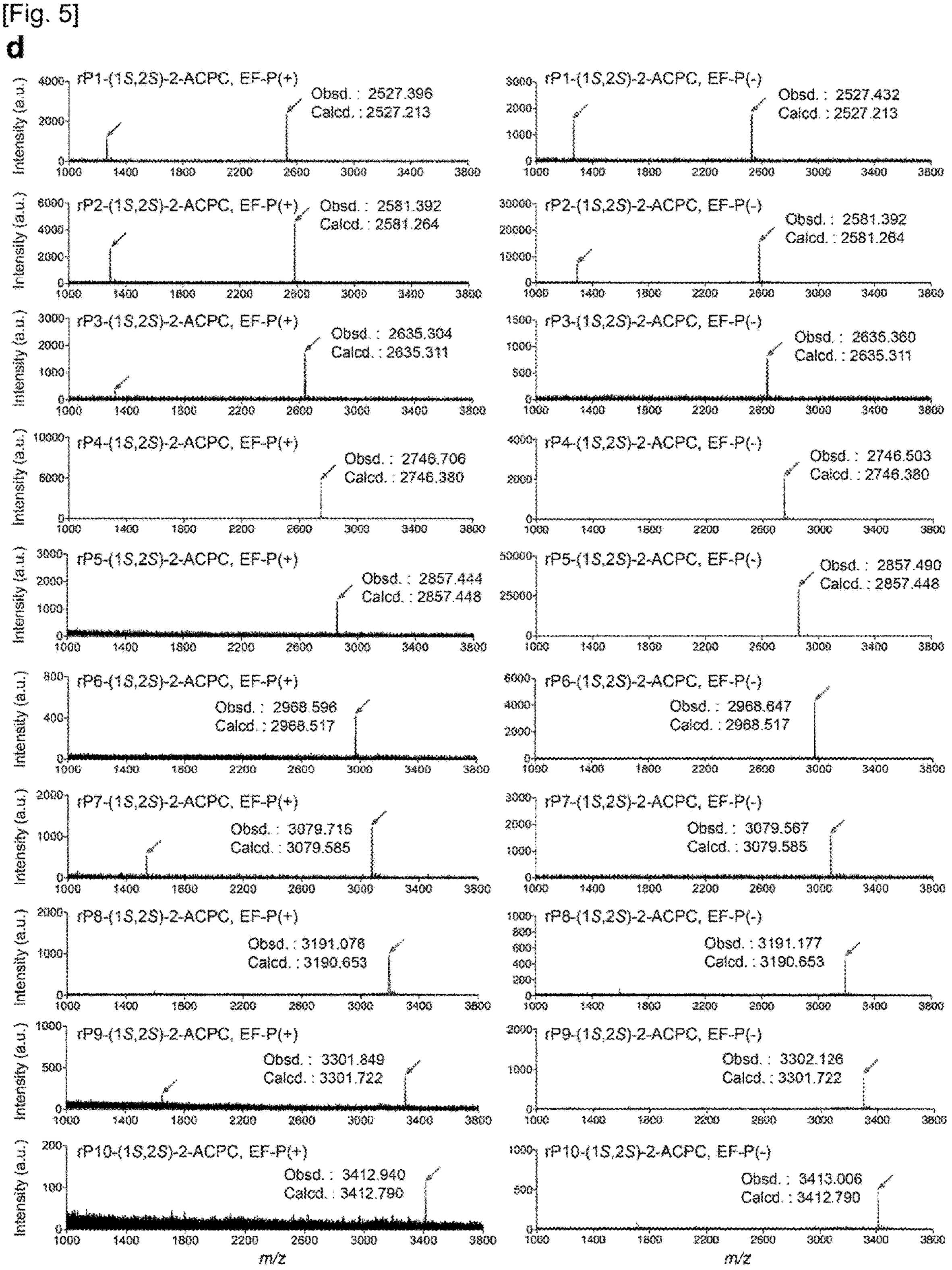

[Fig. 6]
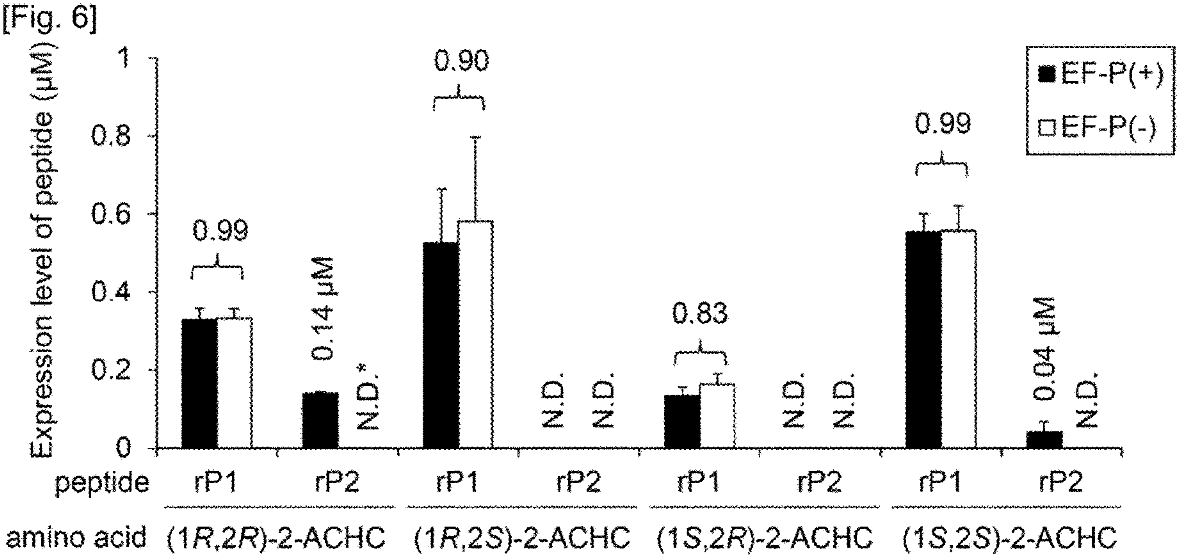

[Fig. 7]
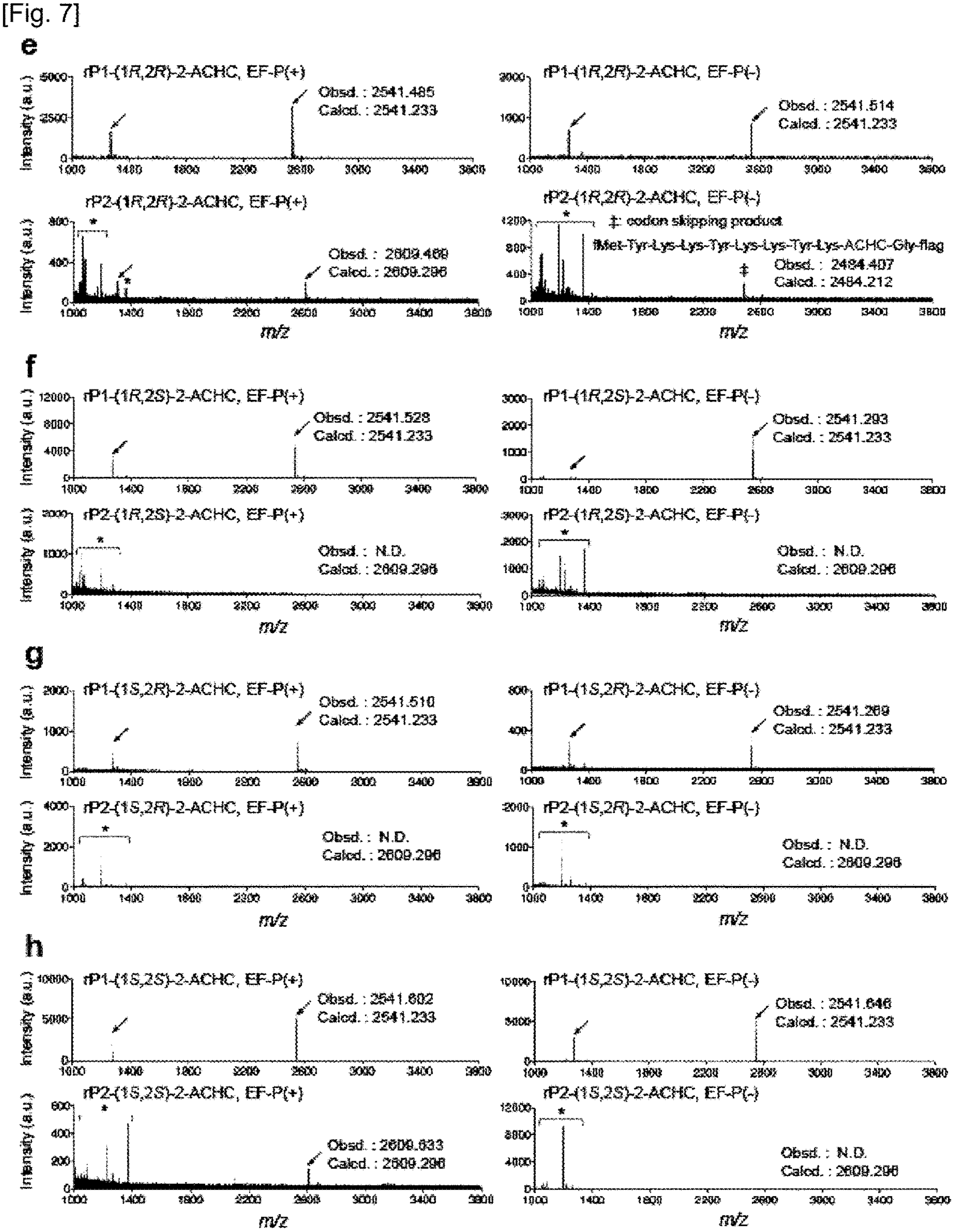

[Fig. 8]
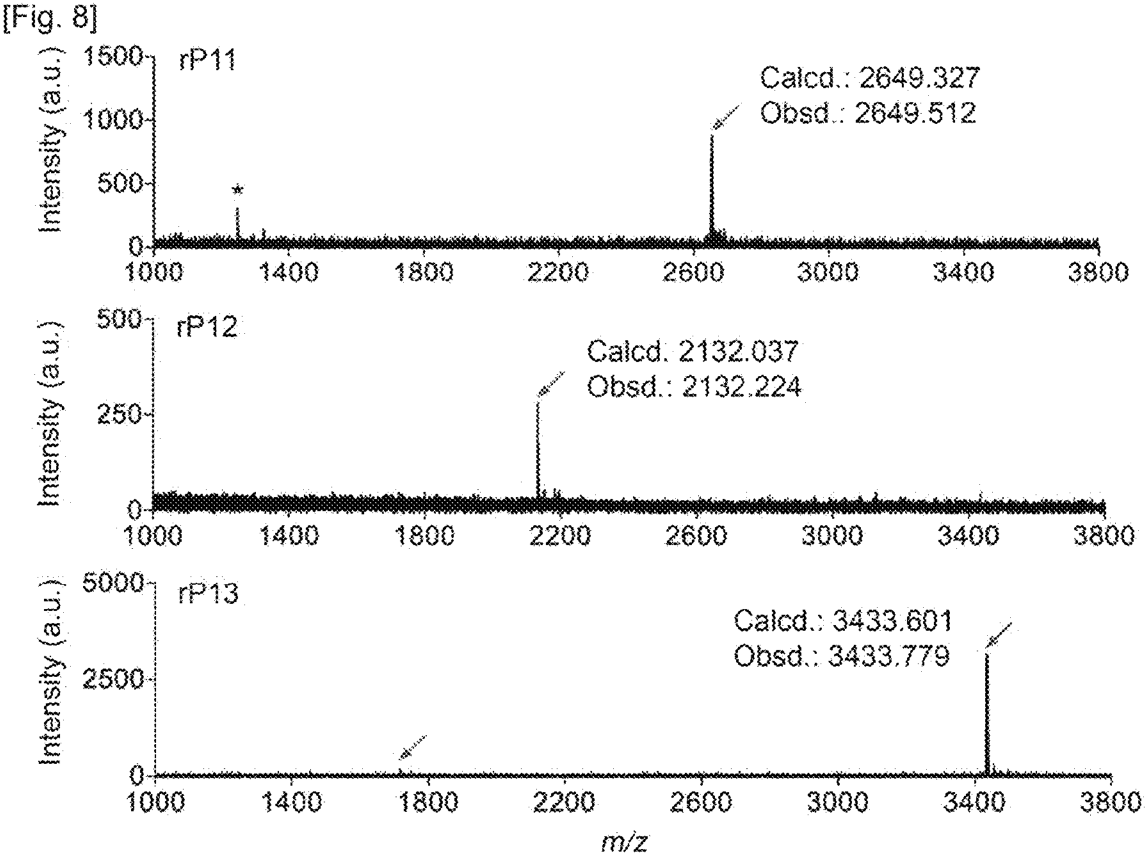
[Fig. 9]
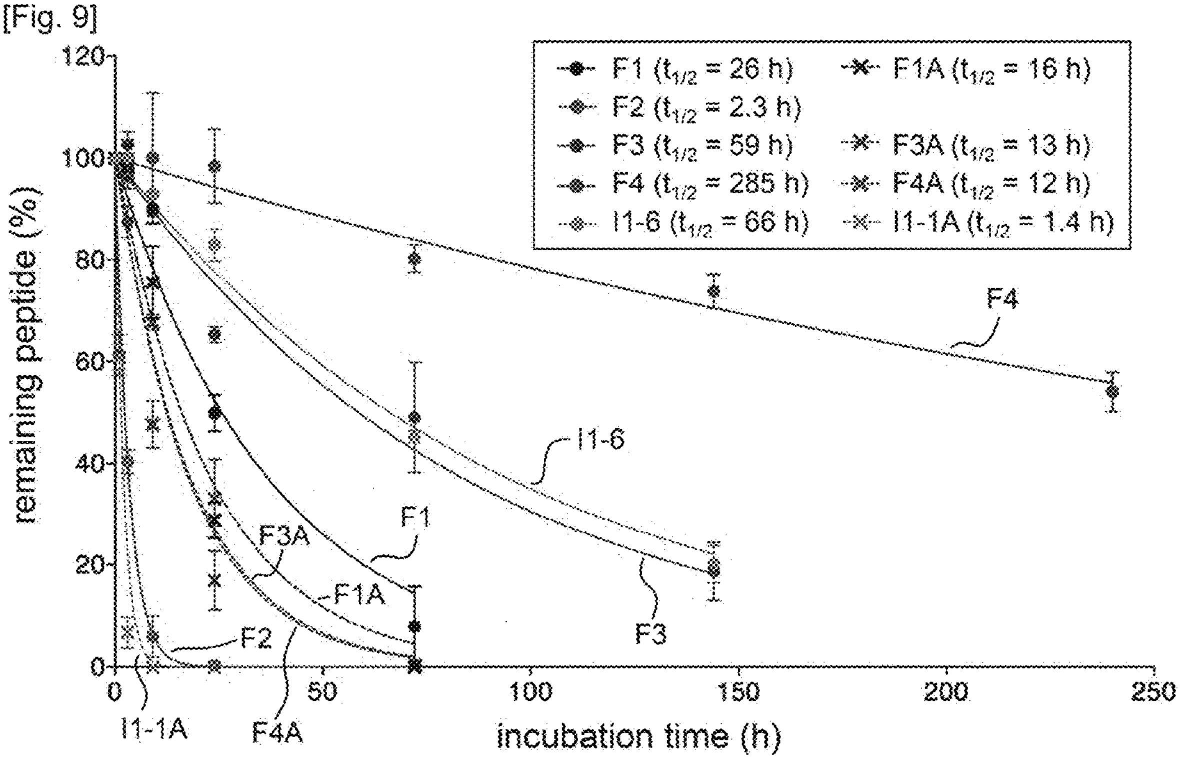

[Fig. 10]
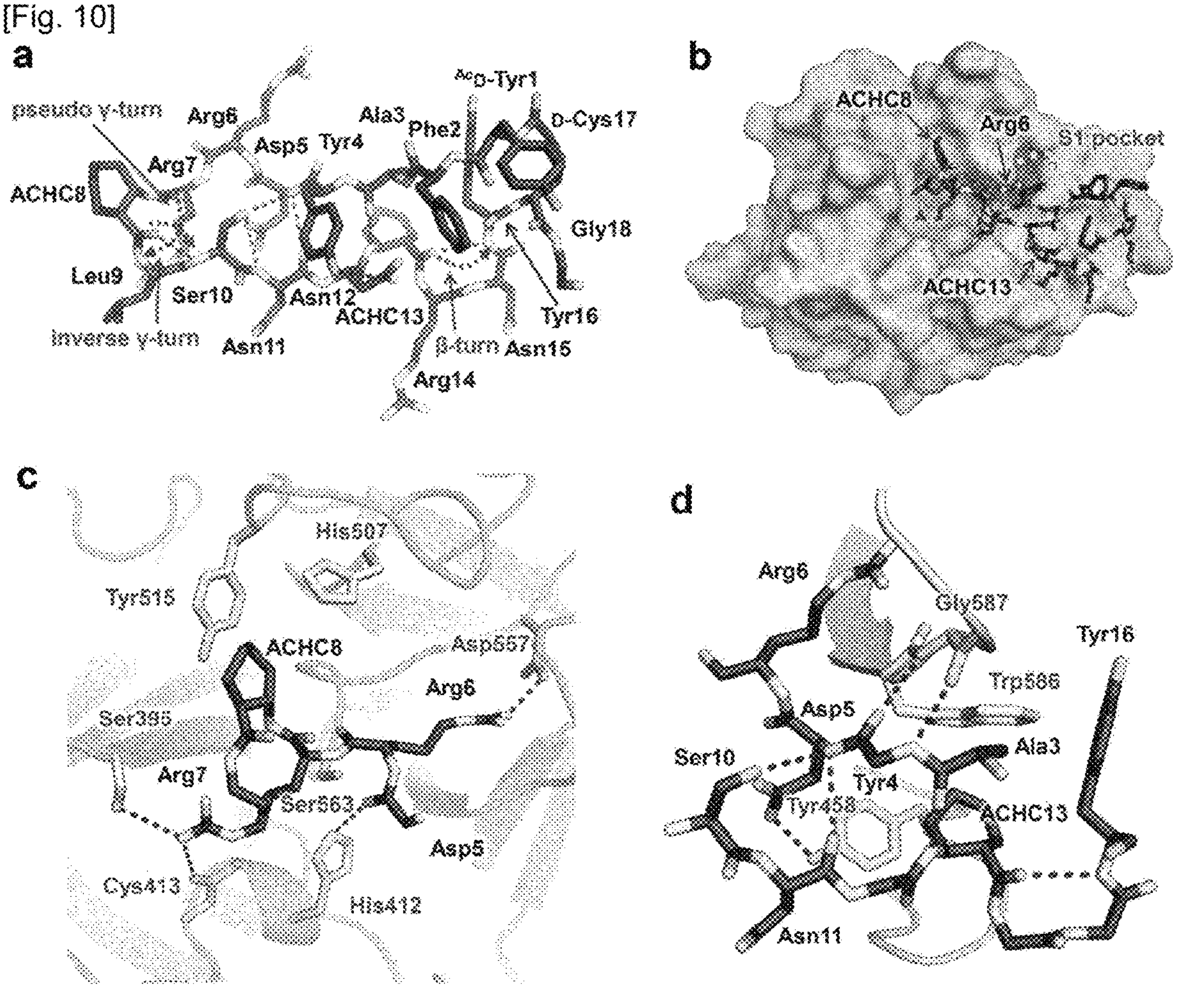
[Fig. 11]
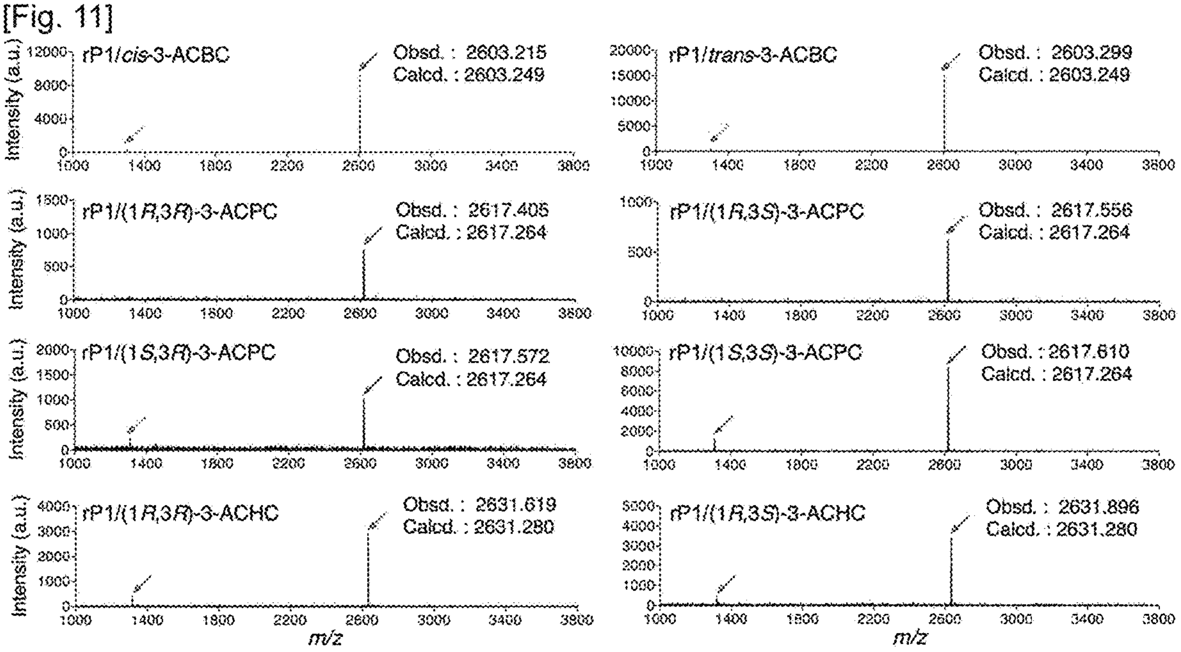

[Fig. 12]
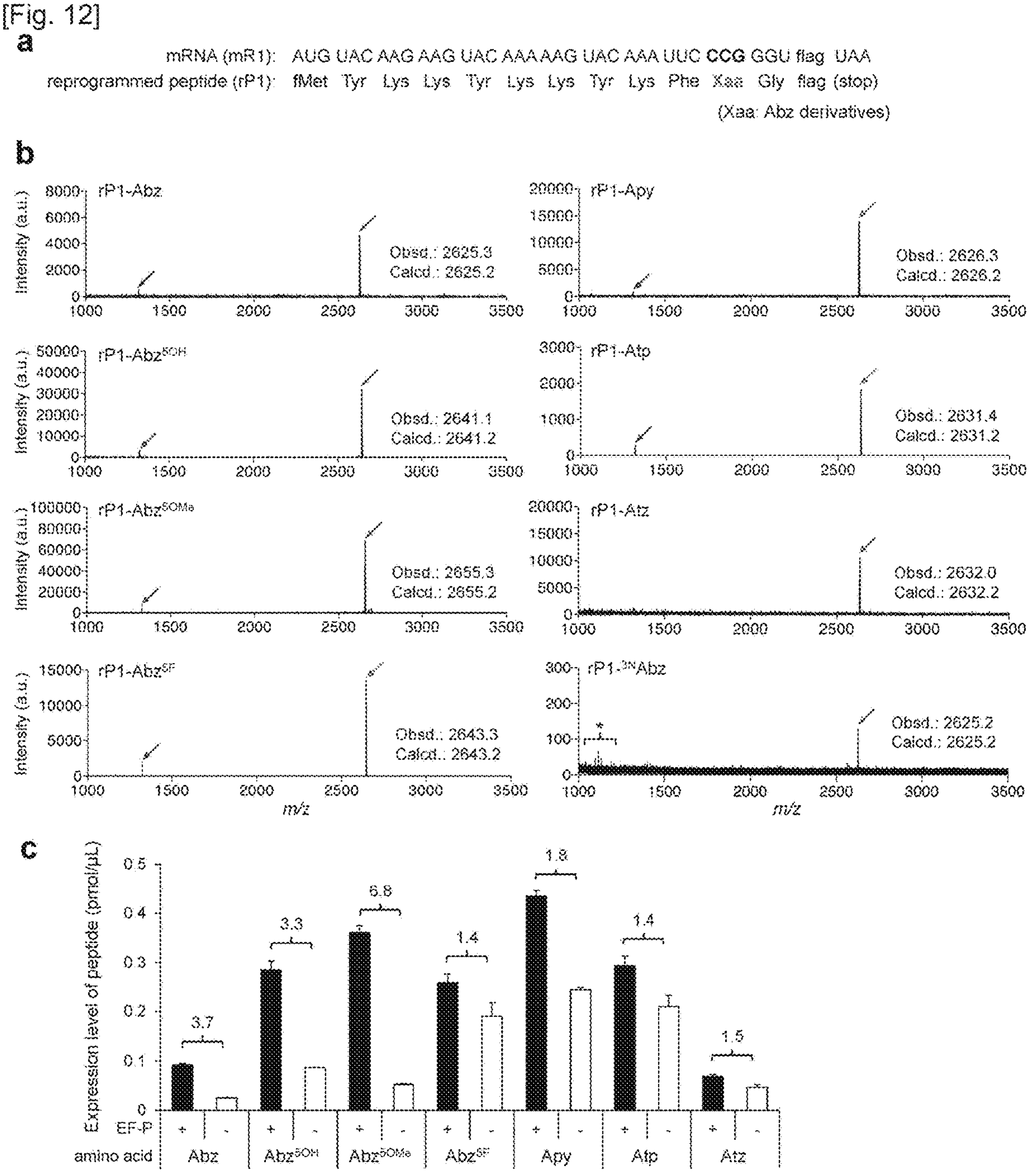

[Fig. 13]
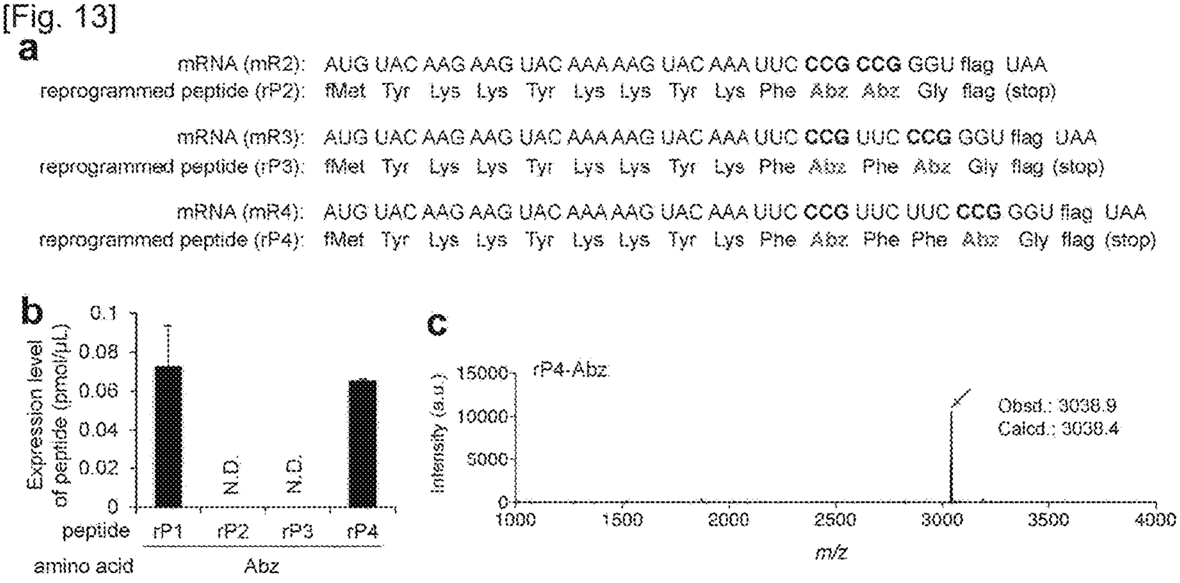

[Fig. 14]
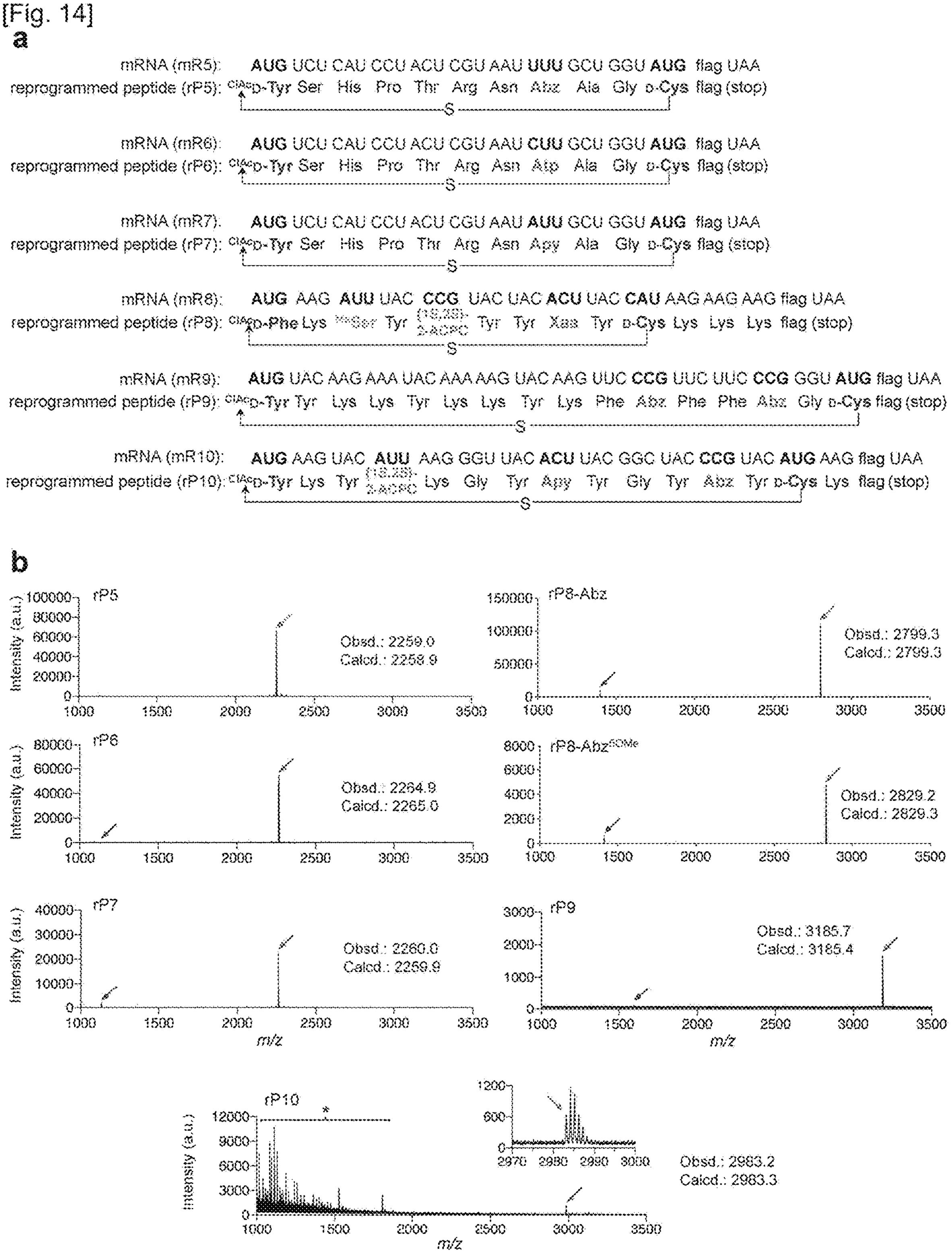

[Fig. 14C]
c
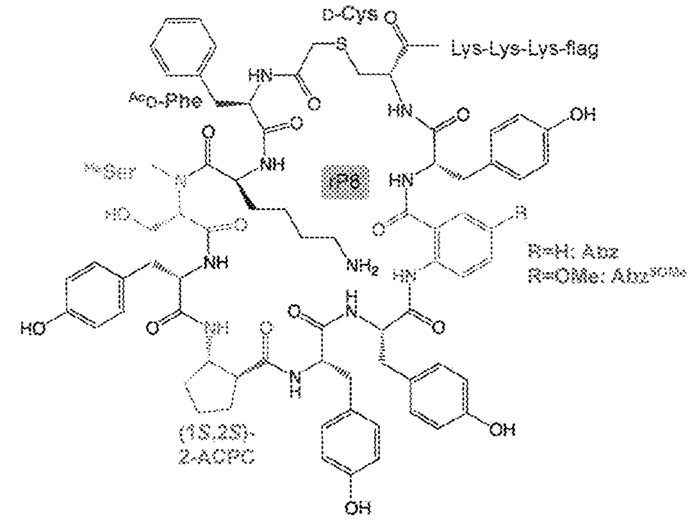
[Fig. 15]
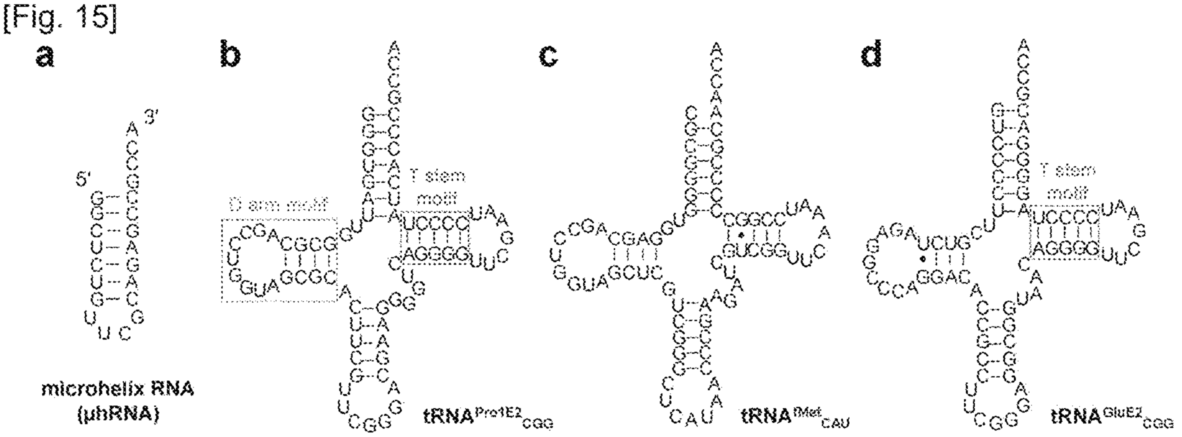

[Fig. 16]
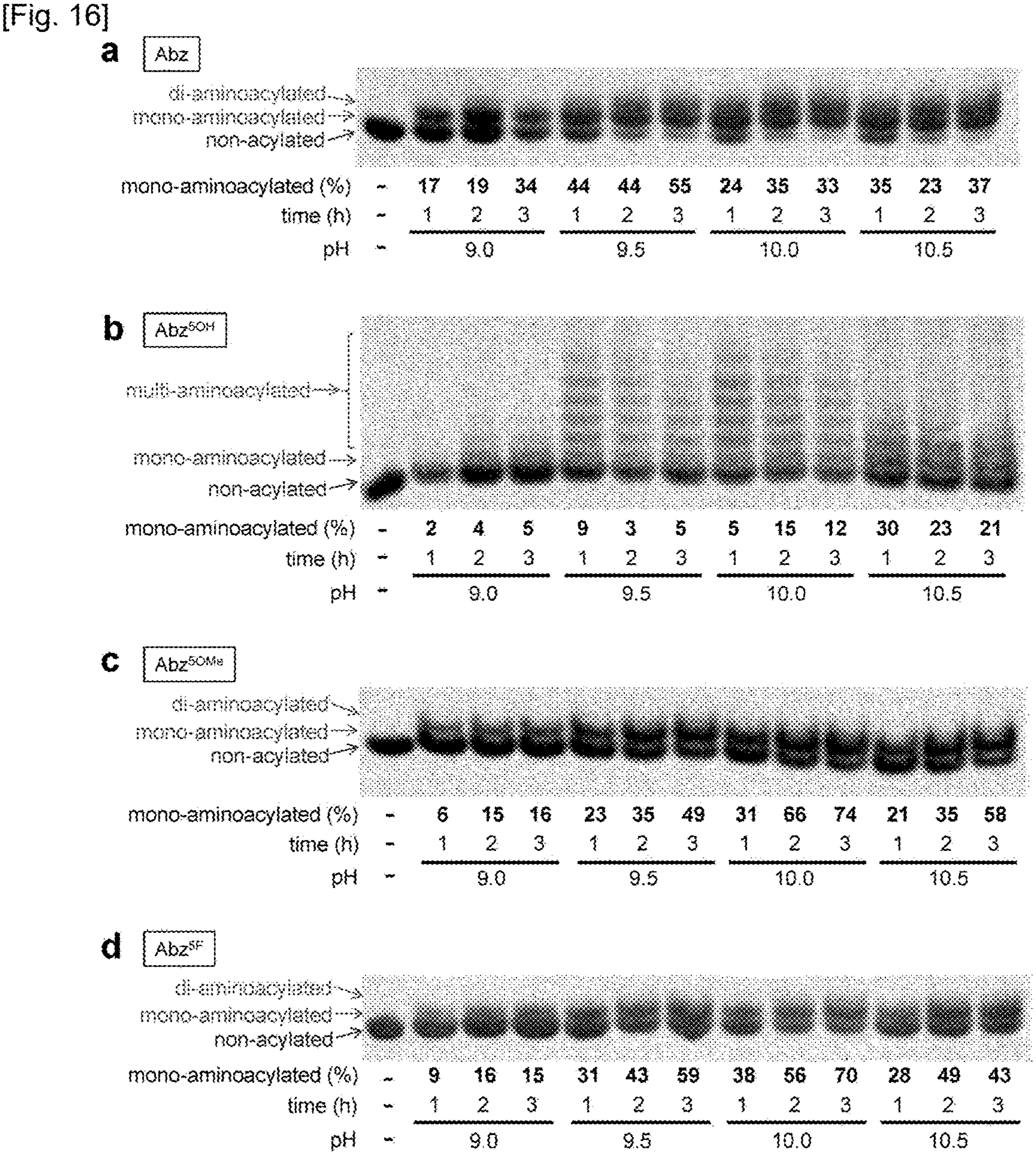

[Fig. 17]
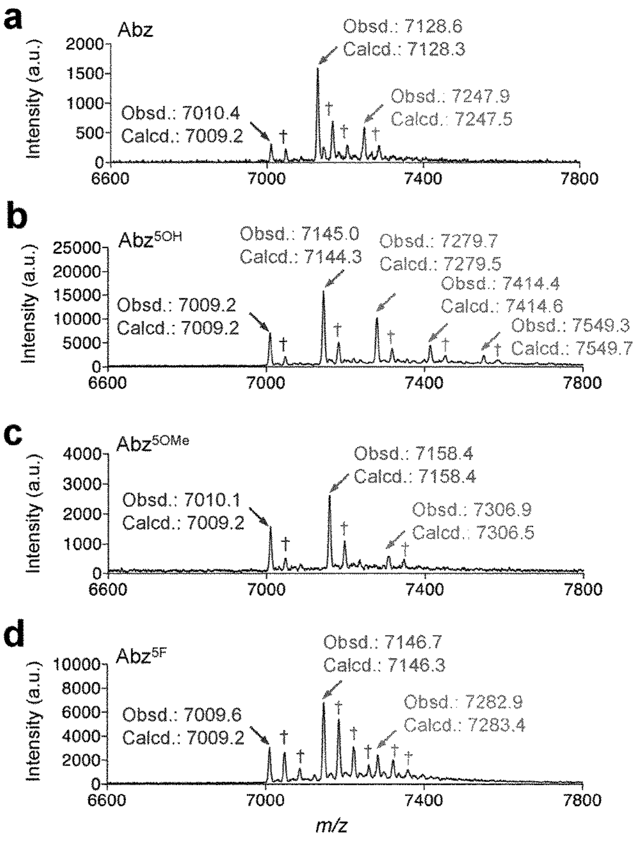

[Fig. 18]
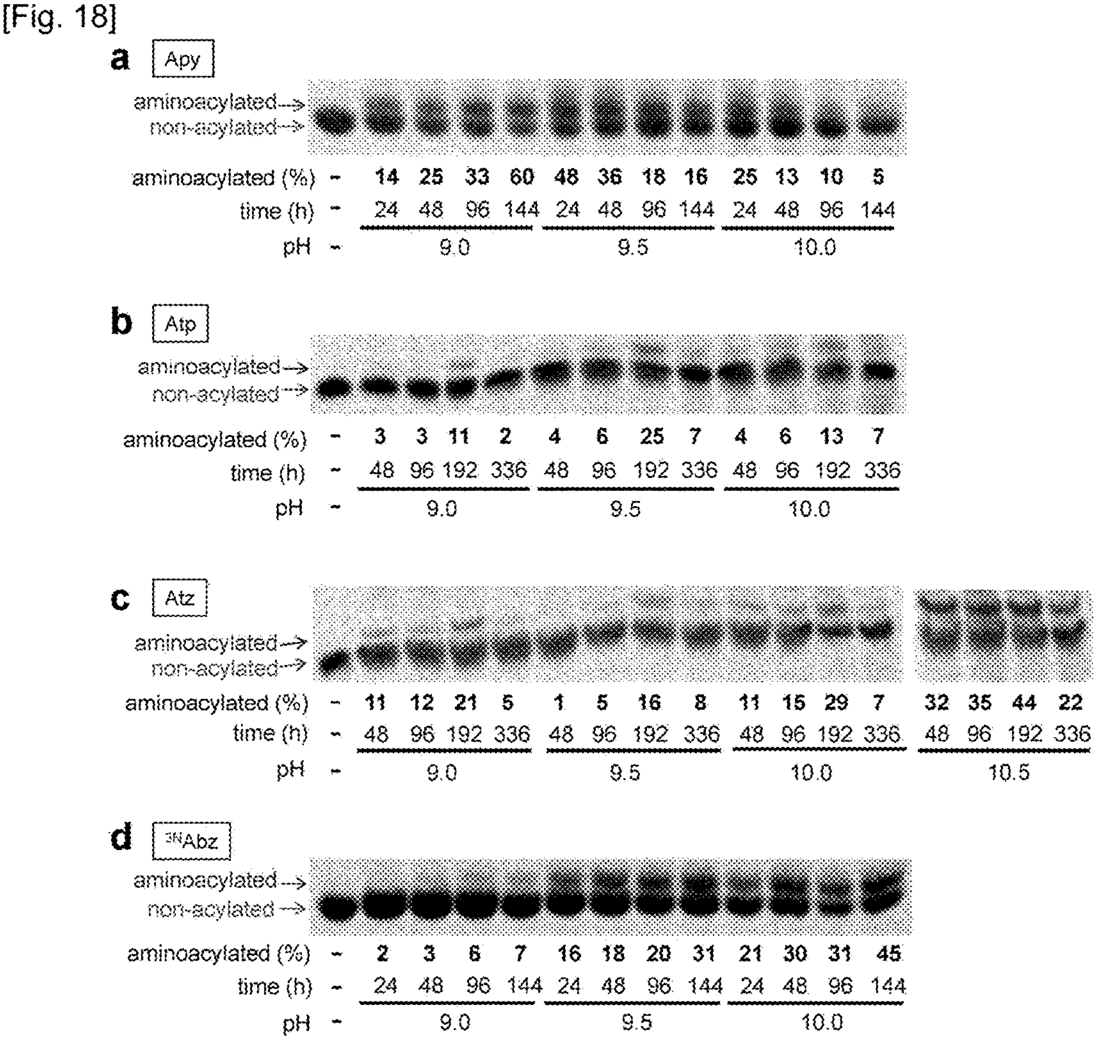

[Fig. 19]
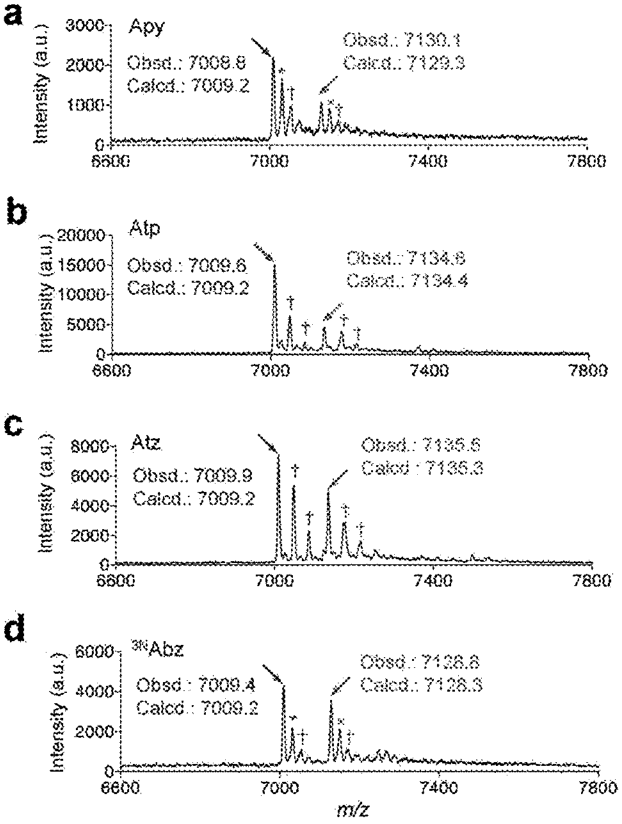
[Fig. 20]
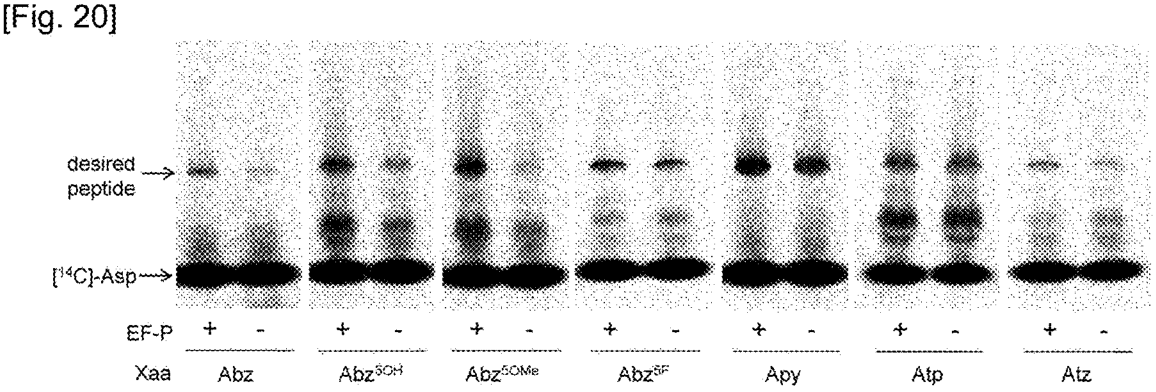
[Fig. 21]
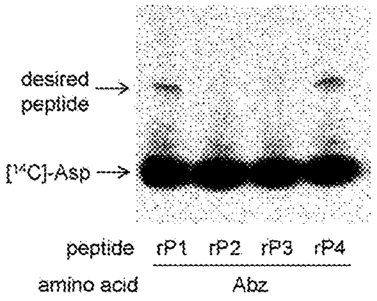

LIBRARY CONSTRUCTION METHOD, CYCLIC PEPTIDE, FXIIA BINDER AND IFNGR1 BINDER

REFERENCE TO A SEQUENCE LISTING SUBMITTED VIA PATENT CENTER

The content of the ASCII file of the sequence listing named "20251103_034574_034US1_subseq" which is 139,088 bytes in size was created on Nov. 3, 2025 and electronically submitted via Patent Center on Nov. 10, 2025 is incorporated herein by reference in its entirety.

TECHNICAL FIELD

The present invention relates to a production method for a library, a cyclic peptide, binding agents for FXIIa and IFNGR1, and the like.

BACKGROUND ART

Non-natural amino acids other than α-amino acids, such as β- and γ-ones are present in natural products and they are known to contribute to bioactivity, peptidase resistance, and target specificity, and moreover, membrane permeability.

In peptide synthesis using a ribosome translation system, 20 natural α-amino acids are generally used, so that it is the common practice to obtain a naturally occurring peptide containing a non-natural amino acid such as β- or γ-amino acid by the post translational modification or nonribosomal peptide synthesis.

A method of using genetic code manipulation for the ribosomal incorporation of β- or γ-amino acid or the like into a peptide chain has been studied, but it is presumed to be impossible to achieve consecutive elongation because of an essentially low incorporation efficiency of a non-natural amino acid.

The incorporation efficiency is presumed to be low mainly because the introduction speed of β-aminoacyl-tRNA into the A site of the ribosome by EF-Tu is slow and the speed of peptidyl transfer between β-amino acids is slow. Moreover, the slow peptidyl transfer is presumed to cause ribosomal stalling and drop-off of peptidyl-tRNA from the ribosome.

For example, Patent Document 1 discloses, as a method of improving the incorporation efficiency of a non-natural amino acid, a method of using a translation factor EF-P and a recombined $tRNA^{Pro1E2}$ for ribosomal synthesis. According to the method disclosed in Patent Document 1, use of $tRNA^{Pro1E2}$ improves the incorporation efficiency of a specific D-amino acid and non-cyclic β-amino acid, making it possible to perform incorporation of seven consecutive ones into a peptide.

CITATION LIST

Patent Document

Patent Document 1: WO2019/077887

SUMMARY

Technical Problem

From the standpoint of structural diversity or improving the properties of a compound, there is a demand for the development of a method of efficiently producing various peptides containing a non-natural amino acid.

It is said that a non-natural amino acid such as D-amino acid or non-cyclic 3-amino acid can be incorporated at an improved efficiency by the method of Patent Document 1 using tRNA. Patent Document 1, however, has not studied the ribosomal synthesis of a peptide containing a non-natural amino acid other than the aforesaid non-natural amino acid.

Solution to Problem

The present inventors have conducted intensive investigation in order to solve the aforesaid problem. As a result, it has been found that a cyclic peptide containing a cyclic β-, γ-, or δ-amino acid is expressed using a cell-free translation system, leading to the completion of the present invention. It is to be noted that the term "cyclic β-, γ-, or δ-amino acid" as used herein may be called "cAA".

The present invention is as follows.

[1] A method of producing a library including two or more cyclic peptides, wherein at least one of the cyclic peptides contained in the library has a cyclic structure having 4 to 30 amino acids or derivatives thereof and contains, in the cyclic structure, at least one selected from cyclic β-, γ-, and δ-amino acids (cAAs), including:

a step of preparing an mRNA library encoding a peptide having a sequence represented by the following formula (1);

$$-(Xaa)_{n1}- \quad (1)$$

[in the formula (1),

Xaas are each an arbitrary amino acid or derivative thereof, at least one of Xaas is one selected from cyclic β-, γ-, and δ-amino acids (cAAs), and n1 is an integer of 2 to 28]; and a step of using the mRNA library to express the peptide in a cell-free translation system and produce the library.

[2] A method of producing a library including two or more cyclic peptides, wherein at least one of the cyclic peptides contained in the library has a cyclic structure having 4 to 30 amino acids or derivatives thereof and contains, in the cyclic structure, at least one selected from cyclic β-, γ-, and δ-amino acids (cAAs), including:

a step of preparing an mRNA library encoding a peptide having a sequence represented by the following formula (1);

$$-(Xaa)_{n1}- \quad (1)$$

[in the formula (1),

Xaas are each an arbitrary amino acid or derivative thereof, at least one of Xaas is one selected from cyclic β-, γ-, and δ-amino acids (cAAs), and n1 is an integer of 2 to 28];

a step of binding puromycin to the 3' end of each of the mRNAs of the mRNA library to produce a puromycin-bound mRNA library; and a step of using the puromycin-bound mRNA library to express the peptide in a cell-free translation system and produce a peptide-mRNA complex library.

[3] The method of producing a library as described in [1] or [2], wherein the cell-free translation system contains a tRNA charged with one selected from cyclic β-, γ-, and δ-amino acids (cAAs) and the tRNA is a tRNA having a D-arm structure interactive with EF-P or a tRNA not having a D-arm structure interactive with EF-P.

[4] The method of producing a library as described in any of [1] to [3], wherein the cell-free translation system contains a tRNA charged with one selected from cyclic β-, γ-, and δ-amino acids (cAAs) and the tRNA is at least one selected from $tRNA^{Pro1E2}$ and $tRNA^{GluE2}$.

[5] The method of producing a library as described in any of [1] to [4], wherein the peptide having the sequence represented by the formula (1) is represented by the following formula (2);

$$Xaa1\text{-}(Xaa)n_1\text{-}Xaa2\text{-}(Xaax)_m \quad (2)$$

[in the formula (2),

Xaas are each an arbitrary amino acid or derivative thereof, at least one of Xaas is one selected from cyclic β-, γ-, and δ-amino acids (cAAs), Xaa1 and Xaa2 are each an amino acid or derivative thereof which forms a ring of the cyclic peptide, $Xaa_x$ is an arbitrary amino acid or derivative thereof, and n1 is an integer of 2 to 28, and m is an integer of 0 to 10.

[6] The method of producing a library as described in any of [1] to [5], wherein the cyclic β-, γ-, and δ-amino acids are each represented by any of the following formulas (I-1);

[Chemical formula 1]

(I-1)

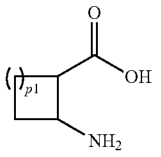

(in the formula (I-1), p1 is any integer of 1 to 4), the following formula (I-2);

[Chemical formula 2]

(I-2)

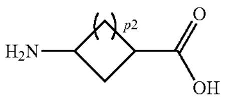

(in the formula (I-2), p2 is any integer of 1 to 4); the following formula (I-3);

[Chemical formula 3]

(I-3)

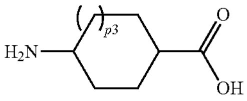

(in the formula (I-3), p3 is an integer of 1 or 2); and the following formula (I-4);

$$H_2N—Ar—COOH \quad (I\text{-}4)$$

(in the formula (I-4), Ar is a divalent aromatic group whose aromatic ring may be substituted with one or more substituents).

[7] The method of producing a library as described in any of [1] to [6], wherein two or more cAAs are contained at random in the sequence represented by the formula (1).

[8] The method of producing a library as described in any of [1] to [7], wherein two or more consecutive cAAs are contained in the sequence represented by the formula (1).

[9] The method of producing a library as described in any of [1] to [8], wherein 3 or more and 15 or less consecutive cAAs are contained in the sequence represented by the formula (1) and are each a cyclic β-amino acid represented by (1S,2S)-2-ACPC:

[Chemical formula 4]

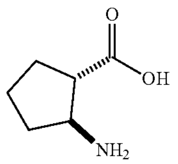

[10] The method of producing a library as described in any of [1] to [8], wherein the cAA is at least one cyclic β- or γ-amino acid (i) selected from:

[Chemical formula 5]

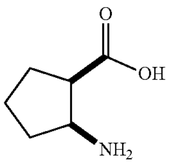

(1R,2S)-2-ACPC

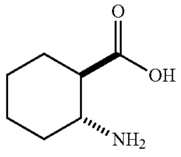

(1R,2R)-2-ACHC

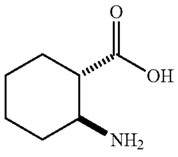

(1S,2S)-2-ACHC

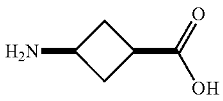

cis-3-ACBC

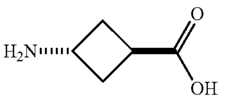

trans-3-ACBC

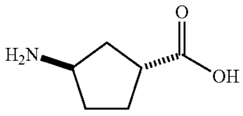

(1R,3R)-3-ACPC

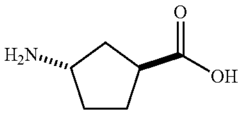

(1S,3S)-3-ACPC

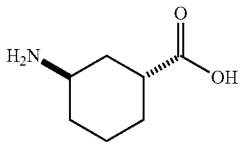

(1R,3R)-3-ACHC and/or at least one cyclic β- or γ-amino acid (ii) selected from:

[Chemical formula 6]

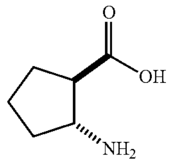

(1R,2R)-2-ACPC

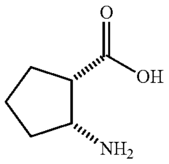

(1S,2R)-2-ACPC

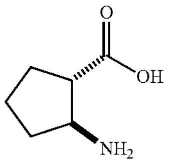

(1S,2S)-2-ACPC

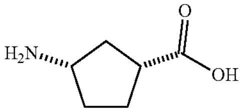

(1R,3S)-3-ACPC

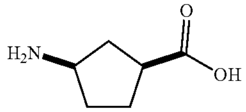

(1S,3R)-3-ACPC

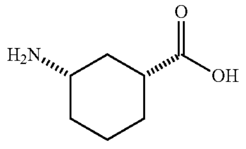

(1R,3S)-3-ACHC and the cell-free translation system contains a tRNA charged with the cyclic β- or γ-amino acid (i) and having a D-arm structure interactive with EF-P, and/or a tRNA charged with the cyclic β- or γ-amino acid (ii) and not having a D-arm structure interactive with EF-P.

[11] The method of producing a library as described in [10], wherein the tRNA charged with the cyclic β- or γ-amino acid (i) and having a D-arm structure interactive with EF-P is $tRNA^{Pro1E2}$ and the tRNA charged with the cyclic β- or γ-amino acid (ii) and not having a D-arm structure interactive with EF-P is $tRNA^{GluE2}$.

[12]A cyclic peptide including a cyclic structure composed of 4 to 30 amino acids or derivatives thereof or a pharmaceutically acceptable salt of the cyclic peptide, wherein of the 4 to 30 amino acids or derivatives of the cyclic structure, two amino acids or derivatives thereof, that is, Xaa1 and Xaa2, contain a structure for forming the cyclic structure, the Xaa1 and the Xaa2 have a linked structure via an amino acid sequence composed of 2 to 28 amino acids or derivatives thereof, the amino acid sequence composed of 2 to 28 amino acids or derivatives thereof is composed of at least one selected from cyclic β-, γ-, and δ-amino acids (cAAs) and an arbitrary amino acid or derivative thereof.

[13] The cyclic peptide or pharmaceutically acceptable salt thereof as described in [12], wherein the cyclic peptide is represented by the following formula (3);

$$Xaa1\text{-}(Xaa)_{n1}\text{-}Xaa2\text{-}(Xaa_x)_m \quad (3)$$

[in the formula (3),

Xaas are each an arbitrary amino acid or derivative thereof, at least one of the Xaas is a cyclic β-amino acid (cβAA), Xaa1 and Xaa2 are amino acids or derivatives thereof forming the ring of the cyclic peptide, n1 is an integer of 10 to 16, $Xaa_x$ is an arbitrary amino acid or derivative thereof, and m is an integer of 0 to 10], and supposing that Xaa1 is a first amino acid, at least one cAA is present in a 5 to 9-th position.

[14] The cyclic peptide or pharmaceutically acceptable salt thereof as described in [13], wherein at least one of Xaas is a basic amino acid or derivative thereof.

[15] The cyclic peptide or pharmaceutically acceptable salt thereof as described in [13] or [14], wherein (Xaa)n1 in the formula (3) is any one selected from the following f1 to f4:

[Chemical formula 7]

| | |
|---|---|
| -NDRSTR-cAA-RLVA- | f1 |
| -PRLFN-cAA-SYLRR- | f2 |
| -FAYDRR-cAA-LSNN-cAA-RNT- | f3 |
| -RYT-cAA-NRLF-cAA-NA- | f4 |

[in the formula, cAA is a cyclic β-amino acid].

[16] The cyclic peptide or pharmaceutically acceptable salt thereof as described in [13], wherein the cyclic peptide is represented by the following formula (3-1);

[Chemical formula 8]

(3-1)

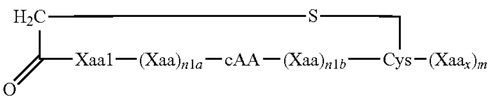

[in the formula (3-1),

Xaas are each an arbitrary amino acid or derivative thereof, cAA is a cyclic β-amino acid, n1a is an integer of 3 to 7 and n1b is an integer of 2 to 8 (with the proviso that the sum of n1a and n1b is an integer of 9 to 15), $Xaa_x$ is an arbitrary amino acid or derivative thereof, Xaa1 is Phe or Tyr, and m is an integer of 0 to 10, with the proviso that $(Xaa)_{n1a}$ does not contain cAA].

[17] The cyclic peptide or pharmaceutically acceptable salt thereof as described in [16], wherein at least one of Xaas is a basic amino acid or derivative thereof.

[18] The cyclic peptide or pharmaceutically acceptable salt thereof as described in [16] or [17], wherein a difference (absolute value) between n1a and n1b is 4 or less.

[19] The cyclic peptide or pharmaceutically acceptable salt thereof as described in any of [13] to [18], wherein the cyclic peptide is any one of the following F1 to F4;

[Chemical formula 9]

F1

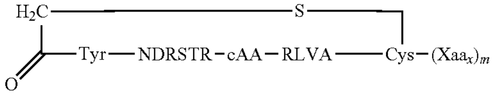

-continued

F2

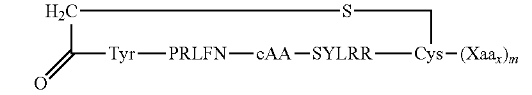

F3

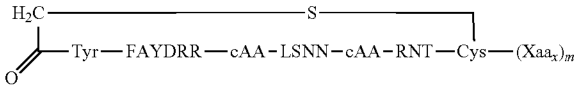

F4

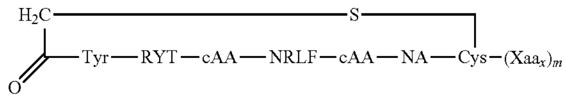

[in the formula, cAAs are each independently a cyclic β-amino acid, $Xaa_x$ is an arbitrary amino acid or derivative thereof, and m is an integer of 0 to 10].

[20] The cyclic peptide or pharmaceutically acceptable salt thereof as described in any of [13] to [19], wherein the cyclic β-amino acid is represented by the following formula (I-1);

[Chemical formula 10]

(I-1)

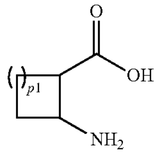

(in the formula (I-1), p1 is any integer of 1 to 4).

[21] The cyclic peptide or pharmaceutically acceptable salt thereof as described in [12], wherein the cyclic peptide is represented by the following formula (4);

$$Xaa1\text{-}(Xaa)_{n1}\text{-}Xaa2\text{-}(Xaa_x)_m \quad (4)$$

[in the formula (4),

Xaas are each an arbitrary amino acid or derivative thereof, at least one of Xaas is a cyclic β-amino acid (cAA), Xaa1 and Xaa2 are amino acids or derivatives thereof forming the ring of the cyclic peptide, n1 is an integer of 9 to 15, $Xaa_x$ is an arbitrary amino acid or derivative thereof, and m is an integer of 0 to 10], and supposing that Xaa1 is a first amino acid, at least one cAA is present as a 5 to 8-th one.

[22] The cyclic peptide or pharmaceutically acceptable salt thereof as described in [21], wherein (Xaa)n1 in the formula (4) is any one selected from the following i1-1 to i1-6:

[Chemical formula 11]

-FGVR-cAA-FYNRT- i1-1

-VGLN-cAA-SLNRT- i1-2

-FSLR-cAA-SFNRSRG- i1-3

-FALN-cAA-R-cAA-NRR- i1-4

-FGV-cAA-cAA-FYNRT- i1-5

-PRYNL-cAA-GASPRF-cAA-N- i1-6

[in the formula, cAA is a cyclic β-amino acid].

[23] The cyclic peptide or pharmaceutically acceptable salt thereof as described in [21], wherein the cyclic peptide is represented by the following formula (4-1);

[Chemical formula 12]

(4-1)

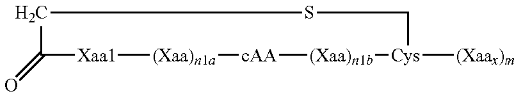

[in the formula (4-1),

Xaa is an arbitrary amino acid or derivative thereof, cAA is a cyclic β-amino acid, n1a is an integer of 3 to 6 and n1b is an integer of 5 to 8 (with the proviso that the sum of n1a and n1b is an integer of 8 to 14), $Xaa_x$ is an arbitrary amino acid or derivative thereof, Xaa1 is Phe or Tyr, and m is an integer of 0 to 10, with the proviso that $(Xaa)_{n1a}$ does not contain cAA].

[24] The cyclic peptide or pharmaceutically acceptable salt thereof as described in any of [21] to [23], wherein the cyclic peptide is any of the following I1-1 to I1-6,

[Chemical formula 13]

I1-1

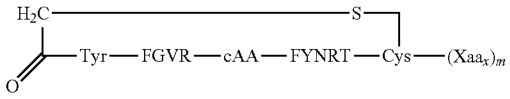

I1-2

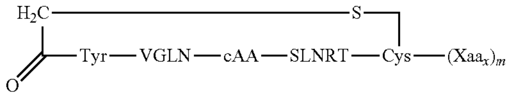

I1-3

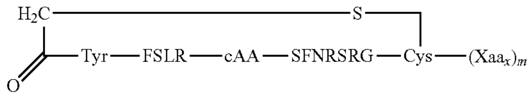

I1-4

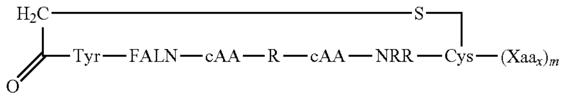

I1-5

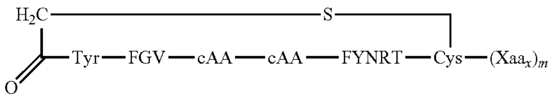

I1-6

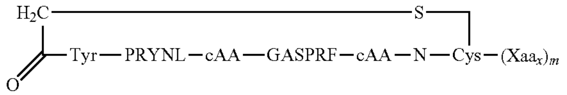

[in the formula, cAAs are each independently a cyclic β-amino acid, $Xaa_x$ is an arbitrary amino acid or derivative thereof, and m is an integer of 0 to 10].

The cyclic peptide or pharmaceutically acceptable salt thereof as described in any of to [24], wherein the cyclic β-amino acid is represented by the following formula (I-1);

[Chemical formula 14]

(I-1)

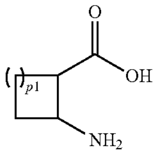

(in the formula (I-1), p1 is any integer of 1 to 4).

[26] A binding agent for activated blood coagulation factor XII (FXIIa), containing the cyclic peptide or pharmaceutically acceptable salt thereof as described in any of [13] to [20].

[27] A binding agent for type II interferon receptor complex (IFNGR1), containing the cyclic peptide or pharmaceutically acceptable salt thereof as described in any of [21] to [25].

Advantageous Effects of Invention

The present invention can provide a method of producing a library including cyclic peptides containing cyclic β-, γ-, and δ-amino acids.

BRIEF DESCRIPTION OF DRAWINGS

FIG. 1 shows the secondary structure of tRNA used for the incorporation of a cAA in Examples, in which FIG. 1*a* shows the secondary structure of $tRNA^{Pro1E2}$CGG (SEQ ID NO: 11). The D-arm structure (D-arm motif) for EF-P binding consists of a D-loop of 9 bases closed by a stable 4 base pair stem. In addition, it has a T-stem (T-stem motif) for EF-Tu binding. FIG. 1*b* shows the secondary structure of $tRNA^{GluE2}_{GAU}$ (SEQ ID NO: 14). It has a T-stem (T-stem motif) for EF-Tu binding, which is the same as that of $tRNA^{Pro1E2}$. FIG. 1*c* shows $tRNA^{fMet}_{CAU}$ (SEQ ID NO: 18) used for the incorporation of $^{ClAc}$D-Phe by an initiation codon AUG.

FIGS. 2I, 2II, 2III, and 21V respectively show the results of the expression levels of peptides when (1R,2R)-2-ACPC, (1R,2S)-2-ACPC, (1S,2R)-2-ACPC, and (1S,2S)-2-ACPC were introduced into peptides rP1 to rP10. The 2-ACPC was assigned to a CCG codon by using pre-charged 2-ACPC-$tRNA^{Pro1E2}_{CGG}$. The black bar indicates the translation performed in the presence of EF-P (EF-P(+)) and the white bar indicates the translation performed in the absence of EF-P (EF-P(−)). The numeral on the bar graph is a ratio (EF-P(+)/EF-P(−)) of the expression level in the presence of EF-P to that in the absence of EF-P. The concentration of EF-P when the translation was performed in the presence of EF-P was 5 μM. The reaction time was set at 30 minutes. The term "N.D." means "not detected".

FIGS. 3*a*, 3*b*, 3*c*, 3*d*, and 3*e* respectively show the tricine SDS-PAGE analysis results when (1R,2R)-2-ACPC, (1R,2S)-2-ACPC, (1S,2R)-2-ACPC, (1S,2S)-2-ACPC, and 2-ACHC were introduced into peptides, in which + indicates an impurity derived from the drop-off of peptidyl-tRNA and * indicates a peak of a template-independent impurity derived from the translation system.

FIGS. 4*a*, 4*b*, and 4*c* respectively show the MALDI-TOF MS spectra of peptides containing (1R,2R)-2-ACPC, (1R,2S)-2-ACPC, and (1S,2R)-2-ACPC, respectively. The concentration of EF-P in the translation in the presence of EF-P was 5 μM. The arrow indicates the peak of a desired peptide. The arrow on the high-molecular-weight side (high m/z side) indicates a monovalent ion and the arrow on the low-molecular-weight side (low m/z side) indicates a divalent ion. The terms "Calcd." and "Obsd." mean a calculated value and an observed value, respectively. The term "N.D." means "not detected". The * is a peak of a template-independent impurity derived from the translation system.

FIG. 5 shows the MALDI-TOF MS spectra of peptides containing (1S,2S)-2-ACPC. The concentration of EF-P in the translation in the presence of EF-P was 5 μm. The arrow indicates the peak of a desired peptide. The arrow, "Calcd.", and "Obsd." in the spectra have the same meanings as those in FIG. 4. The "N.D." means "not detected".

FIG. 6 shows the results of the expression levels of peptides when (1R,2R)-2-ACHC, (1R,2S)-2-ACHC, (1S,2R)-2-ACHC, and (1S,2S)-2-ACHC were introduced into a peptide rP1 or rP2. The 2-ACHC was assigned to a CCG codon by using pre-charged 2-ACHC-$tRNA^{Pro1E2}_{CGG}$. The black bar indicates the results of the translation performed in the presence of EF-P (EF-P(+)) and the white bar indicates the results of the translation performed in the absence of EF-P (EF-P(−)). The numeral on the bar graph is a ratio (EF-P(+)/EF-P(−)) of the expression level in the presence of EF-P to that in the absence of EF-P. The concentration of EF-P in the translation in the presence of EF-P was 5 μM. The reaction time was set at 30 minutes. The "N.D." means "not detected".

FIGS. 7*e*, 7*f*, 7*g*, and 7*h* respectively show the MALDI-TOF MS spectra of peptides containing (1R,2R)-2-ACHC, (1R,2S)-2-ACHC, (1S,2R)-2-ACPC, and (1S,2S)-2-ACHC. The arrow, "Calcd.", "Obsd.", and * in the spectra have the same meanings as those in FIG. 4.

FIG. 8 shows the MALDI-TOF MS spectra of peptides rP11, rP12, and rP13. The arrow, "Calcd.", "Obsd.", "N.D." and * in the spectra have the same meanings as those in FIG. 4.

FIG. 9 shows the serum stability assay results of peptides bound to FXIIa and IFNGR1. Each of F1, F2, F3, F4, 11-6, F1A, F3A, F4A, and I1-1A was co-incubated with an internal standard peptide in the human serum at 37° C. The relative intensity of each peptide to the standard peptide was estimated by LC/MS at 0, 1, 3, 9, 24, 72, 144, and 240 hours. The relative intensity at 0 hour was defined as 100%.

FIG. 10 shows the X-ray crystallographic analysis results of the structure of F3 bound to FXIIa, in which FIG. 10*a* is an overall structure of F3 shown by a stick model. Hydrogen bonding is indicated by a broken line and a local turn structure is present at the place indicated by an arrow. FIG. 10*b* is an overall structure of a FXIIa-F3 complex. The S1 pocket for housing an Arg residue (Arg6) of the substrate therein is indicated by a dotted line. FIG. 10*c* shows the binding of an Asp5-ACHC8 segment to FXIIa. FIG. 10*d* shows the binding of the molecular center portion of F3 to FXIIa.

FIG. 11 shows the MALDI-TOF MS spectra of peptides containing cis-3-ACBC, trans-3-ACBC, (1R,3S)-3-ACPC, (1R,3S)-3-ACPC, (1S,3R)-3-ACPC), (1S,3S)-3-ACPC, (1R,3R)-3-ACHC, and (1R,3S)-3-ACHC. The arrow, "Calcd.", "Obsd.", and * in the spectra have the same meanings as those in FIG. 4.

FIG. 12 shows the ribosomal incorporation of an Abz derivative into a peptide rP1. FIG. 12*a* shows the sequence of the peptide (rP1) (SEQ ID NO: 334) corresponding to mRNA (mR1) (SEQ ID NO: 324). The Abz derivative is assigned to a CCG codon by using a pre-charged aminoacyl-$tRNA^{Pro1E2}$cGG. The flag is GACUACAAGGACGACGACGACAAG (SEQ ID NO: 344) in mR1 and Asp-Tyr-Lys-Asp-Asp-Asp-Asp-Lys (SEQ ID NO: 345) in rP1 (this also applies to FIG. 13 and FIG. 14). FIG. 12*b* shows the MALDI-TOF MS spectra of peptides containing an Abz derivative. The arrow, "Calcd.", "Obsd.", and * in the spectra have the same meanings as those in FIG. 4. FIG. 12*c* shows the expression level of the rP1 peptides estimated by autoradiography. The black bar indicates the translation performed in the presence of EF-P (EF-P(+)) and the white bar indicates the translation performed in the absence of EF-P (EF-P(−)). The numeral on the bar graph indicates a ratio (EF-P(+)/EF-P(−)) of the expression level in the presence of EF-P to that in the absence of EF-P.

FIG. 13 shows the ribosomal incorporation of a plurality of Abzs into peptides (rP2 to rP4) (SEQ ID NOs: 335 to 337, respectively). FIG. 13*a* shows the sequences of the peptides (rP2 to rP4) corresponding to mRNAs (mR2 to mR4) (SEQ ID NOs: 325 to 327, respectively). FIG. 13*b* shows the expression levels of the peptides (rP1 to rP4) estimated by autoradiography. The term "N.D." means "not detected". FIG. 13*c* shows the MALDI-TOF MS spectrum of the Abz-containing rP4 peptide. The arrow indicates a monovalent ion of a desired peptide. The terms "Calcd." and "Obsd." have the same meanings as those in FIG. 4.

FIG. 14 shows the ribosomal incorporation of an Abz derivative into cyclic peptides (rP5 to rP10) (SEQ ID NOs: 338 to 343, respectively). FIG. 14*a* shows the sequence of the cyclic peptides (rP5 to rP10) corresponding to mRNAs (mR5 to mR10) (SEQ ID NOs: 328 to 333, respectively). The thiol group of D-Cys forms a thioether bond with an N-terminal chloroacetyl group. FIG. 14*b* shows the MALDI-TOF MS spectra of the peptides (rP5 to rP10). The arrow, "Calcd.", "Obsd.", and * in the spectra have the same meanings as those in FIG. 4.

FIG. 14C shows the structure of rP8 peptide containing Abz or $Abz^{5OMe}$

FIG. 15 shows the secondary structure of a μhRNA and tRNAs used in the incorporation of a cAA in Examples. FIG. 15*a* is the secondary structure of μhRNA (SEQ ID NO: 365). FIG. 15*b* is the secondary structure of $tRNA^{Pro1E2}$CGG (SEQ ID NO: 11). The D-arm structure (D-arm motif) for EF-P binding consists of a D-loop of 9 bases closed by a stable 4 base pair stem. It also has a T-stem (T-stem motif) for EF-Tu binding. The sequence of an anticodon loop is changed as needed in order to decode another codon as described in Table 14. FIG. 15*c* shows $tRNA^{fMet}$CAU (SEQ ID NO: 18) used for the incorporation of $^{ClAc}$D-Tyr and $^{ClAc}$D-Phe by an initiation codon AUG. FIG. 15*d* shows $tRNA^{GluE2}$CGG (SEQ ID NO: 307) used for the incorporation of (1S,2S)-2-ACPC by a CCG codon.

FIGS. 16*a, b, c*, and *d* respectively show the analysis results of acid modification PAGE when μhRNA was aminoacylated using Abz, $Abz^{5OH}$, $Abz^{5OMe}$ and $Abz^{5F}$ anhydrides. The bands were each detected by ethidium bromide staining. The center arrow indicates the position of desired mono-aminoacyl-μhRNA, while the upper and lower arrows respectively indicate the positions of a multiaminoacyl-μhRNA and a non-acylated μhRNA.

FIGS. 17*a, b, c*, and *d* respectively show the MALDI-TOF MS spectra of aminoacyl-μhRNAs obtained by the aminoacylation using Abz, $Abz^{5OH}$, $Abz^{5OMe}$ and $Abz^{5F}$. The arrow indicating the largest peak which is the second from the left is a peak of a desired monoaminoacyl-μhRNA. The arrow on a higher molecular weight side (higher m/z side) indicates a multiaminoacyl-μhRNA, while the arrow on a lower molecular weight side (lower m/z side) indicates a non-acylated μhRNA. The terms "Calcd." and "Obsd." have the same meanings as those in FIG. 4, while t indicates a potassium adduct.

FIGS. 18*a, b, c*, and *d* respectively show the analysis results of acid modification PAGE when μhRNA was aminoacylated using cyanomethyl esters (CME) of Apy, Atp, Atz, and $^{3N}$Abz, and flexizyme (eFx). The upper and lower arrows respectively show the positions of a desired aminoacyl-μhRNA and a non-acylated μhRNA.

FIGS. 19*a, b, c*, and *d* respectively show the MALDI-TOF MS spectra of aminoacyl-μhRNAs obtained by the aminoacylation using Apy, Atp, Atz, and $^{3N}$Abz. The arrow on the high molecular weight side (high m/z side) indicates a desired monoacyl-μhRNA and the arrow on the low molecular weight side (low m/z side) indicates a non-acylated μhRNA. The terms "Calcd." and "Obsd." have the same meanings as those in FIG. 4 and * and t indicate a sodium adduct and a potassium adduct, respectively.

FIG. 20 shows the tricine SDS-PAGE analysis results of Abz derivative-containing rP1 peptides in FIG. 12*c*.

FIG. 21 shows the tricine SDS-PAGE analysis results of Abz-containing peptides (rP1 to rP4) in FIG. 13*b*.

DESCRIPTION OF EMBODIMENTS

Embodiments of the present invention will hereinafter be described in detail. The present invention is not limited by the following embodiments, but can be performed by modifying in various ways without departing from the gist of the invention.

<Method of Producing a Library>

The present invention relates to a method of producing a library including two or more cyclic peptides.

At least one of the cyclic peptides included in the library of the present invention is a cyclic peptide having a cyclic structure composed of 4 to 30 amino acids or derivatives thereof and containing at least one selected from cyclic β-, γ-, and δ-amino acids (cAAs) in the cyclic structure.

One of the methods of producing a library according to the present invention includes a step of preparing an mRNA library encoding a peptide having a sequence represented by the following formula (1);

$$-(Xaa)_{n1}- \quad (1)$$

[in the formula (1),

Xaas are each an arbitrary amino acid or derivative thereof, at least one of Xaas is one selected from cyclic β-, γ-, and δ-amino acids (cAAs), and n1 is an integer of 2 to 28]; and a step of using the mRNA library to express a peptide in a cell-free translation system and produce the library.

Another one of the methods of producing a library according to the present invention includes:

a step of preparing an mRNA library encoding a peptide having a sequence represented by the following formula (1);

$$-(Xaa)_{n1}- \quad (1)$$

[in the formula (1),

Xaas are each an arbitrary amino acid or derivative thereof, at least one of Xaas is one selected from cyclic β-, γ-, and δ-amino acids (cAAs), and n1 is an integer of 2 to 28];

a step of binding puromycin to the 3' end of each of mRNAs of the mRNA library to produce a puromycin-bound mRNA library; and a step of using the puromycin-bound mRNA library to express the precursor peptide in a cell-free translation system and produce a peptide-mRNA complex library.

When a peptide chain has a β-amino acid residue or γ-amino acid residue therein, their stable helical propensities make it possible to form unique rigid folding structures. Further, a β-amino acid can induce a turn structure of a peptide such as γ-turn or β-turn. In particular, cyclic β- and γ-amino acids (may also be called cβAA and cγAA) act as a particularly strong helix/turn inducer. If cyclic β- or γ-amino acid is introduced into a cyclic peptide, there is a possibility of causing the peptide to express rigidity. By the method of producing a library according to the present invention, a cyclic peptide containing a cyclic amino acid such as cyclic β- or γ-amino acid can be obtained.

The present inventors have newly found that ribosomal synthesis can be applied even to a cyclic amino acid which is a non-natural β- or γ-amino acid and at the same time, has a bulky and rigid structure.

The term "cyclic peptide" as used herein means a peptide at least having, in the molecule thereof, a cyclic structure composed of four or more amino acids. The cyclic peptide may have, as its molecular structure, a chain structure in which amino acids are linked to each other via a peptide bond, as well as the cyclic structure. It may also have a structure other than a peptide structure.

The term "cyclic structure" as used herein means a closed ring structure of a linear peptide formed in the molecule by two amino acids separated by 2 or more amino acid residues.

The term "separated by 2 or more amino acid residues" as used herein means that at least 2 amino acid residues are present between the two amino acids.

The term "library" as used herein means a group of cyclic peptides including two or more cyclic peptides.

The cyclic peptide in the present invention contains at least one of cAAs, more specifically, cyclic β-amino acids (cβAAs), cyclic γ-amino acids (cγAAs), and cyclic δ-amino acids (cδAAs). The cyclic peptide in the present invention may further contain, in addition to a natural amino acid (which may also be called "amino acid", simply), an artificial amino acid variant and/or derivative thereof (which may also be called "derivative of an amino acid").

Examples of the amino acid constituting the cyclic peptide in the present invention include natural proteinogenic L-amino acids, non-natural amino acids, and chemically synthesized compounds having properties which are characteristics of an amino acid and known in the art.

The proteinogenic amino acids are, when expressed by a three-letter code known in the art, Arg, His, Lys, Asp, Glu, Ser, Thr, Asn, Gln, Cys, Gly, Pro, Ala, Ile, Leu, Met, Phe, Trp, Tyr, and Val. The proteinogenic amino acids are, when expressed by a one-letter code known in the art, R, H, K, D, E, S, T, N, Q, C, G, P, A, I, L, M, F, W, Y, and V.

The term "non-proteinogenic amino acids" means natural or non-natural amino acids other than the proteinogenic amino acids.

Examples of the non-natural amino acids include α,α-disubstituted amino acids (such as α-methylalanine), N-alkylamino acids, D-amino acids, β-amino acids (β-amino acids here are amino acids other than cβAA), and α-hydroxy acids, each having a main chain structure different from that of natural amino acids; amino acids (such as norleucine and homohistidine) having a side-chain structure different from that of natural amino acids; amino acids (such as "homo" amino acids, homophenylalanine, and homohistidine) having extra methylene in the side chain thereof; and amino acids (such as cysteic acid) obtained by substituting a carboxylic acid functional group in the side chain thereof by a sulfonic acid group. Specific examples of the non-natural amino acid include amino acids described in WO2015/030014.

Preferred examples of derivatives of amino acids in the present invention include N-alkyl-α-amino acids, which are amino acids having an alkyl group bound to the amino group at α-position.

The number of the amino acid residues forming the cyclic structure is not particularly limited as long as it is 4 or more and the number may be, for example, 5 or more, 6 or more, 7 or more, 8 or more, 9 or more, 10 or more, 11 or more, or 12 or more. The number of the amino acid residues forming the cyclic structure is not particularly limited as long as it is 30 or less and the number may be 25 or less, 20 or less, 18 or less, 17 or less, 16 or less, or 15 or less.

The number of amino acids forming the cyclic structure is usually 5 or more and 30 or less. Within a range of 5 or more and 30 or less, the number of amino acids forming the cyclic structure may be limited to 6 or more, 8 or more, 10 or more, 11 or more, or 12 or more and 30 or less, 25 or less, 20 or less, 18 or less, 17 or less, or 15 or less. By adjusting the number of amino acids forming the cyclic structure to a range of 5 or more and 30 or less, the diversity of the cyclic peptides constituting a library tends to be secured.

The number of amino acids forming the cyclic structure may be 8 or more and 20 or less, 8 or more and 17 or less, 9 or more and 17 or less, 10 or more and 15 or less, or 10 or more and 13 or less.

The number of amino acids forming the cyclic structure is preferably 9 or more and 25 or less, more preferably 10 or more and 20 or less, still more preferably 10 or more and 18 or less from the standpoint of functionality such as expression of a folded structure of the cyclic peptide.

The number of amino acids forming the cyclic structure may be 11 or more and 17 or less, 12 or more and 18 or less, 12 or more and 18 or less, or 11 or more and 16 or less.

In the present invention, the cyclic peptide may be a modified one such as phosphorylated, methylated, acetylated, adenylated, ADP-ribosylated, glycosylated, or polyethylene glycol-added one or it may be a fused one with another peptide and/or protein. Further, the cyclic peptide may be a biotinylated or labeled one via an appropriate linker.

In the present invention, the cyclic peptide may also be a dimer having in the molecule thereof two cyclic structures and obtained by binding two cyclic peptides, each having one cyclic structure, to each other via a linker structure or it may have an intramolecular lactam bridge structure obtained by intramolecularly forming a lactam structure.

The linker structure that links two cyclic peptides to each other is not particularly limited and a structure known in a peptide synthesis field as a linker that links peptides to each other may be used.

The intramolecular lactam bridge structure may be formed by binding the respective side chains of amino acids constituting the cyclic peptide. For example, an intramolecular lactam structure is formed by binding the side chain amino group of Lys to the side-chain carboxyl group of Asp or Glu to form a peptide bond and thereby form an intramolecular lactam structure. The cyclic peptide has, in the molecule thereof, another cyclic structure as a bridge structure. Instead of Lys, for example, DAP, DAB, and Orn may be bound to Asp or Glu.

The cAA in the present invention may be represented, for example, by the following formula (I).

[Chemical formula 15]

(I)

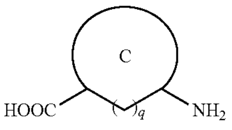

In the formula (I), the ring C may be a saturated or unsaturated alicyclic hydrocarbon ring or a heterocyclic ring. The ring C may also be an aromatic ring. Further, the ring C may have a crosslinked structure.

In the formula, q is any integer of 0, 1, or 2. When q is 0, the carbon to which the carboxylic acid group is bound and the carbon to which the amino group is bound form a single bond.

In order to perform smooth introduction into a cyclic peptide by ribosomal synthesis, the ring C is preferably a saturated or unsaturated alicyclic hydrocarbon ring or an aromatic ring, more preferably a saturated or unsaturated alicyclic hydrocarbon ring.

The cβAA in the present invention is preferably represented by the following formula (I-1).

[Chemical formula 16]

(I-1)

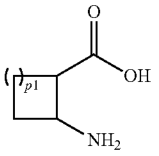

In the formula (I-1), p1 is any integer of 1 to 4, preferably any integer of 1 to 3.

In the present invention, cγAA is preferably represented by the following formula (I-2).

[Chemical formula 17]

(I-2)

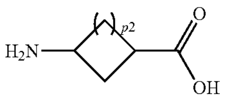

In the formula (I-2), p2 is any integer of 1 to 4, preferably any integer of 1 to 3.

The cδAA in the present invention is preferably represented by the following formula (I-3).

[Chemical formula 18]

(I-3)

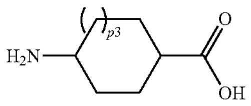

In the formula (I-3), p3 is an integer of 1 or 2, preferably 1.

The cAA such as cβAA, cγAA, or cδAA in the present invention is preferably represented by the following formula (I-4).

$$H_2N—Ar—COOH \quad (I-4)$$

In the formula (I-4), Ar is a divalent aromatic group and the aromatic ring in the aromatic group may be a substituted one with one or more substituents.

Here, the term "Ar is a divalent aromatic group" means that the ring C is an aromatic ring and one of the two binding hands of the aromatic ring binds to an amino group ($NH_2$) and the other one of the two binding hands binds to a carboxyl group (COOH).

The two binding hands of the aromatic ring bind to at least to $NH_2$ and COOH, but the remaining binding hands may bind to a hydrogen atom or may bind to one or more substituents.

The aromatic ring may be benzene, naphthalene, or the like, or may be an aromatic heterocyclic ring composed of one or more nitrogen atoms, oxygen atoms, and/or sulfur atoms and carbon atoms.

When the aromatic ring is an aromatic heterocyclic ring, it may be a 5 or 6-membered aromatic heterocyclic compound containing one or more nitrogen atoms, oxygen atoms, and/or sulfur atoms, such as pyridine, pyrimidine, imidazole, oxazole, thiazole, furan, pyran, and thiophene. Alternatively, it may be a fused ring compound such as indole, quinoline, isoquinoline, benzothiophene, or benzofuran.

When the aromatic ring has one or more substituents, the number of the substituents may be 1, 2, 3, or 4, may be 1 to 3, may be 1 or 2, or may be 1.

The substituent is not particularly limited, and examples thereof include linear or branched alkyl groups, alkenyl groups or alkynyl groups, each having 1 to 6 carbon atoms, a hydroxyl group, an amino group, a halogen (fluorine, chlorine, bromine, or iodine), and linear or branched alkoxy groups, alkenyl groups, or alkynyl groups, each having 1 to 6 carbon atoms.

The aromatic ring is not particularly limited and it may be a 5-membered or 6-membered ring.

When the aromatic ring is a 6-membered ring, that having $NH_2$ and COOH at the ortho position is cβAA, that having them at the meta position is cγAA, and that having them at the para position is cδAA. In other words, when the aromatic ring is a 6-membered ring, that having $NH_2$ and COOH at position 1 and position 2, it is cβAA, that having them at position 1 and position 3 is cγAA, and that having them at position 1 and position 4 is cδAA.

When the aromatic ring is a 5-membered ring, that having $NH_2$ and COOH at position 1 and position 2, it is cβAA and that having them at position 1 and position 3 is cγAA.

The ribosomal incorporation of 2-aminobenzoic acid (Abz) which is a kind of an aromatic amino acid has been achieved only at the N terminal of a peptide, but the present invention makes it possible to achieve ribosomal elongation even if an aromatic amino acid is incorporated in a non-N-terminal site. In other words, the present invention makes it possible to incorporate, as a structural unit during the elongation, an aromatic amino acid into a peptide chain.

The cyclic peptide in the production method according to the present invention contains a sequence represented by the following formula (1);

$$-(Xaa)_{n1}- \quad (1).$$

In the formula (1),

Xaas are each an arbitrary amino acid or derivative thereof, at least one of Xaas is one selected from cyclic β-, γ-, and δ-amino acids (cAAs), and n1 is an integer of 2 to 28.

The cAA in the present invention is more preferably selected from the following structures.

[Chemical formula 19]

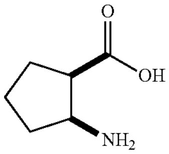
(1R,2S)-2-ACPC

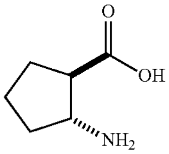
(1R,2R)-2-ACPC

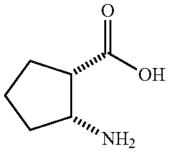
(1S,2R)-2-ACPC

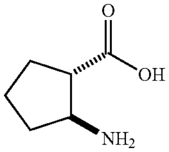
(1S,2S)-2-ACPC

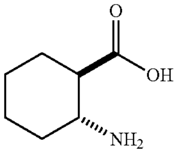
(1R,2R)-2-ACHC

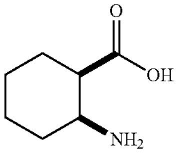
(1R,2S)-2-ACHC

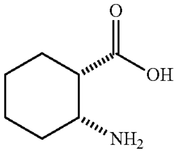
(1S,2R)-2-ACHC

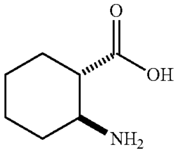
(1S,2S)-2-ACHC

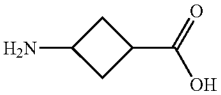
cis-3-ACBC

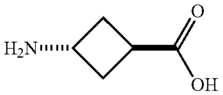
trans-3-ACBC

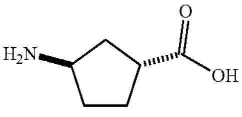
(1R,3R)-3-ACPC

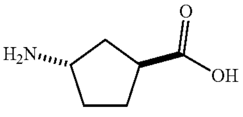
(1S,3S)-3-ACPC

-continued

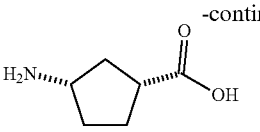
(1R,3S)-3-ACPC

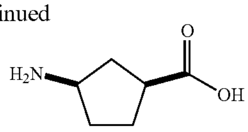
(1S,3R)-3-ACPC

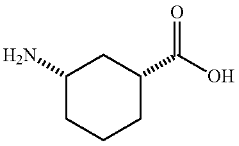
(1R,3S)-3-ACHC

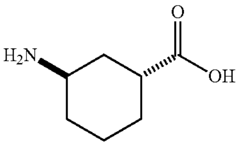
(1R,3R)-3-ACHC

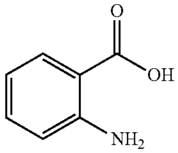
2-Aminobenzoic acid (Abz)

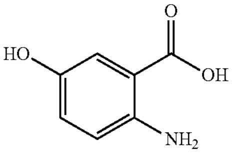
2-Amino-5-hydroxy benzoic acid ($Abz^{5OH}$)

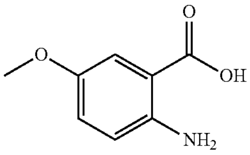
2-Amino-5-methoxy benzoic acid ($Abz^{5OMe}$)

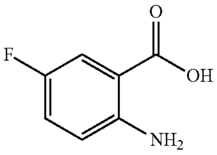
2-Amino-5-fluoro benzoic acid ($Abz^{F}$)

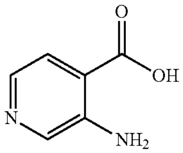
3-Aminopyridine-4-carboxylic acid (Apy)

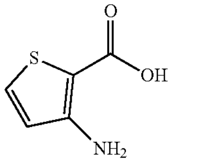
3-Aminothiophene-2-carboxylic acid (Alp)

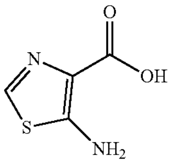
5-Aminothiazole 4-carboxylic acid (Atz)

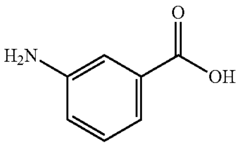
3-Aminobenzoic acid ($^{CN}Abz$)

Although the closed ring structure of the cyclic peptide in the present invention is not particularly limited, it is formed by the covalent bonding of two amino acids.

Examples of the covalent bonding between two amino acids include disulfide bonding, peptide bonding, alkyl bonding, alkenyl bonding, ester bonding, thioester bonding, ether bonding, thioether bonding, phosphonate ether bonding, azo bonding, C—S—C bonding, C—N—C bonding, C═N—C bonding, amide bonding, lactam bridging, carbamoyl bonding, urea bonding, thiourea bonding, amine bonding, and thioamide bonding.

When two amino acids bind to each other in their main chain, a closed ring structure is formed by peptide bonding. A covalent bond between two amino acids may be formed by bonding between the respective side chains of the two amino acids, bonding between the side chain and the main chain of them, or the like.

The cyclic structure is not limited to that formed by bonding between the N-terminal and C-terminal amino acids of a linear peptide, but it may be formed by bonding between a terminal amino acid and a non-terminal amino acid or bonding between non-terminal amino acids. When one of the amino acids bound for the formation of a cyclic structure is a terminal amino acid and the other one is a non-terminal amino acid, the resulting cyclic peptide has a cyclic structure having a linear peptide attached thereto like a tail.

As the closed ring structure, a peptide translationally synthesized can be cyclized by a spontaneous reaction, for example, by incorporating an amino acid having the following Functional group 1 and Functional group 2 corresponding thereto as ring-forming amino acids. Either Functional group 1 or Functional group 2 may be placed on the N terminal side or they may be placed at the N terminal and C terminal, respectively. As to the position of Functional group 1 and Functional group 2, one of them may be placed as a terminal amino acid and the other one may be placed as a non-terminal amino acid, or both may be placed as a non-terminal amino acid.

TABLE 1

| | Functional group1 | | Functional group2 | |
|---|---|---|---|---|
| (A) | 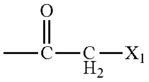 | (A-1) | HS— | (A-2) |
| (B) | —C≡C—H | (B-1) | $N_3$— | (B-2) |
| (C) | —Ar—$CH_2NH_2$ | (C-1) | 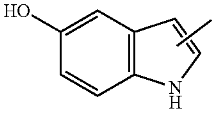 | (C-2) |
| (D) | —C≡C—$CH_2$—$X_1$ | (D-1) | HS— | (D-2) |
| (F) | —Ar—$CH_2$—$X_1$ | (E-1) | HS— | (E-2) |

The cyclic peptide in the present invention is preferably represented by the following formula (2). In the production method according to the present invention, it is therefore preferred to use an mRNA library encoding the peptide represented by the formula (2).

$$Xaa1\text{-}(Xaa)_{n1}\text{-}Xaa2\text{-}(Xaa_x)_m \quad (2)$$

In the formula (2),

Xaas are each an arbitrary amino acid or derivative thereof, at least one of Xaas is one selected from cyclic β-, γ-, and δ-amino acids (cAAs), Xaa1 and Xaa2 are each an amino acid or derivative thereof which forms the ring of a cyclic peptide, $Xaa_x$ is an arbitrary amino acid or derivative thereof, n1 is an integer of 2 to 28, and m is an integer of 0 to 10.

Between Xaa1 and Xaa2, it is preferred to form the aforesaid covalent bond such as disulfide bond, peptide bond, alkyl bond, alkenyl bond, ester bond, thioester bond, ether bond, thioether bond, phosphonate ester bond, azo bond, C—S—C bond, C—N—C bond, C═N—C bond, amide bond, lactam bridge, carbamoyl bond, urea bond, thiourea bond, amine bond, and thioamide bond. Of these bonds, thioether bond is more preferred.

When a thioether bond is formed between Xaa1 and Xaa2, Xaa1 is preferably N-chloroacetylphenylalanine ($^{ClAc}$Phe) or N-chloroacetyltyrosine ($^{ClAc}$Tyr), more preferably N-chloroacetyl-D-phenylalanine ($^{ClAc}$D-Phe) or N-chloroacetyl-D-tyrosine ($^{ClAc}$D-Tyr) and Xaa2 is preferably cysteine, more preferably D-cysteine (D-Cys).

When a thioether bond is formed between Xaa1 and Xaa2, the cyclic peptide in the present invention is preferably represented by the following formula (2').

[Chemical formula 20]

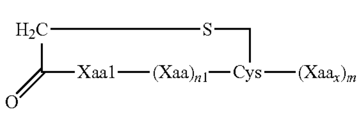

(2')

In the formula (2'),

Xaas are each an arbitrary amino acid or derivative thereof and at least one of Xaas is one selected from cyclic β-, γ-, and δ-amino acids (cAAs), Xaa1 is preferably phenylalanine or tyrosine, $Xaa_x$ is an arbitrary amino acid or derivative thereof, n1 is an integer of 2 to 28, and m is an integer of 0 to 10.

In the production method of the present invention, the peptide having a sequence represented by the formula (1) is expressed from an mRNA library encoding peptides having the sequence represented by the formula (1) by using a cell-free translation system. The mRNA library may be obtained from a commercially available product or may be prepared. For example, when the mRNA library is prepared, it may be prepared by obtaining a DNA library in accordance with the method described in Chemistry & Biology 18, 1562-1570 (2011) and/or Chemistry & Biology 21, 766-774 (2014) and transcribing the DNA library in vitro.

The mRNA library includes an mRNA having a plurality of N1N2N3s as a codon.

The term "N1N2N3" as used herein means a codon designating an arbitrary amino acid and for example, N1, N2, and N3 are independently selected from adenine (A), guanine (G), cytosine (C), and uracil (U). One mRNA contains a plurality of N1N2N3s and N1, N2, and N3 are each independently selected from them. For example, when mRNA contains -N1N2N3-N1N2N3-, therefore, these two N1s, N2s, or N3s may be the same or different from each other.

In the present invention, since the mRNA library encoding the peptide having the sequence represented by the formula (1): -(Xaa)n1- is used, it preferably contains at least an mRNA represented by -(N1N2N3)n1-.

In the present invention, an arbitrary amino acid is reassigned to N1N2N3, but a cAA is reassigned to at least one N1N2N3. In the reassignment, an amino acid different from an amino acid having a codon-amino acid relation in a natural genetic code table may be assigned or an amino acid having the same relation may be assigned. The term "natural genetic code table" as used herein means a table showing amino acids represented by genetic codes composed of an mRNA triplet, respectively, in a living body. In the natural genetic code table, N1N2N3 represents the following amino acids.

TABLE 2

| | U | C | A | G | |
|---|---|---|---|---|---|
| U | Phe | Ser | Tyr | Cys | U |
| | Phe | Ser | Tyr | Cys | C |
| | Leu | Ser | STOP | STOP | A |
| | Leu | Ser | STOP | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

The mRNA library may include an mRNA containing, as a plurality of N1N2N3s, for example, any of a plurality of N1N2Ks, a plurality of N1N2Ss, a plurality of N1N2Ms, a plurality of N1N2Ws, a plurality of N1N2As, a plurality of N1N2Us, a plurality of N1N2Cs, and a plurality of N1N2Gs. The respective terms "N1" and "N2" as used herein have the same meanings as described above and Ks are independently either of uracil (U) or guanine (G), Ss are independently either of cytosine (C) or guanine (G), Ms are independently either of adenine (A) or cytosine (C), and Ws are independently either of adenine (A) or uracil (U).

For convenience' sake, the present invention will hereinafter be described using, as an example, the case where the mRNA library includes an mRNA containing a plurality of N1N2Ks, that is, the case where the mRNA library includes an mRNA containing, as N1N2N3, a plurality of N1N2Ks as a codon. Even if another mRNA library is used, it is possible to carry out the invention similarly insofar as a peptide contained in the translated peptide library is prenylated. In the natural genetic code table, N1N2K corresponds to 20 amino acids when the code in the right column in the above table is G or U.

In the present specification, for example, Leu is assigned to UUG as shown in the natural genetic code table or an amino acid other than Leu may be assigned by the reassignment of a codon. Any amino acid may be assigned to a "N1N2K" codon. The term "assigning an amino acid to a codon" means that the genetic code table is rewritten so that a certain codon encodes the amino acid. The term "assigning an amino acid to a codon" as used herein has the same meaning as "reassigning a codon".

Assignment, to each codon, of an amino acid different from that in the natural genetic code table is achieved, for example, by codon reassignment making use of artificial aminoacylated RNA catalyst flexizyme (Flexizyme). By Flexizyme, a desired amino acid can be bound to a tRNA having an arbitrary anticodon, so that an arbitrary amino acid can be assigned to an arbitrary codon. Flexizyme will be described later. In the present specification, "binding an amino acid to tRNA" may also be expressed as "charging tRNA with an amino acid", "aminoacylating tRNA", or "acylating tRNA with an amino acid".

In the present invention, cAA is assigned to "N1N2K" or a nonproteinogenic amino acid other than a cAA may be assigned to it. When mRNA contains two or more "N1N2Ks", all of them may be assigned to a cAA or nonproteinogenic amino acid or some of them may be assigned to a cAA or nonproteinogenic amino acid.

The term "cell-free translation system" as used herein means a translation system not containing cells. More specifically, it is a system of synthesizing an intended peptide or protein in a test tube by making use of the synthesizing function of a protein extracted from cells. As the cell-free translation system, for example, an *Escherichia coli* extract, a wheat germ extract, a rabbit reticulocyte extract, or an insect cell extract may be used. Alternatively, a reconstituted cell-free translation system may be used, which is obtained by reconstituting a purified ribosome protein, aminoacyl-tRNA synthase (aaRS), ribosomal RNA, amino acid, rRNA, GTP, ATP, translation initiation factor (IF), elongation factor (EF), release factor (RF), and ribosome recycling factor (RRF), and another factor necessary for translation. The system may contain RNA polymerase for simultaneously performing transcription from DNA. Examples of a commercially available cell-free translation system include *Escherichia-coli* derived systems such as "RTS-100" (trade mark) of Roche Diagnostics, reconstituted translation systems such as "PURESYSTEM" (trade mark) of PGI and "PURExpressR In Vitro Protein Synthesis Kit" of New England BioLabs, and systems using a wheat germ extract such as those of ZOEGENE Corporation or CellFree Sciences.

As a system using a ribosome of *Escherichia coli*, for example, a technology described in the following documents is known: H. F. Kung et al., 1977. The Journal of Biological Chemistry Vol. 252, No. 19, 6889-6894; M. C. Gonza et al., 1985, Proceeding of National Academy of Sciences of the United States of America Vol. 82, 1648-1652; M. Y Pavlov and M. Ehrenberg, 1996, Archives of Biochemistry and Biophysics Vol. 328, No. 1, 9-16; Y Shimizu et al., 2001, Nature Biotechnology Vol. 19, No. 8, 751-755; and H. Ohashi et al., 2007, Biochemical and Biophysical Research Communications Vol. 352, No. 1, 270-276. By using the cell-free translation system, a high-purity expression product can be obtained without purifying. The cell-free translation system of the present invention may be used not only for translation, but also for transcription after adding a factor necessary for transcription.

In the present invention, peptide expression by the cell-free translation system may be performed using Flexible In vitro Translation system (FIT system), for example, in accordance with the method described in Goto, Y, Katoh, T. & Suga, H. Flexizymes for genetic code reprogramming. Nat Protoc 6, 779-790, (2011).

The cell-free translation system in the present invention preferably contains a tRNA charged with a cAA to obtain a cyclic peptide containing a cAA.

The present inventors studied a method of introducing a cAA into a cyclic peptide by ribosomal synthesis. As a result, it has been found that a cyclic peptide containing a cAA can be obtained efficiently by selecting a tRNA to be charged, depending on the kind of a cAA, and using the tRNA charged with the cAA.

As a tRNA to be charged with a cAA, a tRNA having a D-arm structure interactive with EF-P, which is a translation factor, or a tRNA not having a D-arm structure interactive with EF-P can be used. As a tRNA to be charged with a cAA, either of the aforesaid tRNAs may be used but it may be selected as needed depending on the kind of a cAA. The cell-free translation system in the present invention therefore preferably contains a tRNA charged with one selected from cyclic β-, γ-, and δ-amino acids (cAAs) and having a D-arm structure interactive with EF-P or a tRNA similarly charged and not having a D-arm structure interactive with EF-P.

As the tRNA having a D-arm structure interactive with EF-P, for example, the tRNA described in WO2019/077887 may be used.

Specific examples of the tRNA having a D-arm structure interactive with EF-P include a tRNA having a base sequence of $N_1N_2GCN_3N_4N_5N_6N_7N_8N_9N_{10}N_{11}GCN_{12}N_{13}$ (SEQ ID NO: 1), in which $N_1$ to $N_{13}$ are each an arbitrary base, $N_3$ to $N_{11}$ form a D-loop, and $N_1N_2GC$ forms a base pair with $N_{13}N_{12}CG$. Any base can be selected insofar as $N_1N_2$ and $N_{12}N_{13}$ form a base pair, but it is preferred that $N_1$ is G and $N_{13}$ is C.

In addition, it is preferred that $N_2$ is C and $N_{12}$ is G.

The base sequence represented by SEQ ID NO: 1 is a D-arm comprised of a D-loop and a D-stem and the introduction of the base sequence represented by SEQ ID NO: 1 into a tRNA tends to promote peptidyl transfer by EF-P peptide.

Another structure of the tRNA having the base sequence represented by SEQ ID NO: 1, that is, the base sequence of an acceptor stem, an anticodon stem, an anticodon loop, a variable loop, or a T-arm is arbitrary. The anticodon loop may have a base sequence corresponding to a codon to which a cAA is assigned. The 3' end of the tRNA has a CCA sequence and binds to a cAA.

The base sequence represented by SEQ ID NO: 1 is preferably a base sequence represented by SEQ ID NO: 3.

(SEQ ID NO: 3)
$GCGC\mathbf{N_3N_4N_5N_6N_7N_8N_9N_{10}N_{11}}GCGC$

In SEQ ID NO: 3, $N_3$ to $N_{11}$ have the same meanings as described above and GCGC forms a base pair with CGCG.

The base sequence of $N_3$ to $N_{11}$ in SEQ ID NO: 1 and SEQ ID NO: 3 is preferably a base sequence represented by SEQ ID NO: 4.

(SEQ ID NO: 4)
AGCCUGGUA

The base sequence represented by SEQ ID NO: 4 forms a D-loop in the tRNA.

In SEQ ID NO: 4, one or a plurality of bases may be substituted.

The term "a plurality of bases may be substituted" means that in 9 bases forming a D-loop, 2, 3, 4, 5, 6, 7, 8, or 9 bases may be substituted, 1 to 4 bases may be substituted, 1 to 3 bases may be substituted, 1 to 2 bases may be substituted, or 1 base may be substituted.

The base sequence represented by SEQ ID NO: 1 is preferably a base sequence represented by SEQ ID NO: 5 and is preferably a base sequence represented by SEQ ID NO: 6.

(SEQ ID NO: 5)
$\mathbf{N_1N_2}GCGCAGCCUGGUAGCGC\mathbf{N_{12}N_{13}}$

In SEQ ID NO: 5, $N_1$, $N_2$, $N_{12}$, and $N_{13}$ have the same meanings as described above and $N_1N_2GC$ forms a base pair with $N_{13}N_{12}CG$.

(SEQ ID NO: 6)
GCGCGCAGCCUGGUAGCGCGC

In SEQ ID NO: 5 and SEQ ID NO: 6, one or a plurality of bases may be substituted. The term "in SEQ ID NO: 5 and SEQ ID NO: 6, a plurality of bases may be substituted" means that in SEQ ID NO: 4 which indicates 9 bases forming a D-loop, 2, 3, 4, 5, 6, 7, 8, or 9 bases may be substituted, 1 to 4 bases may be substituted, 1 to 3 bases may be substituted, 1 to 2 bases may be substituted, or 1 base may be substituted.

The tRNA having a D-arm structure interactive with EF-P and the tRNA not having a D-arm structure interactive with EF-P may both have a base sequence represented by SEQ ID NO: 2.

(SEQ ID NO: 2)
$AGGGG(\mathbf{N}_{14})_mCCCCU$

In SEQ ID NO: 2, N14 is an arbitrary base, m is an integer of 1 or more, (N14)m forms a T-loop, and AGGGG forms a base pair with UCCCC.

The T-stem of the aminoacyl-tRNA controls the interaction with EF-Tu protein and reinforces the incorporation of a nonproteinogenic amino acid. The base sequence represented by SEQ ID NO: 2 is a T-arm comprised of a T-loop and a T-stem and introduction of the base sequence represented by SEQ ID NO: 2 into a tRNA tends to promote accommodation by EF-Tu protein in introducing a cAA into a cyclic peptide.

Although m is not particularly limited insofar as (N14)m forms a T-loop, it may be an integer of 2, 3, 4, 5, 6, 7, 8, 9, or 10, preferably an integer of 6 to 8.

$(N_{14})_m$ is preferably a base sequence derived from the T-loop of $tRNA^{GluE2}$ and represented by SEQ ID NO: 7.

(SEQ ID NO: 7)
UUCGAAU

In SEQ ID NO: 7, 1 or a plurality of bases may be substituted. The term "a plurality of bases may be substituted" means that in 7 bases forming a T-loop, 2, 3, 4, 5, 6, or 7 bases may be substituted, 1 to 3 bases may be substituted, 1 to 2 bases may be sub substituted, or 1 base may be substituted.

In SEQ ID NO: 2, AGGGG and UCCCC forming a base pair form a T-stem. In the base sequence forming the T-stem, one or a plurality of bases may be substituted insofar as they form a base pair.

The term "a plurality of bases may be substituted" in the T-stem of SEQ ID NO: 2 means that in 10 bases forming the T-stem, 2, 3, 4, 5, 6, 7, 8, 9, or 10 bases may be substituted, 2 bases may be substituted, 4 bases may be substituted, or 6 bases may be substituted. Insofar as they form a base pair, 1, 3, or 5 bases may be substituted.

When the tRNA having a D-arm structure interactive with EF-P is used in the present invention, the tRNA preferably contains both the base sequence represented by SEQ ID NO: 1 and the base sequence represented by SEQ ID NO: 2 in order to allow an EF-P protein to exert a peptidyl transfer promotion effect and to allow an EF-Tu protein to exert an accommodation promotion effect.

The tRNA having a D-arm structure interactive with EF-P is preferably a chimera of $tRNA^{Pro1}$ and $tRNA^{GluE2}$ and such a tRNA will hereinafter be called "$tRNA^{Pro1E2}$"

More specifically, the tRNA having a D-arm structure interactive with EF-P preferably has the T-stem of $tRNA^{GluE2}$ introduced into $tRNA^{Pro1}$.

When the tRNA not having a D-arm structure interactive with EF-P is used, the tRNA preferably has the base sequence represented by SEQ ID NO: 2 in order to allow an EF-Tu protein to exert an accommodation promotion effect.

The tRNA not having a D-arm structure interactive with EF-P is preferably $tRNA^{GluE2}$.

Therefore, in one of preferred modes of a cell-free translation system in the method of producing a library according to the present invention, the cell-free system contains a tRNA charged with one selected from cyclic β-, γ-, and δ-amino acids (cAAs) and the tRNA is at least one selected from $tRNA^{Pro1E2}$ and $tRNA^{GluE2}$When the cAA is an aromatic amino acid, the tRNA is $tRNA^{Pro1E2}$ in a preferred mode.

In the tRNA having a D-arm structure interactive with EF-P and the tRNA not having a D-arm structure interactive with EF-P, a base sequence other than SEQ ID NO: 1 and/or SEQ ID NO: 2 may be derived from a wild-type tRNA, may be derived from an *Escherichia coli*-derived wild type tRNA, or an artificial tRNA prepared by the in vitro transcription.

The sequence represented by the formula (1) in the method of producing a library according to the present invention may contain at least one cAA selected from cyclic β-, γ-, and δ-amino acids.

When two or more cAAs are contained, two or more cAAs may be contained at random in the sequence represented by the formula (1) or two or more consecutive cAAs may be contained in the sequence represented by the formula (1). The term "two or more cAAs may be contained at random in the sequence represented by the formula (1)" as used herein means a mode in which at least two cAAs are contained at any position of the sequence of the formula (1) and these two or more cAAs are not adjacent to each other. Therefore, when two or more cAAs are contained at random, an amino acid or derivative thereof other than a cAA adjacently binds to each of these two or more cAAs.

When at least one cAA is contained in the sequence represented by the formula (1), the kind of the cAA is not particularly limited and a cAA represented by any of the formulas (I-1), (I-2), (I-3), and (I-4) is preferred, a cAA represented by either the formula (I-1) or (I-2) is more preferred, a cAA represented by the formula (I-4) is more preferred, and a cAA represented by the following structure is still more preferred. When two or more cAAs are contained at random in the sequence represented by the formula (1), the kind of the cAAs is not particularly limited and a cAA represented by any of the formulas (I-1), (I-2), (I-3), and (I-4) is preferred, a cAA represented by any of the formulas (I-1), (I-2), and (I-4) is more preferred, and a cAA represented by the following structure is still more preferred.

When two or more cAAs are contained at random, they may be any combination of the cAAs represented by the formulas (I-1), (I-2), (I-3), and (I-4). The combination may be that of two or more cAAs represented only by the formula (I-1), that of two or more cAAs represented only by the formula (I-2), that of two or more cAAs represented only by the formula (I-3), or that of two or more cAAs represented only by the formula (I-4).

[Chemical formula 21]

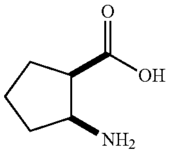

(1R,2S)-2-ACPC

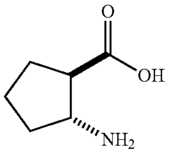

(1R,2R)-2-ACPC

-continued

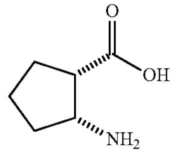

(1S,2R)-2-ACPC

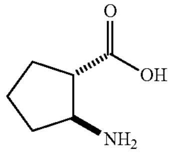

(1S,2S)-2-ACPC

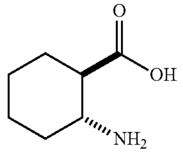

(1R,2R)-2-ACHC

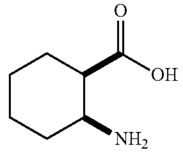

(1R,2S)-2-ACHC

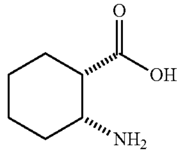

(1S,2R)-2-ACHC

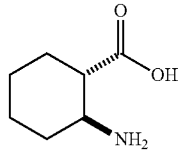

(1S,2S)-2-ACHC

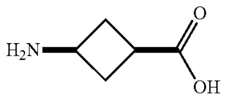

cis-3-ACBC

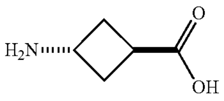

trans-3-ACBC

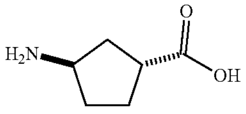

(1R,3R)-3-ACPC

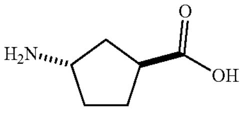

(1S,3S)-3-ACPC

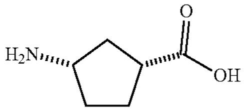

(1R,3S)-3-ACPC

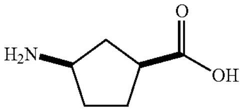

(1S,3R)-3-ACPC

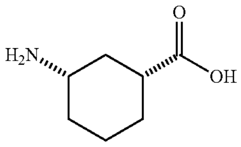

(1R,3S)-3-ACHC

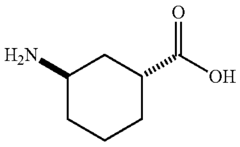

(1R,3R)-3-ACHC

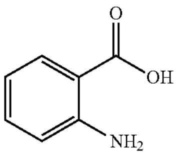

2-Aminobenzoic acid (Abz)

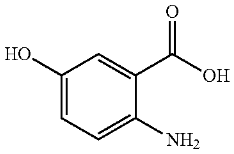

2-Amino-5-hydroxy benzoic acid ($Abz^{5OH}$)

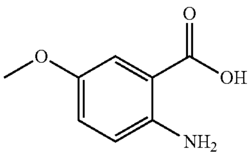

2-Amino-5-methoxy benzoic acid ($Abz^{5OMe}$)

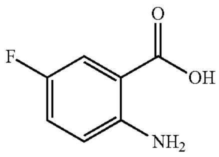

2-Amino-5-fluoro benzoic acid ($Abz^{F}$)

-continued

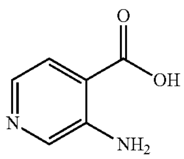

3-Aminopyridine-4-carboxylic acid (Apy)

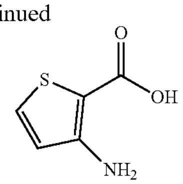

3-Aminothiophene-2-carboxylic acid (Alp)

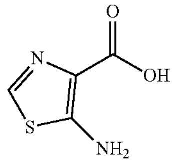

5-Aminothiazole 4-carboxylic acid (Atz)

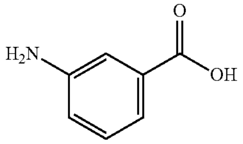

3-Aminobenzoic acid ($^{CN}$Abz)

When 2 or more consecutive cAAs are contained in the sequence represented by the formula (1), the kind of the two consecutive cAAs is not particularly limited and they are preferably any of the cAAs represented by the formula (I-1), (I-2), (I-3), and (I-4), more preferably any of the cAAs represented by the formula (I-1), (I-2), and (I-4), still more preferably the cAA represented by the formula (I-1), also still more preferably the cAA represented by the formula (I-4), and further more preferably the cAA represented by the following structure.

[Chemical formula 22]

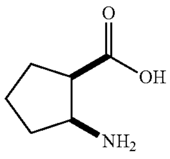

(1R,2S)-2-ACPC

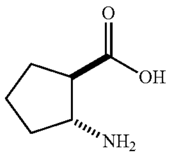

(1R,2R)-2-ACPC

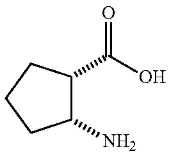

(1S,2R)-2-ACPC

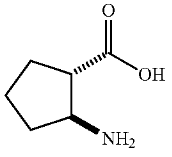

(1S,2S)-2-ACPC

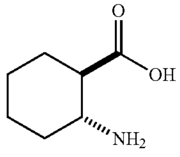

(1R,2R)-2-ACHC

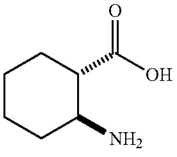

(1S,2S)-2-ACHC

When two or more consecutive cAAs are contained in the sequence represented by the formula (1) as described above, it is only necessary that at least one unit represented by -cAA-cAA- may be contained in the sequence represented by the formula (1) and another cAA may be contained. The other cAA contained in the sequence is not particularly limited and a preferred mode is the same as that in the case where two or more cAAs are contained at random in the sequence represented by the formula (1).

When two or more consecutive cAAs are contained in the sequence represented by the formula (1), the number of the consecutive cAAs is preferably 2.

When three or more consecutive cAAs are contained in the sequence represented by the formula (1), the cAAs are preferably a cAA represented by the formula (I-1), more preferably (1S,2S)-2-ACPC. By using (1S,2S)-2-ACPC as the cAAs, these cAAs tend to be consecutively incorporated in a peptide more efficiently. Since the folding of (1S,2S)-2-ACPC is expressed when the number of residues is 4 or so (refer to Kwon, S., Jeon, A., Yoo, S. H., Chung, I. S. & Lee, H. S. Unprecedented molecular architectures by the controlled self-assembly of a 3-peptide foldamer. Angew. Chem. Int. Ed. Engl. 49, 8232-8236 (2010) and Kim, J. et al. Microtubes with rectangular cross-section by self-assembly of a short β-peptide foldamer. J. Am. Chem. Soc. 134, 20573-20576, (2012)), it is presumed that particularly a peptide containing 4 or more consecutive (1S,2S)-2-ACPCs is folded into a helical structure. As described above, according to the present invention, a folded molecule can be synthesized biochemically.

When 3 or more consecutive cAAs are contained in the sequence represented by the formula (1), it is only necessary that at least one unit represented by -cAA-cAA-cAA- is contained in the sequence represented by the formula (1) and another cAA may be contained in the sequence. The other cAA contained in the sequence is not particularly limited and a preferred mode is similar to that in the case where two or more cAAs are contained at random in the sequence represented by the formula (1).

The (1S,2S)-2-ACPC is represented by the following formula.

[Chemical formula 23]

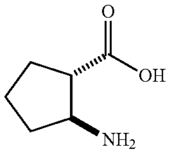

When three or more consecutive (1S,2S)-2-ACPCs are contained, the upper limit of the introduction number is not particularly limited and it is preferably 15 or less, more preferably 12 or less, still more preferably 10 or less.

As described above, a tRNA to be charged is preferably selected, depending on the kind of a cAA from the standpoint of efficiently introducing the cAA into a cyclic peptide.

The following cAA (which will hereinafter be called "cyclic β- or γ-amino acid (i)", collectively) is preferably charged onto the tRNA having a D-arm structure interactive with EF-P, more preferably charged onto $tRNA^{Pro1E2}$. In particular, the cAAs of the formula (I-4) (of these, particularly, Abz, $AbZ^{5OH}$, $AbZ^{5OMe}$, $AbZ^{5F}$, Apy, Atp, or Atz) are preferably charged onto the tRNA having a D-arm structure interactive with EF-P, more preferably charged onto $tRNA^{Pro1E2}$.

[Chemical formula 24]

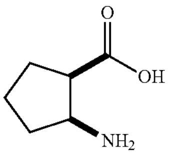

(1R,2S)-2-ACPC

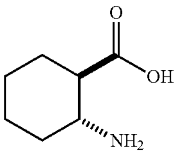

(1R,2R)-2-ACHC

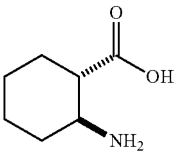

(1S,2S)-2-ACHC

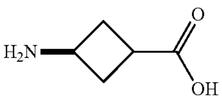

cis-3-ACBC

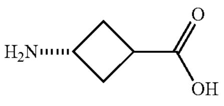

trans-3-ACBC

-continued

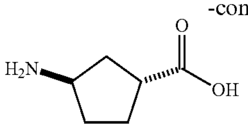

(1R,3R)-3-ACPC

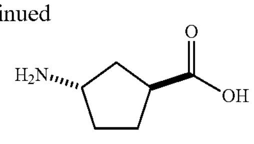

(1S,3S)-3-ACPC

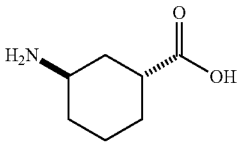

(1R,3R)-3-ACHC

The following cAA (which will hereinafter be called "cyclic β- or γ-amino acid (ii)", collectively) is preferably charged onto the tRNA not having a D-arm structure interactive with EF-P, more preferably charged onto $tRNA^{GluE2}$.

[Chemical formula 25]

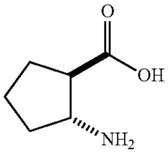

(1R,2R)-2-ACPC

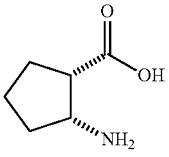

(1S,2R)-2-ACPC

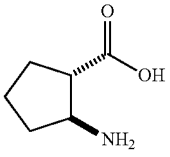

(1S,2S)-2-ACPC

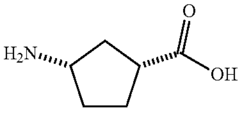

(1R,3S)-3-ACPC

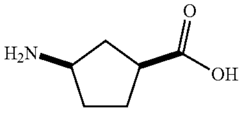

(1S,3R)-3-ACPC

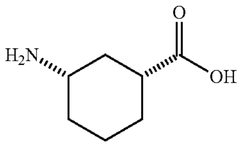

(1R,3S)-3-ACHC

The kind or concentration of components constituting the cell-free translation system in the present invention may be adjusted as needed.

For example, when the tRNA having a D-arm structure interactive with EF-P is used, more specifically, when the tRNA charged with the cyclic β- or γ-amino acid (i) or the cAA of the formula (I-4) and having a D-arm structure interactive with EF-P is used, the concentration of EF-P may be controlled to be larger than that in the case where such a tRNA is not used.

For example, when $tRNA^{Pro1E2}$ or $tRNA^{GluE2}$ is used, more specifically, when $tRNA^{Pro1E2}$ charged with the cyclic β- or γ-amino acid (i) or $tRNA^{GluE2}$ charged with the cyclic β- or γ-amino acid (ii) is used, the concentration of EF-Tu may be controlled to be larger than that in the case where such a tRNA is not used. When $tRNA^{Pro1E2}$ or $tRNA^{GluE2}$ is used, more specifically, when $tRNA^{Pro1E2}$ charged with the cyclic β- or γ-amino acid (i) or $tRNA^{GluE2}$ charged with the cyclic β- or γ-amino acid (ii) is used, the concentration of EF-G may be controlled to be smaller than that in the case where such a tRNA is not used. Controlling the respective concentrations of EF-Tu and EF-G as described above tends to make it possible to prevent the drop-off of a peptidyl-tRNA from a ribosome during translation.

In the aforesaid preferred combination of the tRNA and the amino acid to be charged with the tRNA, the tRNA charged with the amino acid can suitably be used for the synthesis of a peptide containing the amino acid. The peptide containing the amino acid can be produced suitably by using the tRNA charged with the amino acid.

The method of producing a library according to the present invention can be used for obtaining the cyclic peptide of the present invention which will hereinafter be described in detail. The sequence represented by the above formula (1) may be a sequence represented by the formula (3) or the formula (4) which will be described later (cAA is not limited to cβAA and it may be cγAA or cδAA. It is preferably cβAA and/or cγAA, more preferably cβAA).

<Cyclic Peptide>

The present invention relates to a cyclic peptide having a cyclic structure composed of 4 to 30 amino acids or derivatives thereof, or a pharmaceutically acceptable salt of the cyclic peptide, wherein two amino acids or derivatives thereof, of the 4 to 30 amino acids or derivatives thereof of the cyclic structure are Xaa1 and Xaa2; Xaa1 and Xaa contain a structure for forming the cyclic structure, Xaa1 and Xaa2 have a linked structure via an amino acid sequence composed of 2 to 28 amino acids or derivatives thereof; and the amino acid sequence composed of the 2 to 28 amino acids or derivatives thereof is composed of at least one selected from cyclic β-, γ-, and δ-amino acids (cAAs) and an arbitrary amino acid or derivative thereof.

In the present specification, a cyclic peptide and a pharmaceutically acceptable salt thereof may hereinafter be called "cyclic peptide" collectively and simply.

The cyclic peptide of the present invention containing a cAA can form a folded structure and has possibility of allowing a cyclic amino acid to express rigidity. In addition, the peptide of the present invention is highly stable to serum or the like, and in vivo degradation of it is suppressed. The degradation of the peptide of the present invention before it acts on a target protein is therefore presumed to be suppressed.

The cyclic peptide of the present invention can be obtained by the aforesaid <method of producing a library>. A cyclic peptide selected from the library and specified can be produced in an ordinary solid-phase synthesis method.

The definition, example, and mode of the "amino acid or derivative thereof", "Xaa1", "Xaa2", "cyclic β-, γ-, and δ-amino acids (cAAs)" in the cyclic peptide of the present invention are the same as the definition, example, and mode described in the aforesaid <method of producing a library> and a preferred mode is also the same as the aforesaid one.

<Cyclic Peptide Having Affinity for FXIIa>

One mode of the cyclic peptide of the present invention is a cyclic peptide represented by the following formula (3).

$$Xaa1\text{-}(Xaa)_{n1}\text{-}Xaa2\text{-}(Xaa_x)_m \quad (3)$$

In the formula (3),

Xaas are each an arbitrary amino acid or derivative thereof, at least one of Xaas is a cyclic β-amino acid (cβAA), Xaa1 and Xaa2 are amino acids or derivatives thereof forming the ring of the cyclic peptide, n1 is an integer of 10 to 16, $Xaa_x$ is an arbitrary amino acid or derivative thereof, and m is an integer of 0 to 10.

In the above formula, supposing that Xaa1 is the first amino acid, at least one cAA is present as the fifth to ninth one.

The cyclic peptide represented by the formula (3) has affinity for activated blood coagulation factor XII (which may also be called "FXIIa"). One provided by the present invention is a binding agent for FXIIa containing the cyclic peptide represented by the formula (3) or pharmaceutically acceptable salt thereof. The FXIIa is serine protease involved in the kallikrein-kinin system which contributes to coagulation and inflammation. An inhibitor against FXIIa is useful as an antithrombotic drug.

The cβAA in the formula (3) is preferably represented by the formula (I-1), more preferably (1S,2S)-2-ACHC and/or (1R,2R)-2-ACPC.

At least one of the Xaas in the formula (3) is preferably a basic amino acid or derivative thereof. The basic amino acid or derivative thereof described above is not particular limited insofar as it has an amino group on the side chain thereof. Examples include lysine, arginine, and histidine, and derivatives thereof. When at least one of the Xaas in the formula (3) is a basic amino acid or derivative thereof, an interaction of the cyclic peptide of the present invention to a binding site in FXIIa can be enhanced further and a stronger bond tends to be formed. This is presumed to occur because the basic amino acid or derivative thereof fits in an S1 pocket (refer to FIG. 10*b*) in FXIIa.

The (Xaa)n1 in the formula (3) is preferably any one selected from the following f1 to f4.

[Chemical formula 26]

-NDRSTR-cAA-RLVA- f1

-PRLFN-cAA-SYLRR- f2

-FAYDRR-cAA-LSNN-cAA-RNT- f3

-RYT-cAA-NRLF-cAA-NA- f4

In the formulas f1 to f4, the cAA is a cyclic β-amino acid.

The cyclic peptide represented by the formula (3) is preferably represented by the formula (3-1).

[Chemical formula 27]

(3-1)

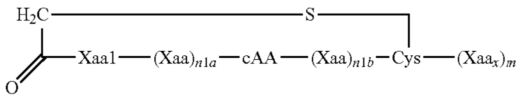

In the formula (3-1),

Xaas are each an arbitrary amino acid or derivative thereof, cAA is a cyclic β-amino acid, n1a is an integer of 3 to 7 and n1b is an integer of 2 to 8 (with the proviso that the sum of n1a and n1b is an integer of 9 to 15), $Xaa_x$ is an arbitrary amino acid or derivative thereof, Xaa1 is Phe or Tyr, and m is an integer of 0 to 10, with the proviso that $(Xaa)_{n1a}$ does not contain a cAA.

A difference (absolute value) between n1a and n1 b is preferably 4 or less.

The n1a may be an integer of 3 to 6 and n1 b may be an integer of 4 to 8 (with the proviso that in this case, the sum of n1a and n1 b is an integer of 9 to 14).

The cyclic peptide represented by the formula (3-1) is preferably any of the following F1 to F4.

[Chemical formula 28]

F1

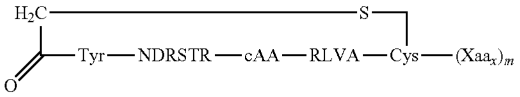

F2

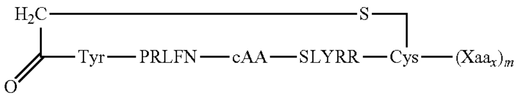

F3

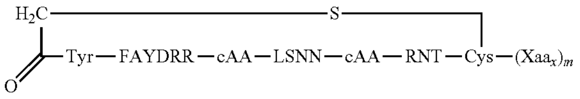

F4

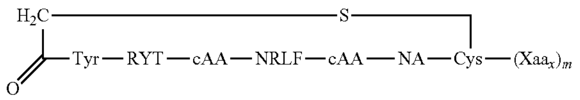

In the formulas F1 to F4, cAA, $Xaa_x$, and m have the same meanings as cAA, $Xaa_x$, and m in the formula (3-1).

<Cyclic Peptide Having Affinity for IFNGR1>

The cyclic peptide in one mode of the present invention is a cyclic peptide represented by the formula (4).

$$Xaa1\text{-}(Xaa)_{n1}\text{-}Xaa2\text{-}(Xaa_x)_m \quad (4)$$

In the formula (4),

Xaas are each an arbitrary amino acid or derivative thereof, at least one of the Xaas is a cyclic β-amino acid (cβAA), Xaa1 and Xaa2 are amino acids or derivatives thereof forming the ring of the cyclic peptide, n1 is an integer of 9 to 15, $Xaa_x$ is an arbitrary amino acid or derivative thereof, and m is an integer of 0 to 10.

In the above formula, supposing that the Xaa1 is a first amino acid, at least one cAA is present as the fourth to eighth one.

The cyclic peptide represented by the formula (4) has binding affinity for type II interferon receptor complex (which may also be called "IFNGR1"). The IFNGR1 is a receptor of an interferon-y(IFN-γ) which is a proinflammatory cytokine having an important role in inflammation and autoimmune diseases. An inhibitor against IFNGR1 is useful for the treatment of autoimmune diseases.

The cβAA in the formula (4) is preferably represented by the formula (I-1), more preferably any one or more selected from (1S,2S)-2-ACHC, (1R,2R)-2-ACPC, and (1S,2S)-2-ACPC.

The (Xaa)n1 in the formula (4) is preferably any one selected from the following i1-1 to i1-6.

[Chemical formula 29]

-FGVR-cAA-FYNRT- i1-1

-VGLN-cAA-SLNRT- i1-2

FSLR-cAA-SFNRSRG- i1-3

-FALN-cAA-R-cAA-NRR- i1-4

-FGV-cAA-cAA-FYNRT- i1-5

-PRYNL-cAA-GASPRF-cAA-N- i1-6

In the formulas i1-1 to i1-6, the cAA is a cyclic β-amino acid.

The cyclic peptide represented by the formula (4) is preferably represented by the following formula (4-1).

[Chemical formula 30]

(4-1)

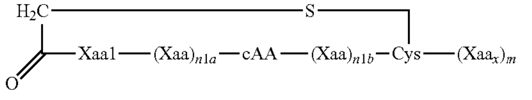

In the formula (4-1), Xaas are each an arbitrary amino acid or derivative thereof, cAA is a cyclic β-amino acid, n1a is an integer of 3 to 7 and n1b is an integer of 5 to 7 (with the proviso that the sum of n1a and n1b is an integer of 8 to 14), $Xaa_x$ is an arbitrary amino acid or derivative thereof, Xaa1 is Phe or Tyr, and m is an integer of 0 to 10, with the proviso that $(Xaa)_{n1a}$ does not contain cAA.

A difference (absolute value) between n1a and n1 b is preferably 4 or less.

n1a may be an integer of 3 to 5 and n1b may be an integer of 5 to 8 (with the proviso that in this case, the sum of n1a and n1 b is an integer of 8 to 13).

The cyclic peptide represented by the formula (4-1) is preferably any of the following I1-1 to I1-6.

[Chemical formula 31]

I1-1

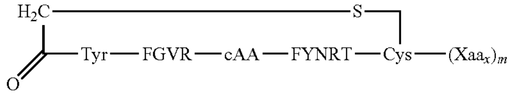

I1-2

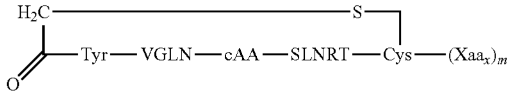

I1-3

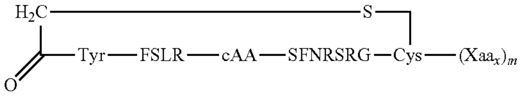

I1-4

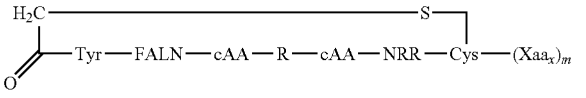

I1-5

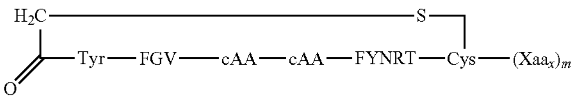

-continued

I1-6

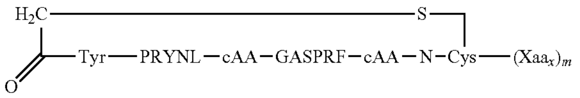

In the formulas I1-1 to I1-6, cAA, $Xaa_x$, and m have the same meanings as cAA, $Xaa_x$, and m in the formula (4-1).

The cyclic peptide of the present invention binds to FXIIa or IFNGR1 and inhibits its action. One provided by the present invention, therefore, is an FXIIa or IFNGR1 inhibitor containing the cyclic peptide of the present invention or pharmaceutically acceptable salt thereof. More specifically, one provided by the present invention is an FXIIa inhibitor containing the compound represented by the formula (3) or pharmaceutically acceptable salt thereof. In addition, one provided by the present invention is an IFNGR1 inhibitor containing the compound represented by the formula (4) or pharmaceutically acceptable salt thereof.

The binder or inhibitor of the present invention can be used as a pharmaceutical composition containing it.

The pharmaceutical composition of the present invention containing the FXIIa inhibitor can be used for the treatment or prevention of a disease related to blood clots. The pharmaceutical composition of the present invention containing the IFNGR1 inhibitor can be used for the treatment or prevention of a disease related to an autoimmune disease.

The administration route of the pharmaceutical composition is not particularly limited, and the composition may be either orally administered or parenterally administered. Examples of the parental administration include administration by injection such as intramuscular injection, intravenous injection or subcutaneous injection, percutaneous administration, and transmucosal administration. Examples of the administration route by the transmucosal administration include transnasal, transocular, transpulmonary, transvaginal and transrectal ones.

The cyclic peptide in the pharmaceutical composition may be subjected to various modifications from the standpoint of pharmacokinetics such as metabolism and/or excretion. For example, polyethylene glycol (PEG) and/or glycoside is added to the cyclic peptide to prolong the blood residence time and thereby lower the antigenicity.

The cyclic peptide may be encapsulated in an emulsion, nanoparticles, nanospheres, or the like used as a sustained-release base, which is/are prepared from a biodegradable high-molecular compound such as polylactic acid/glycol (PLGA), porous hydroxyapatite, liposome, surface-modified liposome, or unsaturated fatty acid. When it is administered percutaneously, it can be penetrated through the stratum corneum by passing a weak electrical current through the skin surface (iontophoresis).

The pharmaceutical composition may contain, as active ingredient, the cyclic peptide as is or it may be formulated by adding thereto a pharmaceutically acceptable additive and the like.

Examples of the dosage form of the pharmaceutical formulation include solutions (for example, injections), dispersions, suspensions, tablets, pills, powdered drug, suppositories, powders, fine granules, granules, capsules, syrups, troches, inhalants, ointments, ophthalmic formulations, nasal formulations, ear formulations, and cataplasms.

The pharmaceutical composition may be formulated in a conventional manner by using, for example, an excipient, a binder, a disintegrant, a lubricant, a dissolving agent, a solubilizing agent, a colorant, a taste/odor corrigent, a stabilizer, an emulsifier, an absorption promoter, a surfactant, a pH regulator, an antiseptic, a humectant, a dispersing agent, or an antioxidant as needed.

The additive used for the formulation is not particularly limited and examples include purified water, saline, phosphate buffer, pharmaceutically acceptable organic solvents such as dextrose, glycerol, and ethanol, animal or vegetable oils, lactose, mannitol, glucose, sorbitol, crystalline cellulose, hydroxypropyl cellulose, starch, corn starch, silicic anhydride, magnesium aluminum silicate, collagen, polyvinyl alcohol, polyvinylpyrrolidone, carboxy vinyl polymer, carboxymethylcellulose sodium, sodium polyacrylate, sodium alginate, water-soluble dextran, carboxymethyl starch sodium, pectin, methyl cellulose, ethyl cellulose, xanthan gum, gum arabic, tragacanth, casein, agar, polyethylene glycol, diglycerin, glycerin, polypropylene glycol, petrolatum, paraffin, octyl dodecyl myristate, isopropyl myristate, higher alcohol, stearyl alcohol, stearic acid, and human serum albumin.

As an absorption promoter in transmucosal absorption, surfactants such as polyoxyethylene lauryl ethers, sodium lauryl sulfate, and saponin; bile salts such as glycocholate, deoxycholate, and taurocholate; chelating agents such as EDTA and salicylic acid; fatty acids such as caproic acid, capric acid, lauric acid, oleic acid, linoleic acid, and mixed micelle; enamine derivatives, N-acylcollagen peptide, N-acylaminoic acid, cyclodextrines, chitosans, and nitric oxide donors may be used.

The tablets or pills may be sugar-, gastric-, or enteric-coated.

The solutions may contain distilled water for injection, physiological saline, propylene glycol, polyethylene glycol, a vegetable oil, an alcohol, or the like. The solutions may further contain a humectant, an emulsifier, a dispersant, a stabilizer, a dissolving agent, a solubilizing agent, an antiseptic, or the like.

The present invention also provides a method of administering the FXIIa inhibitor or IFNGR1 inhibitor to a patient who requires the inhibitor and thereby treating or preventing the disease of the patient.

The dose of the HGF inhibitor of the present invention is determined as needed by those skilled in the art, depending on the symptom, age, sex, weight, and difference in sensitivity of patients who require the inhibitor, the administration method, administration interval, and the type of the formulation.

The patient is a mammal, preferably a human being.

EXAMPLES

The tRNAs used in the present Examples were prepared by the following method.

(Preparation of tRNA)

Flexizymes (dFx and eFx) and tRNAs to be charged with 2-ACPC, 2-ACHC, $^{ClAc}$D-Phe, $^{ClAc}$D-Tyr, and D-Cys were prepared by the in vitro transcription using T7 RNA polymerase. Template DNAs for the transcription were prepared by the extension using a forward and reverse extension primer pair and the subsequent PCR using a forward and reverse PCR primer pair. Refer to Table 3 about the sequence of the primer.

The PCR products thus obtained were purified by phenol/chloroform extraction and ethanol precipitation. The template DNAs are composed of a T7 promoter at 5'-end and a downstream tRNA or flexizyme sequence. Refer to Table 3 about the sequence.

The transcription of RNA from the PCR product was performed at 37° C. for 16 hours in a 500 μL reaction mixture (a mixture of 40 mM Tris-HCl (pH 8.0), 22.5 mM $MgCl_2$, 1 mM DTT, 1 mM spermidine, 0.01% Triton X-100, 0.12 μM T7 RNA polymerase, 0.04 U/μL RNasin RNase inhibitor (Promega), and 3.75 mM NTP). For the transcription of the tRNA, 5 mM GMP or CMP was added to the above solution to start the transcription from G or C. The RNA transcripts thus obtained were subjected to DNase treatment at 37° C. for 30 minutes with RQ1 DNase (Promega) and then, purified using an 8% (in the case of the tRNA) or 12% (in the case of the flexizyme) polyacrylamide gel containing 6M urea. From top to bottom, the sequence identifiers of the RNA sequences in Table 3 are SEQ ID NOs: 8 to 18, respectively. From top to bottom, the sequence identifiers of the Extension primer (forward) in Table 3 are SEQ ID NOs: 19 to 29, respectively. From top to bottom, the sequence identifiers of the Extension primer (reverse) in Table 3 are SEQ ID NOs: 30 to 40, respectively. From top to bottom, the sequence identifiers of the PCT primer (forward) in Table 3 are SEQ ID NOs: 41 to 51, respectively. From top to bottom, the sequence identifiers of the PCT primer (reverse) in Table 3 are SEQ ID NOs: 52 to 62, respectively.

TABLE 3

| RNA name | RNA sequence | Extension primer (forward) | |
|---|---|---|---|
| dFx | GGAUCGAAAGAUUUCCGCAUCCCCGAAAGGGUACAUGGCGUUAGGU | GTAATACGACTCACTATAGGATCGAAAGATTCCGC | |
| eFx | GGAUCGAAAGAUUUCCGCGGCCCCGAAAGGGGAUUAGCGUUAGGU | GTAATACGACTCAGTATAGGATCGAAAGATTTCCGC | |
| tRNA, Pro1E2(CAU) | GGGUGAUUGGCGCAGCCUGGUAGCGCACUUCGCUCAUAACGAAGGGUCAGG GGUUCGAAUCCCCUAUCACCCGCCA | GTAATACGACTCACTATAGGGTGATTGGCGCAGCCTGGTAGCGCACTTCG | |
| tRNA, Pro1E2(CGG) | GGGUGAUUGGCGCAGCCUGGUAGCGCACUUCGUUCGGGACGAAGGGGUCAG GGGUUCGAAUCCCCUAUCACCCGCCA | GTAATACGACTCACTATAGGGTGATTGGCGCAGCCTGGTAGCGCACTTCG | |
| tRNA, Pro1E2(GAU) | GGGUGAUGGCGCAGGCUGGUAGCGCACUUCGCUGAUAACGAAGGGGUCAGG GGUUCGAAUCCCCUAUCACCCGCCA | GTAATACGACTCACTATAGGGTGATTGGCGCAGCCTGGTAGCGCACTTCG | |
| tRNA, Pro1E2(GUG) | GGGUGAUUGGCGCAGCCUGGUAGCGCACUUCGUUGUGAACGAAGGGGUCAG GGGUUCGAAUCCCCUAUCACCCGCCA | GTAATACGACTCACTATAGGGTGATTGGCGCAGCCTGGTAGCGCACTTCG | |
| tRNA, GluE2(GAU) | GUCCCCUUCGUCUAGAGGCCCAGGACACCGCCCUGAUAAGGCGGUAACAGG GGUUCGAAUUCCCCUAGGGGACGCCA | CACTATAGTCCCCTTCGTCTAGAGGCCCAGGACACCGCCCTGATAAGGCGGTAACAGGGGTTCG | |
| tRNA, GluE2(GCA) | GUCCCCUUCGUCUAGAGGCCCAGGACACCGCCCUGCAAAGGCGGUAACAGG GGUUCGAAUCCCCUAGGGGACGCCA | CACTATAGTCCCCTTCGTCTAGAGGCCCAGGACACCGCCCTGCAAAGGCGGTAACAGGGGTTCG | |
| tRNA, GluE2(GGU) | GUCCCCUUCGUCUAGACGCCCAGGACACCGCCUUGGUAAGGCGGUAACAGG GGUUCGAAUCCCCUAGGGGACGCCA | CACTATAGTCCCCTTCGTCTAGAGGCCCAGGACACCGCCTTGTGAAGGCGGTAACAGGGGTTCG | |
| tRNA, GluE2(GUG) | GUCCCCUUGGUCUAGAGGCCCAGGACACCGCCUUGUGAAGGCGGUAACAGG GGUUCGAAUCCCCUAGGGGACGCCA | CACTATAGTCCCCTTCGTCTAGAGGCCCAGGACACCGCCTTGTGAAGGCGGTAACAGGGGTTCG | |
| tRNA, fMet(CAU) | CGCGGGGUGGAGCAGCCCUGGUAGCUCGUCGGGCUCAUAACCCGAAGAUCG UCGGUUCAAAUCCGGCCCCCGCAACCA | GTAATACGACTCACTATACGCGGGGTGGAGCAGCCTGGTAGCTCGTCGGGCTCATAACCCGAAG ATCG | |
| RNA name | Extension primer (reverse) | PCR primer (forward) | PCR primer (reverse) |
| dFx | ACCTAACGCCATGTACCCTTTCGGGGATGCGGAAATCTTTCGATCC | GGCGTAATACGACTCACTATAG | ACCTAACGCCATGTACCCT |
| eFx | ACCTAACGCTAATCCCCTTTCGGGGCCCCGGAAATCTTTCGATCC | GGCGTAATACGACTCACTATAG | ACCTAACGCTAATCCCCT |
| tRNA, Pro1E2(CAU) | TGGCGGGTGATAGGGGATTCGAACCCGTGACCCCTTCGTTATGAGCGAAG TGCGCTACCAGG | GGCGTAATACGACTCACTATAG | TGmGCGGGTGATAGGGGATTC |
| tRNA, Pro1E2(CGG) | TGGCGGGTGATAGGGGATTGGAACCCGTGAGCCCTTCGTCGCGAACGAAG TGCGGTACCAGG | GGCGTAATACGACTCACTATAG | TGmGCGGGTGATAGGGGATTC |
| tRNA, Pro1EZ(GAU) | TGGCGGGTGATAGGGGATTCGAACCCCTGACCCCTTCGTTATCAGCGAAG TGCGCTACCAGG | GGCGTAATACGACTCACTATAG | TGmGCGGGTGATAGGGGATTC |
| tRNA, Pro1E2(GU3) | TGGCGGGTGATAGAGGATTCGAACCTCCGACCCCTTCGTTCACAACGAAG TGCGCTACCAGG | GGCGTAATACGACTCACTATAG | TGmGCGGGTGATAGGGGATTC |

TABLE 3-continued

| | | | |
|---|---|---|---|
| tRNA, GluE2(GAU) | TGGCGTCCCCTAGGGGATTCGAACCCCTGTTACCGCC | GTAATACGACTGACTATAGTCCCCTTCGTCTAG | TGmGCGTCCCCTAGGGGATTC |
| tRNA, GluE2(GCA) | TGGCGTCCCCTAGGGGATTCGAACGCGTGTTACCGCC | GTAATACGACTCACTATAGTCCCCTTCGTCTAG | TGmGCGTCCCCTAGGGGATTC |
| tRNA, GluE2(GGU) | TGGCGTCCCCTAGGGGATTCGAACCCCTGTTACCGCC | GTAATACGACTCACTATAGTCCCCTTCGTCTAG | TGmGCGTCCCCTAGGGGATTC |
| tRNA, GluE2(GUG) | TGGCGTCCCCTAGGGGATTCGAACCCCTGTTACCGCC | GTAATACGACTCACTATAGTCCCCTTCGTCTAG | TGmGCGTCCCCTAGGGGATTC |
| tRNA, fMet(CAU) | TGGTTGCGGGGGCCGGATTTGAACCGACGATCTTCGGGTTATGAGC | GGCGTAATACGACTCACTATAG | TGmGTTGCGGGGGCCGGA |

Based on the previously reported methods (refer to Murakami, H., Ohta, A., Ashigai, H. & Suga, H. A highly flexible tRNA acylation method for non-natural polypeptide synthesis. Nat. Methods 3, 357-359 (2006) and Saito, H., Kourouklis, D. & Suga, H. An in vitro evolved precursor tRNA with aminoacylation activity. EMBO J. 20, 1797-1806 (2001)), 2-ACPC, 2-ACHC, and D-Cys were pre-activated in the form of a 3,5-dinitrobenzyl ester (DBE), and $^{ClAc}$D-Phe and $^{ClAc}$D-Tyr were activated in the form of a cyanomethyl ester (CME). Those activated amino acids were charged onto the tRNA by using flexizymes (dFx for 2-ACPC, 2-ACHC, and D-Cys-DBE, or eFx for $^{ClAc}$D-Phe-CME and $^{ClAc}$D-Tyr). Aminoacylation using flexizymes was carried out at 0° C. in a 50 mM buffer (Bicine-KOH (pH 8.7) for 2-ACPC and 2-ACHC, D-Cys, and HEPES-KOH (pH 7.5) for $^{ClAc}$D-Phe and $^{ClAc}$D-Tyr), 600 mM $MgCl_2$, 20% DMSO, 25 μM dFx or eFx, 25 μM tRNA, and 5 mM activated amino acid. Then, the aminoacyl-tRNAs thus obtained were subjected to ethanol precipitation to remove the activated amino acid and then, the pellet was washed twice with 70% ethanol containing 0.1 M sodium acetate (pH 5.2).

Example 1: Incorporation Test of 2-ACPC into Peptide

To verify the ability of ribosome to incorporate one or a plurality of cβAAs into a peptide chain, the elongation of a peptide sequence when four 2-ACPC isomers, that is, (1R, 2R)-2-ACPC, (1R,2S)-2-ACPC, (1S,2R)-2-ACPC, and (1S, 2S)-2-ACPC were used was studied first.

[Chemical formula 32]

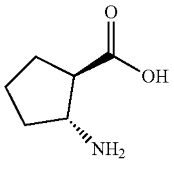

(1R,2R)-2-ACPC

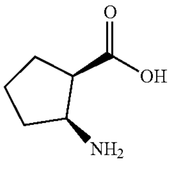

(1R,2S)-2-ACPC

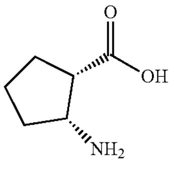

(1S,2R)-2-ACPC

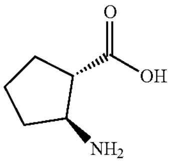

(1S,2S)-2-ACPC

Based on the method described in Murakami, H., Ohta, A., Ashigai, H. & Suga, H. A highly flexible tRNA acylation method for non-natural polypeptide synthesis. Nat. Methods 3, 357-359 (2006) and Goto, Y., Katoh, T. & Suga, H. Flexizymes for genetic code reprogramming. Nat Protoc 6, 779-790, (2011), those amino acids were charged onto $tRNA^{Pro1E2}$CGG that has a specific D-arm motif for EF-P binding and an engineered T-stem motif by using flexizymes (flexible tRNA-acylation ribozymes). The $tRNA^{Pro1E2}$CGG is shown in FIG. 1.

Then, the respective pre-charged tRNAs were added to a FIT (Flexible In vitro Translation) system, which was a reconstituted *E. coli* translation system, to express peptides rP1 to rP10. The peptides rP1 to rP10 are shown in Table 4. In their sequences, the flag in mR1 to mR13 was GACUACAAGGACGACGACGACAAG (SEQ ID NO: 344) and the flag in rP1 to rP13 was Asp-Tyr-Lys-Asp-Asp-Asp-Asp-Lys (SEQ ID NO: 345). From top to bottom, the sequence identifiers of the RNA or amino acid sequences in Table 4 are SEQ ID NOs: 83, 96, 84, 97, 98 to 105, and 85 to 92 respectively.

TABLE 4

| | |
|---|---|
| mRNA (mR1): | AUG UAC AAG AAG UAC AAA AAG UAC AAA **CCG** GGU GGU flag UAA |
| reprogrammed peptide (rP1): | fMet Tyr Lys Lys Tyr Lys Lys Tyr Lys cβAA Gly Gly flag (stop) |
| mRNA (mR2): | AUG UAC AAG AAG UAC AAA AAG UAC AAA **CCG** **CCG** GGU flag UAA |
| reprogrammed peptide (rP2): | fMet Tyr Lys Lys Tyr Lys Lys Tyr Lys cβAA cβAA Gly flag (stop) |
| mRNA (mR3-mR10): | AUG UAC AAG AAG UAC AAA AAG UAC AAA (**CCG**)$_n$ flag UAA |
| reprogrammed peptide (rP3-rP10): | fMet Tyr Lys Lys Tyr Lys Lys Tyr Lys (cβAA)$_n$ flag (stop) n = 3-10 |

The translation of the peptides was performed in the following procedure.

The FIT system used in the present example contained only 5 μM EF-P, 3 μM IF2, 20 μM EF-Tu, and 0.1 μM EF-G, and the minimum number of amino acids and aminoacyl-tRNA synthetase (ARS), that is, Met, Lys, Gly, Tyr, and Asp, and ARS corresponding thereto.

In order to improve the affinity between cβAA and tRNA, the EF-Tu concentration in the conventional FIT system (refer to Katoh, T. & Suga, H. Ribosomal incorporation of consecutive β-amino Acids. J. Am. Chem. Soc. 140, 12159-12167 (2018), Katoh, T., Tajima, K. & Suga, H. Consecutive elongation of D-amino acids in translation. Cell Chem. Biol. 24, 1-9 (2017), and Katoh, T., Iwane, Y. & Suga, H. Logical engineering of D-arm and T-stem of tRNA that enhances D-amino acid incorporation. Nucleic Acids Res. 45, 12601-12610 (2017)) was increased from 10 μM to 20 μM. Similarly, the EF-G concentration was reduced from 0.26 μM to 0.1 μM to prevent the drop-off, from a ribosome, of the peptidyl-tRNA during translation.

In order to evaluate the effect of EF-P, translation was performed also in the absence of EF-P. The details of the composition of the above particular FIT system were as shown in the following Table 5.

TABLE 5

| |
|---|
| 50 mM HEPES-KOH (pH 7.6) |
| 100 mM Potassium acetate |
| 12.3 mM Magnesium acetate |
| 2 mM ATP |
| 2 mM GTP |
| 1 mM CTP |
| 1 mM UTP |
| 20 mM Phosphocreatine |
| 0.1 mM 10-Formyl-5,6,7,8-tetrahydrofolic acid |
| 2 mM Spermidine |
| 1 mM DTT |
| 1.5 mg/mL *Escherichia coli E. coli* total tRNA |

TABLE 5-continued

| |
|---|
| 1.2 μM *Escherichia coli E. coli* ribosome |
| 0.6 μM Methionyl-tRNA formyl transferase |
| 2.7 μM IF1 |
| 3 μM IF2 |
| 1.5 μM IF3 |
| 0.1 μM EF-G |
| 20 μM EF-Tu/Ts |
| 0.25 μM RF2 |
| 0.17 μM RF3 |
| 0.5 μM RRF |
| 4 μg/mL Creatine kinase |
| 3 μg/mL Myokinase (mykinase) |
| 0.1 μM Inorganic pyrophosphatase |
| 0.1 μM Nucleotide diphosphate kinase |
| 0.1 μM T7 RNA polymerase |
| 0.13 μM AspRS |
| 0.11 μM LysRS |
| 0.03 μM MetRS |
| 0.02 μM TyrRS |
| 0.09 μM GlyRS |
| 0.05 mM [$^{14}$C]-Asp |
| 0.5 mM Lys |
| 0.5 mM Met |
| 0.5 mM Tyr |
| 0.5 mM Gly |
| 25 μM Each pre-charged aminoacyl-tRNA |
| 0.5 μM Template DNA |

The template DNAs for the peptide translation were prepared by the extension using a forward and reverse extension primer pair and the subsequent PCR using a forward and reverse PCR primer pair. Refer to Table 3 about the sequence of the primers. The PCR products thus obtained were purified by phenol/chloroform extraction and ethanol precipitation. The template DNAs were transcribed to mRNA by T7 RNA polymerase contained in the FIT system and translated into peptides. The peptides rP1 to rP11 and rP13 contained a Tyr-Lys-Lys-Tyr-Lys-Lys-Tyr-Lys sequence before a cβAA incorporation site in order to suppress the drop-off of the peptidyl-tRNA and promote ionization in MALDI-TOF MS. The translation reaction was performed at 37° C. in a 2.5 μL solution, stopped by the addition of 2.5 μL of stop solution (0.9M Tris-HCl (pH 8.45), 8% SDS, 30% glycerol, and 0.001% xylene cyanol), and heated at 95° C. for 3 minutes. Then, the samples were subjected to 15% tricine SDS-PAGE and analyzed by autoradiography using Typhoon FLA 7000 (GE Healthcare). The expression level of a radioisotope-labeled peptide was normalized by the intensity of [$^{14}$C]-Asp band.

The MALDI-TOF MS of the translated peptide was performed in the following procedure.

Translation was performed for 45 minutes in the above reaction mixture containing 0.5 mM non-radioactive Asp instead of radioactive [$^{14}$C]-Asp. Next, after addition of an equivalent amount of a 2×HBS buffer (100 mM HEPES-KOH (pH 7.6), 300 mM NaCl), the resulting mixture was mixed with 5 μL of ANTI-FLAG M2 affinity gel (Sigma) and incubated for 30 minutes at room temperature. The gel beads were washed once with 25 μL of an HBS buffer (50 mM HEPES-KOH (pH 7.6) and 150 mM NaCl) and 15 μL of 0.2% trifluoroacetic acid was added to elute the peptides from the beads. Then, the peptides were desalted using SPE C-TIP (Nikkyo Technos) and co-crystallized with α-cyano-4-hydroxycinnamic acid. MALDI-TOF MS was performed using UltrafleXtreme (Bruker Daltonics). A peptide calibration standard II (Bruker Daltonics) was used for external mass calibration.

The expression level of the peptides when four 2-ACPC isomers were used is shown in FIG. 2. The SDS-PAGE analysis results of the translation products obtained using the four 2-ACPC isomers are shown in FIGS. 3*a* to 3*d*. The MALDI-TOF MS results of the translation products obtained using the four 2-ACPC isomers are shown in FIGS. 4 and 5.

Although tRNA$^{Pro1E2}$ generally improves the consecutive incorporation efficiency of D-amino acid and β$^3$-amino acid, EF-P enhanced only the expression of rP2 when (1R,2S)-2-ACPC was used and showed a negative effect on the expression of peptides containing the other three steric isomers.

It was revealed that the efficiency of the double elongation of (1S,2S)-2-ACPC was on the same level with that of the single elongation. As a result of a test on the expression on longer peptides (rP3 to rP10), the consecutive elongation was prolonged up to 10 residues (refer to FIG. 2-IV).

Example 2: Incorporation Test of 2-ACHC into Peptide

The possibility of the introduction of four 2-ACHC isomers: (1R,2R)-2-ACHC, (1R,2S)-2-ACHC, (1S,2R)-2-ACHC, and (1S,2S)-2-ACHC into rP1 and rP2 (refer to Table 4) was tested.

[Chemical formula 33]

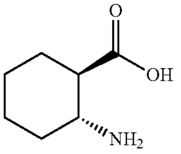

(1R,2R)-2-ACHC

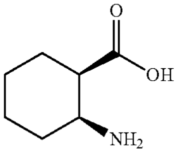

(1R,2S)-2-ACHC

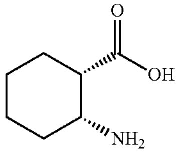

(1S,2R)-2-ACHC

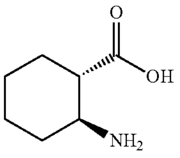

(1S,2S)-2-ACHC

The expression level of the peptides using four 2-ACHC isomers is shown in FIG. 6. The SDS-PAGE analysis results of the translation products for which four 2-ACHC isomers were used are shown in FIG. 3*e*. The MALDI-TOF MS results of the translation products obtained using four 2-ACHC isomers are shown in FIG. 7.

Four 2-ACHCs were introduced by single incorporation into rP1 and no significant difference in expression level was found between in the presence and absence of EF-P.

When two consecutive 2-ACHCs were incorporated, the product of rP2 was not observed in the absence of EF-P. On the other hand, the expression of rP2 containing (1R,2R)-2-ACHC or (1S,2S)-2-ACHC was observed in the presence of EF-P, showing that EF-P can promote the consecutive incorporation of them.

Example 3: Ribosomal Synthesis of Designed Foldamer Peptide

The possibility of consecutive incorporation of many kinds of cβAAs was tested. First, peptide rP11 containing two (1S,2S)-2-ACPCs assigned to AUU codon and one (1S,2S)-2-ACHC assigned to CAU codon was designed. The rP11 is shown in Table 6. From top to bottom, the sequence identifiers of the RNA or amino acid sequences in Table 5 are SEQ ID NOs: 93, 106, 94, 107, 95, and 108 respectively.

TABLE 6

| | | | | | | | | | | | | | |
|---|---|---|---|---|---|---|---|---|---|---|---|---|---|
| mRNA (mR11): | AUG | UAC | AAG | AAG | UAC | AAA | AAG | UAC | AAA | **AUU** | **CAU** | **AUU** | flag UAA |
| reprogrammed peptide (rP11): | fMet | Tyr | Lys | Lys | Tyr | Lys | Lys | Tyr | Lys | *(1S,2S)-2-ACPC* | *(1S,2S)-2-ACHC* | *(1S,2S)-2-ACPC* | flag (stop) |

| | | | | | | | | | | |
|---|---|---|---|---|---|---|---|---|---|---|
| mRNA (mR12): | **AUG** | **ACU** | **ACU** | **ACU** | **ACU** | **CAU** | AAG | AAG | AAG | flag UAA |
| reprogrammed peptide (rP12): | $^{ClAc}$**D-Phe** | *(1S,2S)-2-ACPC* | *(1S,2S)-2-ACPC* | *(1S,2S)-2-ACPC* | *(1S,2S)-2-ACPC* | D-**Cys** | Lys | Lys | Lys | flag (stop) |

(D-Phe and D-Cys linked via S)

| | | | | | | | | | | | | | |
|---|---|---|---|---|---|---|---|---|---|---|---|---|---|
| mRNA (mR13): | AUG | UAC | AAG | AAG | UAC | AAA | AAG | UAC | AAA | | | | |
| reprogrammed peptide (rP13): | fMet | Tyr | Lys | Lys | Tyr | Lys | Lys | Tyr | Lys | | | | |
| (continued) | **CCG** | UAC | UAU | **CCG** | UAU | UAC | **CCG** | UAC | UAU | **CCG** | flag UAA | | |
| | *(1S,2S)-2-ACPC* | Tyr | Tyr | *(1S,2S)-2-ACPC* | Tyr | Tyr | *(1S,2S)-2-ACPC* | Tyr | Tyr | *(1S,2S)-2-ACPC* | flag (stop) | | |

The finding suggesting that the presence of EF-P inhibited the incorporation of (1S,2S)-2-ACPC (in other words, a tRNA having a D-arm structure interactive with EF-P was not optimum for the introduction of (1S,2S)-2-ACPC) was obtained in Example 1, so that in order to incorporate (1S,2S)-2-ACPC, $tRNA^{GluE2}{}_{GAU}$ whose T-stem recruited EF-Tu but whose D-arm was not interactive with EF-P was selected as a tRNA. In order to incorporate (1S,2S)-2-ACHC, on the other hand, $tRNA^{Pro1E2}{}_{GUG}$ which recruited both EF-Tu and EF-P was selected.

The translation of rP11 in the presence of EF-P produced a desired peak of a full length rP11 in MALDI-TOF MS. Similarly, rP12 (refer to Table 6) having N-chloroacetyl-D-phenylalanine ($^{ClAc}$D-Phe) at the N terminal side of (1S, 2S)-2-ACPC and D-cysteine (D-Cys) downstream of (1S, 2S)-2-ACPC was expressed and it was confirmed in MALDI-TOF MS that a desired thioether cyclic skeleton was obtained. Further, rP13 (refer to Table 6) containing four (1S,2S)-2-ACPCs, each at every 3 amino acid residues, was expressed and it was confirmed that a desired peptide was obtained. The MALDI-TOF MS results of rP11, rP12, and rP13 are shown in FIG. 8.

This type of peptide containing (1S,2S)-2-ACPC is known to induce 10/11/11-helix (refer to Schmitt, M. A., Choi, S. H., Guzei, I. A. & Gellman, S. H. New helical foldamers: heterogeneous backbones with 1:2 and 2:1 a:β-amino acid residue patterns. J. Am. Chem. Soc. 128, 4538-4539 (2006)). These results have proved the possibility of ribosomal synthesis of a designed foldamer peptide having a helix.

Example 4-1: Preparation of Library

Based on the method of expressing a cyclic foldamer peptide containing a cβAA and with reference to Yamagishi, Y. et al. Natural product-like macrocyclic N-methyl-peptide inhibitors against a ubiquitin ligase uncovered from a ribosome-expressed de novo library. Chem. Biol. 18, 1562-1570 (2011). and Passioura, T., Katoh, T., Goto, Y. & Suga, H. Selection-based discovery of druglike macrocyclic peptides. Annu. Rev. Biochem. 83, 727-752 (2014)., two targets, that is, human factor XIIa (FXIIa) and interferon γ receptor 1 (IFNGR1) were selected, and new discovery of a physiologically active molecule from a random sequence library was investigated by using a RaPID (Random Non-standard Peptides Integrated Discovery) system.

The cyclic peptide library was designed, as shown below, to have a repetition of 6 to 15 random residues (encoded by an NNU codon) including three cβAAs, (1S,2S)-2-ACHC, (1R,2R)-2-ACPC, and (1S,2S)-2-ACPC which was sandwiched between cyclized $^{ClAc}$D-Tyr and D-Cys and was linked to the 3' end of mRNA via a puromycin linker. Assignment of an amino acid to an NNU codon is shown in Table 7. The sequence identifier of the RNA below is SEQ ID NO: 346. The sequence identifier of the peptide below is SEQ ID NO: 347.

[Chemical formula 34]

5′ GGGUUGAACUUUAAGUAGGAGAUAUAUCC AUG $(NNU)_x$ AUG GCC ACG GGU ACC GGG ACC UAG GACGGGGGGCGGAAA 3′ peptide library: $^{ClAc}$B-Tyr $(random)_n$ p-Cys Gly Thr Gly Thr Gly (stop)

macrocyclization (n = 6-15)

puromycin linker

TABLE 7

| 1st | 2nd: U | C | A | G | 3rd |
|---|---|---|---|---|---|
| U | Phe | Ser | Tyr | 3 | U |
| | | | | | C |
| | Leu | Ser | stop | | G |
| C | Leu | Pro | 2 | Arg | U |
| | | | | | C |
| | Leu | Pro | | Arg | G |
| A | 1 | Thr | Asn | Ser | U |
| | | | | | C |
| | $^{ClAc}$D-Tyr/D- | Thr | Lys | Arg | G |
| G | Val | Ala | Asp | Gly | U |
| | | | | | C |
| | Val | Ala | | Gly | G |

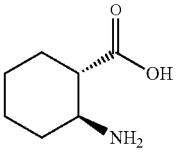

1 (1S,2S)-2-ACHC

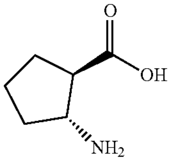

2 (1R,2R)-2-ACPC

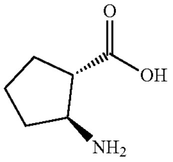

3 (1S,2S)-2-ACPC

More specifically, the preparation of the library was performed in the following procedure;

The FIT system used in the preparation of the cyclic peptide library is as shown below in Table 8.

TABLE 8

| |
|---|
| 50 mM HEPES-KOH (pH 7.6) |
| 100 mM Potassium acetate |
| 12.3 mM Magnesium acetate |
| 2 mM ATP |
| 2 mM GTP |
| 1 mM CTP |
| 1 mM UTP |
| 20 mM Phosphocreatine |
| 2 mM Spermidine |
| 1 mM DTT |
| 1.5 mg/mL *Escherichia coli E. coli* total tRNA |
| 1.2 μM *Escherichia coli E. coli* ribosome |
| 0.6 μM Methionyl-tRNA formyl transferase |
| 2.7 μM IF1 |
| 3 μM IF2 |
| 1.5 μM IF3 |
| 0.1 μM EF-G |
| 20 μM EF-Tu/Ts |
| 0.25 μM RF2 |
| 0.17 μM RR3 |
| 0.5 μM RRF |
| 4 μg/-mL Creatine kinase |
| 3 μg/mL Myokinase (mykinase) |
| 0.1 μM Inorganic pyrophosphatase |
| 0.1 μM Nucleotide diphosphate kinase |
| 0.1 μM T7 RNA polymerase |

TABLE 8-continued

| |
|---|
| 0.13 μM AspRS, 0.11 μM LysRS, 0.02 μM TyrRS, 0.09 μM GlyRS, 0.73 μM AlaRS, |
| 0.03 μM ArgRS, 0.38 μM AsnRS, 0.04 μM LeuRS, 0.15 μM PheRS, 0.16 μM ProRS, |
| 0.04 μM SerRS, 0.09 μM ThrRS, 0.04 μM ValRS, |
| 0.5 mM each of Asp, Lys, Tyr, Gly, Ala, Arg, Asn, Leu, Phe, Pro, Ser, Thr, Val |
| 12.5 μM $^{ClAc}$D-Tyr- $tRNA^{fMet}_{CAU}$ |
| 20 μM D-Cys-$tRNA^{Pro1E2}_{GAU}$ |
| 20 μM (1S,2S)-2-ACHC-$tRNA^{Pro1E2}_{GAU}$ |
| 20 μM (1R,2R)-2-ACPC-$tRNA^{GluE2}_{GUG}$ |
| 20 μM (1S,2S)-2-ACPC-$tRNA^{GluE2}_{GCA}$ |
| 1.5 μM mRNA library bound to a puromycin linker |

The peptide library was translated at 37° C. for 30 minutes in 150 μL (for the first selection), 10 μL (for the second to fourth selection), or 5 μL (for the fifth to seventh selection) FIT system.

Then, the reaction mixture was incubated at room temperature for 12 minutes and 0.04 time the amount of 500 mM EDTA (pH 8.0) was added. The resulting mixture was incubated at 37° C. for 30 minutes to induce dissociation of ribosome from the mRNA-peptide complexes.

The reverse transcription was performed at 42° C. for 15 minutes by using NNUAUG-GT3.R38 primer (5'-TTTCCGCCCCCCGTCCTAGGTCCCCGTACCCGTGCC-CA-3') (SEQ ID NO: 302) and M-MLV reverse transcriptase (Promega) lacking RNase H activity.

Then, the cDNA/mRNA/peptide complexes were mixed with Dynabeads streptavidin (Thermo Fisher) on which FXIIa was not immobilized or Dynabeads protein G (Thermo Fisher) on which IFNGR1 was not immobilized and the mixture was incubated three times at 4° C. for 15 minutes as a negative selection. The negative selection was not performed in the first round of the selection.

The supernatant of the negative selection was collected and mixed at 4° C. for 15 minutes with a 0.48× translation volume of FXIIa immobilized Dynabeads streptavidin or a 0.24× translation volume of IFNGR1 immobilized Dynabeads protein G. The beads were washed three times with 100 μL of a cold TBS-T buffer (100 mM Tris-HCl, pH7.5, 300 mM NaCl, 0.05% Tween20).

Recombinant biotinylated human FXIIa was purchased from Molecular Innovations. The recombinant human IgG1 Fc and Fc labeled human IFNGR1 were purchased from R&D systems and AcroBiosystems, respectively.

Next, 100 μL of a PCR buffer (10 mM Tris-HCl (pH 9.0), 50 mM KCl, 0.1% Triton X-100, 0.25 mM dNTP, 2.5 mM $MgCl_2$, 0.25 μM T7.F52 primer 5'-GGCGTAATACGACT-CACTATAGGGTTGAACTTTAAGTAGGAGATATATC-CAT-3' (SEQ ID NO: 303), and 0.25 μM NUAUG-GT3.R38 primer) was added to the beads and cDNAs were eluted at 95° C. for 5 minutes and amplified by PCR. The eluted solution (1 μL) was mixed with 19 μL of a PCR buffer containing SYBR Green I and Taq DNA polymerase and the amount of cDNA was determined by the Real-Time PCR.

Example 4-2: Novel Discovery of Cyclic Foldamer Peptide

First, the library was subjected to the negative selection as described above in order to remove species bound to beads and then, as positive selection, was brought into contact with a target protein immobilized on magnetic beads.

Seven rounds of affinity selection were performed and the recovery rate of cDNA in each round was measured by qPCR. As a result, in the affinity selection of FXIIa and IFNGR1, a significant increase in the recovery rate was observed after the fourth round. Deep sequencing of cDNA has revealed that peptide sequences having one or more cβAAs are abundantly present in the library of the fourth round. The peptides present in the library are shown in Table 9 (for FXIIa) and Table 10 (for IFNGR1). From top to bottom, the sequence identifiers of the peptide sequences in Table 9 are SEQ ID NOs: 109 to 162, respectively. From top to bottom, the sequence identifiers of the peptide sequences in Table 10, left column, are SEQ ID NOs: 163 to 216, respectively. From top to bottom, the sequence identifiers of the peptide sequences in Table 10, middle column, are SEQ ID NOs: 217 to 270, respectively. From top to bottom, the sequence identifiers of the peptide sequences in Table 10, right column, are SEQ ID NOs: 271 to 299, respectively.

TABLE 9

| peptide sequence | read number | peptide name |
|---|---|---|
| yNDRSTR2RLVAc | 10796 | F1 |
| yPRLFN2SYLRRc | 10761 | F2 |
| yFAYDRR1LSNN1RNYc | 1601 | F3 |
| y1AFDRTFN3RT1TRYc | 777 | |
| ySDRSDYNRRVGc | 609 | |
| yRYRNNNYRRc | 267 | |
| yRYT1NRLF1NAc | 204 | F4 |
| yFLTP1PRYNR3FTNc | 161 | |
| yR3FSDLNSLYTSc | 75 | |
| yNDRSTR2RPVAc | 75 | |
| ySDRSTR2RLVAc | 63 | |
| yPRPFN2SYLRRc | 51 | |
| yPRLFS2SYLRRc | 51 | |
| yNDRSTRHRLVAc | 49 | |
| yPRLFK2SYLRRc | 41 | |
| yPRLFN2SYPRRc | 38 | |
| ySDRSTF2R1VLG1NSc | 34 | |
| yPRLSN2SYRRc | 31 | |
| yNDRSTRRRLVAc | 30 | |
| yNDRSTR2RLAAc | 29 | |
| yFAYDRR1LSNNIRNYc | 29 | |
| yPRLLIIVIFVV | 25 | |
| y1AVDRSYS2ST1RYYc | 25 | |
| IPRLFN2SYLRRc | 22 | |
| yVDT1LRTL1NVc | 21 | |
| ySNVP3RYS2DS3RYSc | 21 | |
| yR3PADLNRLFQ | 21 | |
| yNDRSTR2RLVTc | 20 | |
| yPRLLN2SYLRRc | 19 | |
| y1AFDRTFNRRT1TRYc | 19 | |
| yPRLFN2SYLR2c | 18 | |
| yPRLFN2SYL3Rc | 18 | |
| yPRLFN2GYLRRc | 18 | |
| yNGRSTR2RLVAc | 18 | |
| yFAYDRR1LSSN1RNYc | 18 | |
| yRYT1NRLL1NAc | 17 | |
| yFAYDRR1LSNS1RNYc | 17 | |
| yPRLFN2SYLR3c | 16 | |
| yNDRST32RLVAc | 16 | |
| yRYRNDNYRRc | 15 | |
| yPRLFN2S2LRRc | 15 | |
| yPRLFN2SYL2Rc | 14 | |
| yNDRSTR23LVAc | 14 | |
| yTNT1LRLLSNc | 13 | |
| yNDRSTR22LVAc | 13 | |
| yNDRSAR2RLVAc | 13 | |
| yND2STR2RLVAc | 13 | |
| yPRLFNRSYLRRc | 12 | |
| y1ATNRV3VNRT13NYc | 12 | |
| yP2LFN2SYLRRc | 11 | |
| yNDRSTR2RL1Ac | 11 | |
| yGYL3FTc | 11 | |
| INDRSTR2RLVAc | 11 | |
| yFAYDRRILSNN1RNYc | 10 | |

TABLE 10

| peptide sequence | read number | peptide name |
|---|---|---|
| yFGVR2FYNRTc | 15739 | I1-1 |
| y1GLS2YVNRSc | 8376 | I1-2 |
| yVGLN2SLNRTc | 4401 | I1-3 |
| yFGLS2FYRRSc | 2944 | |
| yFSLR2SFNRSRGc | 2118 | I1-4 |
| y1GLSHYVNRSc | 1401 | |
| yYGVN2SYNRSc | 1163 | |
| yYSVS2RFNRTc | 948 | |
| yFDLR2RLANc | 906 | |
| yFALN2RINRRc | 779 | I1-5 |
| yYDLR2RLYRNc | 694 | |
| y1ALSRSRRTTRONc | 866 | |
| yFGLS21LSRc | 452 | |
| yYDLR2RLSNc | 368 | |
| yYDLR2RLYSc | 364 | |
| yYNVR2FVNRTc | 343 | |
| yFDVR2RINSc | 240 | |
| yFGLS2FVSPc | 235 | |
| y1GLNRSLPPRLYNc | 177 | |
| yYDLR2ATNNc | 168 | |
| y1GLS2YVNRTc | 140 | |
| y1SLSRNRVPRLVLTc | 120 | |
| yYDVR2RVSNc | 107 | |
| yYSVN2Y3RNSNNc | 105 | |
| yIGLS2YVNRSc | 82 | |
| yRSSN1RPRLRY22Lc | 80 | |
| yYGLS2YVSNc | 74 | |
| yFGVR2LYNRTc | 71 | |
| yFSVY2FFNRLc | 71 | |
| y1GLG2YVNRSc | 60 | |
| yYDVR2R1VNc | 64 | |
| yFGLT2YLNRNc | 63 | |
| yLGVR2FYNRTc | 63 | |
| yPRYNL3GASPRF2Nc | 63 | I2 |
| y1GR2YFNRSc | 62 | |
| yYDLR2Y1RNc | 61 | |
| yFGVRHFYNRTc | 60 | |
| yFGAR2FYNRTc | 55 | |
| yNSRVRLYLNPc | 54 | |
| yYDL32R1SNc | 54 | |
| yFGVR2FYNRAc | 52 | |
| yFGR22FNRSc | 50 | |
| y1GLSRSNPN3RNPc | 48 | |
| yFALR2FFANc | 46 | |
| yYGLS2YFRDc | 46 | |
| yYNLR2F1SNc | 46 | |
| y1GLS2Y1NRSc | 45 | |
| yFGVR2FYDRTc | 44 | |
| yYSVR2A1NRVc | 44 | |
| yFGVR2FYNRSc | 42 | |
| yYGLS21VSLc | 37 | |
| y1GLS2YVNRNc | 36 | |
| yFGLS2FYRRTc | 36 | |
| y1GLS2YVDRSc | 33 | |
| yYDVR2R1YNc | 32 | |
| yFGV32FYNRTc | 31 | I1-6 |
| yVGLS2YVNRSc | 31 | |
| yYDLR2R1VRNc | 31 | |
| y1ALSRRRRSYRNGLc | 30 | |
| ySGVR2FYNRTc | 30 | |
| yYGLS2FLSNc | 29 | |
| y1DLR2RLYDc | 28 | |
| y1G1YRRYLPRRSPc | 28 | |
| yTGLS2YVNRSc | 28 | |
| yFGLSHFYRRSc | 27 | |
| yFGVR2FVSRTc | 27 | |
| yYDVR2RLNPNc | 27 | |
| y1G1SSFSRNSVNRSc | 26 | |
| yFNL32FLSPc | 26 | |
| yYNLR2Y1NRSNc | 26 | |
| yFGVR2F2NRTc | 25 | |
| yFGVR2FYN2Tc | 25 | |
| yFSLR2SFNRSRSc | 24 | |

TABLE 10-continued

| peptide sequence | read number | peptide name |
|---|---|---|
| yYTR2GRSR1Nc | 24 | |
| y1GLS22VNRSc | 23 | |
| y1PVNRY1RRFNRc | 23 | |
| yFGVR2SYNRTc | 23 | |
| yYDLR2RFN32DTSP2c | 23 | |
| y1SVRRY31LN3NRSLc | 21 | |
| yFDVR2FYNRTc | 21 | |
| yFGLG2FYRRSc | 21 | |
| yYDVR2F1RTc | 21 | |
| yYDVR2FLRTc | 21 | |
| y1ALN2A1NRSc | 20 | |
| y1GLN21LNRAc | 20 | |
| y1GPS2YVNRSc | 20 | |
| y1SPRR2TFNRTc | 20 | |
| yFGVR2F11VL | 20 | |
| y1GLS2YANRSc | 19 | |
| y1SLS2YVNRSc | 19 | |
| yFGVR2F3NRTc | 19 | |
| y1GLS2YVSRSc | 18 | |
| y1GVR2FYNRTc | 18 | |
| yFGLS2LYRRSc | 18 | |
| yVGLNHSLNRTc | 18 | |
| y1AVT2FVNRSNDc | 17 | |
| y1GLN2YVNRSc | 17 | |
| y1GLSRYVNRSc | 17 | |
| y3DVR2R1SNc | 17 | |
| yFGLS2YVNRSc | 17 | |
| yFGVRRFYNRTc | 17 | |
| yYGLN2T1N3Gc | 17 | |
| yYGVN2SYNRTc | 17 | |
| y1DLS2VVNRSc | 16 | |
| y1GLS2YVNRGc | 16 | |
| yFDLR2Y13Nc | 16 | |
| yRA1R2SGRLNSc | 16 | |
| yY1RY22Lc | 16 | |
| yYDLR2R1RTc | 16 | |
| yYGLS2FLSSc | 16 | |
| yFSLRHSFNRSRGc | 15 | |
| yAGLN2SLNRTc | 14 | |
| yFGLS2FYRRNc | 14 | |
| yFGVR2FYN3Tc | 14 | |
| yFSVR2FYNRTc | 14 | |
| yYGVR2FYNRTc | 14 | |
| I1GLS2YVNRSc | 13 | |
| y1GLSHYVNRTc | 13 | |
| yFGLS2SYRRSc | 13 | |
| yFS1R2VFNRSc | 13 | |
| yYD1R2RLNAc | 13 | |
| yYSVR2AINRVc | 12 | |
| y1GLGHYVNRSc | 11 | |
| y1GLN2SLNRTc | 11 | |
| yFG1R2FYNRTc | 11 | |
| yFGV22FYNRTc | 11 | |
| yVGLN2SLNRSc | 11 | |
| IFGVR2FYNRTc | 10 | |
| y1GLR2YVNRSc | 10 | |
| y1SLT2FVNRRc | 10 | |

TABLE 10-continued

| peptide sequence | read number | peptide name |
|---|---|---|
| yFGLN2FYRRSc | 10 | |
| yFGVR2FYNRNc | 10 | |
| yIGLSHYVNRSc | 10 | |
| yVGLN2SPNRTc | 10 | |
| yYALN2Y1SNc | 10 | |
| yYDLR2R1Gc | 10 | |
| yYNLR2A1NTNc | 10 | |

Four species bound to FXIIa (Table 9, F1 to F4) and seven species bound to IFNGR1 (Table 10, 11-1 to I1-6 and 12) in Tables 9 and 10 were subjected to chemical synthesis (solid-phase synthesis) and further analysis. The C-terminal TGTGT linker sequence was omitted in the chemical synthesis. In addition, negative control peptides having cβAA residue substituted with alanine were synthesized.

The binding kinetics of those peptides to FXIIa and IFNGR1 was analyzed by surface plasmon resonance. The control peptides showed significantly low affinity for the target, showing that the cβAA residue was essential for firm binding to the target. The binding affinity was analyzed at 25° C. by SPR by using a Biacore T200 apparatus (GE Healthcare). The peptides, each used at five different concentrations, were injected at a flow rate of 30 μL/min and the rate constant was measured by single cycle kinetics method. The binding sensorgrams thus obtained were analyzed using a Biacore evaluation software and was fitted to a standard 1:1 interaction model.

Furthermore, the inhibitory activity of F1, F2, F3, and F4 against the enzymatic activity of FXIIa was analyzed and their Ki values were measured. Their inhibitory activity was significantly stronger than that of a corn trypsin inhibitor (CTI, Ki=24 nM, M.W.=12.5 kDa), a small protein inhibitor against FXIIa. The Ki value of FXIIa was evaluated by cleavage of substrate peptide H-D-Pro-Phe-Arg-pNA (reagent S-2302). The release of the pNA chromophore by cleavage reaction was monitored using a plate reader Infinite M1000PRO (TECAN) at an absorbance at 405 nm.

The structure, surface plasmon resonance measurement results, and Ki value measurement results of the synthesized peptides are shown in Table 11 and Table 12. From top to bottom, the sequence identifiers of the amino acid sequences in Table 11 are SEQ ID NOs: 348 to 355, respectively. From top to bottom, the sequence identifiers of the amino acid sequences in Table 12 are SEQ ID NOs: 356 to 364, respectively.

TABLE 11

| Peptide name | Sequence | Read number | $k_a$ ($10^6 \cdot M^{-1} \cdot s^{-1}$) | $k_d$ ($10^{-2} \cdot s^{-1}$) | $K_D$ (nM) | $K_i$ (nM) |
|---|---|---|---|---|---|---|
| F1 | S<br>$^{Ac}$γNDRSTR2RLVAcG-$NH_2$ | 10796 | 2.74 | 2.25 | 8.21 | 22.1 |
| F1A | S<br>$^{Ac}$γNDRSTRARLVAcG-$NH_2$ | 0 | 0.58 | 2.97 | 51.3 | not tested |

TABLE 11-continued

| Peptide name | Sequence | Read number | $k_a$ ($10^6 \cdot M^{-1} \cdot s^{-1}$) | $k_d$ ($10^{-2} \cdot s^{-1}$) | $K_D$ (nM) | $K_i$ (nM) |
|---|---|---|---|---|---|---|
| F2 | $^{Ac}\gamma$PRLFN2SYLRRcG-$NH_2$ | 10761 | 30.7 | 1.78 | 0.58 | 2.14 |
| F2A | $^{Ac}\gamma$PRLFNASYLRRcG-$NH_2$ | 0 | 4.75 | 43.8 | 92.2 | not tested |
| F3 | $^{Ac}\gamma$FAYDRR1LSNN1RNYcG-$NH_2$ | 1601 | 1.59 | 0.16 | 0.98 | 1.02 |
| F3A | $^{Ac}\gamma$FAYDRRALSNNARNYcG-$NH_2$ | 0 | — | — | — | not tested |
| F4 | $^{Ac}\gamma$RYT1NRLF1NAcG-$NH_2$ | 204 | 0.55 | 0.85 | 15.5 | 4.32 |
| F4A | $^{Ac}\gamma$RYTANRLFANAcG-$NH_2$ | 0 | — | — | — | not tested |

TABLE 12

| Peptide name | Sequence | Read number | $k_a$ ($10^6 \cdot M^{-1} \cdot s^{-1}$) | $k_d$ ($10^{-2} \cdot s^{-1}$) | $K_D$ (nM) |
|---|---|---|---|---|---|
| I1-1 | $^{Ac}\gamma$FGVR2FYNRTcG-$NH_2$ | 15739 | 1.74 | 0.87 | 5.00 |
| I1-2 | $^{Ac}\gamma$1GLS2YVNRScG-$NH_2$ | 8376 | — | — | — |
| I1-3 | $^{Ac}\gamma$VGLN2SLNRTcG-$NH_2$ | 4401 | 1.41 | 21.1 | 150 |
| I1-4 | $^{Ac}\gamma$FSLR2SFNRSRGcG-$NH_2$ | 2118 | 3.39 | 1.95 | 5.76 |
| I1-5 | $^{Ac}\gamma$FALN2R1NRRcG-$NH_2$ | 779 | 3.01 | 101 | 336 |
| I1-6 | $^{Ac}\gamma$FGV32FYNRTcG-$NH_2$ | 31 | 0.92 | 0.17 | 1.87 |
| I1-1A | $^{Ac}\gamma$FGVRAFYNRTcG-$NH_2$ | 0 | 0.02 | 4.12 | 2390 |
| I2 | $^{Ac}\gamma$PRYNL3GASPRF2NcG-$NH_2$ | 63 | 1.98 | 2.43 | 12.3 |
| I2A | $^{Ac}\gamma$PRYNLAGASPRFANcG-$NH_2$ | 0 | — | — | — |

Example 5: Serum Stability of Peptides Bound to FXIIa and IFNGR1

The serum stability of peptides was analyzed using, for FXIIa, F1, F2, F3, and F4 and Ala mutants F1A, F3A, and F4A and for IFNGR1, 11-6 and a mutant thereof I1-1A.

The aforesaid peptides and the following peptidase-resistant internal standard peptide were co-incubated at 37° C. in the human serum.

[Chemical formula 35]

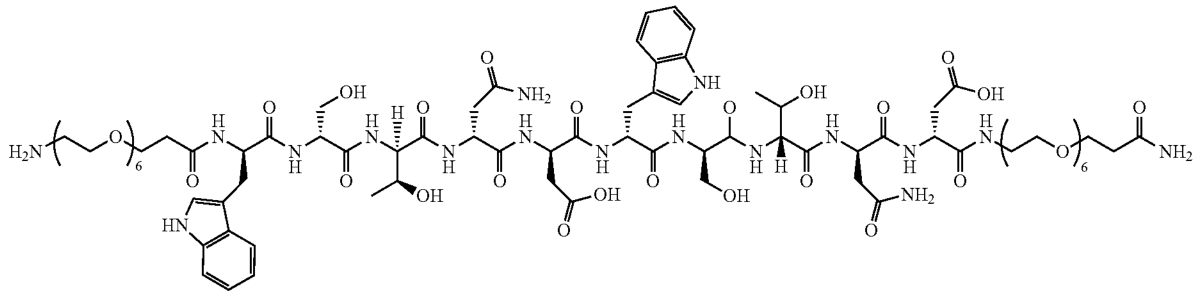

A relative amount of the sample peptides to the standard peptide at 0, 1, 3, 9, 24, 72, 144, and 240 hours was calculated by liquid chromatography/mass spectrum (LC/MS). A change in relative amount at 0, 1, 3, 9, 24, 72, 144, and 240 hours is shown in FIG. 9.

High serum resistance and binding/inhibitory activity of peptides were observed, revealing that a library including cyclic peptides containing cβAA expressed between $^{ClAc}$D-Tyr and D-Cys can be applied to the development of a unique peptide drug.

Example 6: Cocrystal Structure of F3 Bound to FXIIa

To elucidate the action mechanism and folding tendency of the cβAA-containing peptide, the cocrystal structure of F3 bound to FXIIa was analyzed by X-ray crystallography. The analysis results are shown in FIG. 10.

The diffraction data revealed that F3 was folded into an antiparallel p sheet and in the folded sheet, (1S,2S)-2-ACHC at position 8 (ACHC8) was located at the edge of the turn of the β-sheet close to the active center of FXIIa. The $^{Ac}$D-Tyr1 and D-Cys17 were located at the other edge of the p sheet distant from the active site of the enzyme, which is expected since the D-Cys17 is bound to the cognate mRNA via the peptide-puromycin linker during the selection.

It has also been found that Arg7, ACHC8, and Leu9 were present at positions i, i+1, and i+2, respectively and ACHC8 incorporated into a middle position of the sequence induced a pseudo γ turn.

The above results accorded with the previous report that a p amino acid at position i+1 was a pseudo γ turn inducer (Schumann, F., Muller, A., Koksch, M., Muller, G. & Sewald, N. Are β-amino acids γ-turn mimetics?Exploring a new design principle for bioactive cyclopeptides. J. Am. Chem. Soc. 122, 12009-12010 (2000)). Further, a reverse γ turn was formed by ACHC8, Leu9, and Ser10 (i, i+1, and i+2, respectively). Such two consecutive γ turns bound to ACHC8 were unique characteristics of the peptide, which were presumed to contribute to the folding of the peptide into the anti-parallel β sheet.

Another (1S,2S)-2-ACHC(ACHC13) at position 13 was involved in a p turn in which ACHC13, Arg14, Asn15, and Tyr16 held the positions i to i+3. The amide group of ACHC13 also formed an intramolecular p sheet-like hydrogen bond with Ala3 and its cyclic side-chain formed an intramolecular hydrophobic interaction with Ala3 and Tyr16.

As described above, it has been made clear that two (1S,2S)-2-ACHC residues contributed to the overall folding by inducing a turn structure and forming an intramolecular interaction.

F3 bound to the active site of FXIIa in a substrate-like manner and acted as an inhibitor having a so-called standard mechanism (Refer to Farady, C. J. & Craik, C. S. Mechanisms of macromolecular protease inhibitors. ChemBioChem 11, 2341-2346 (2010) and Laskowski, M. & Kato, I. Protein inhibitors of proteinases. Annu. Rev. Biochem. 49, 593-626 (1980)).

The peptide bond between Arg6 and Arg7 was located close to the catalytic Ser563 of FXIIa.

The Arg6 side chain formed a salt bridge with the Asp557 of FXIIa and was accommodated in the S1 pocket of the enzyme. Arg6 is a widely conserved amino acid among natural substrates of FXIIa as well as previously reported inhibitors such as PPACK, Infestin-4, EcTI (*E. contortisiliquum* trypsin inhibitor), CTI, FXII618, and FXII801.

The Arg7 side chain also formed a hydrogen bond with Ser395 and Cys413, while the ACHC8 side chain bound to a shallow hydrophobic pocket formed by Tyr515 and His507 of FXIIa. F3 also formed an intramolecular p sheet-like hydrogen bond with FXIIa Gly587 via its Tyr4 and its steric conformation was stabilized by the formation of an intramolecular p sheet with Asn11-ACHC13. In addition, there are extensive hydrophobic interactions around ACHC13, contributed by Ala3 and Tyr16 of F3 and Tyr458 and Trp586 of FXIIa.

Example 7: Incorporation Test of γ Amino Acid into Peptide

An incorporation test of the following γ-amino acids was performed in accordance with the method of Example 1.

[Chemical formula 36]

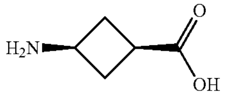

cis-3-ACBC

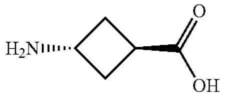

trans-3-ACBC

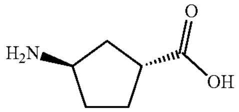

(1R,3R)-3-ACPC

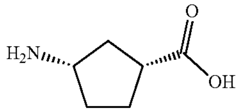

(1R,3S)-3-ACPC

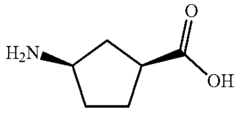

(1S,3R)-3-ACPC

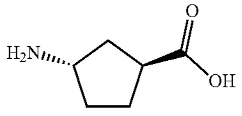

(1S,3S)-3-ACPC

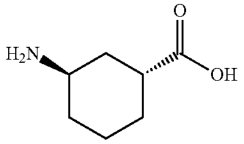

(1R,3R)-3-ACHC

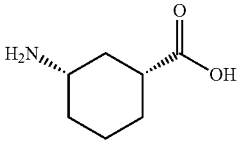

(1R,3S)-3-ACHC

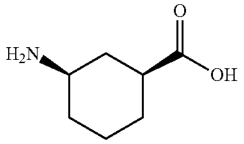

(1S,3R)-3-ACHC

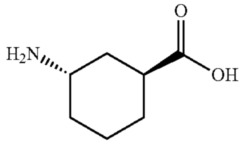

(1S,3S)-3-ACHC

The following mR1 was used as a template mRNA and translated into peptide rP1. The γ amino acid was charged onto $tRNA^{Pro1E2}$CGG. From top to bottom, the sequence identifiers of the RNA or amino acid sequence below are SEQ ID NOs: 300, and 301 respectively.

[Chemical formula 37]

```
mRNA (mR1):
AUG UAC AAG AAG UAC AAA AAG UAC AAA GCU CCG GGU
flag UAA

reprogrammed peptide (rP1):
fMet Tyr Lys Lys Tyr Lys Lys Tyr Lys Phe γ-aa Gly
flag (stop)
```

As a result, it was confirmed from MALDI-TOF MS that eight cyclic γ-amino acids, that is, cis-3-ACBC, trans-3-ACBC, (1R,3R)-3-ACPC, (1R,3S)-3-ACPC, (1S,3R)-3-ACPC, (1R,3S)-3-ACPC, (1R,3R)-3-ACHC, and (1R,3S)-3-ACHC were incorporated in the peptide rP1 (refer to FIG. 11).

In accordance with the method of Example 1, the incorporation efficiency of each of the steric isomers of the γ amino acids into the peptide rP1, depending on the presence or absence of EF-P was studied.

The results of the incorporation efficiency of each of the steric isomers of the β or γ amino acids studied through Example 1 and Example 7 are shown in Table 13.

TABLE 13

| Substrate | Effect of EF-P |
|---|---|
| (1R,2R)-2-ACPC | inhibition |
| (1R,2S)-2-ACPC | promotion |
| (1S,2R)-2-ACPC | inhibition |
| (1S,2S)-2-ACPC | inhibition |
| (1R,2R)-2-ACHC | promotion |
| (1R,2S)-2-ACHC | no effect |
| (1S,2R)-2-ACHC | no effect |
| (1S,2S)-2-ACHC | promotion |
| cis-3-ACBC | promotion |
| trans-3-ACBC | promotion |
| (1R,3R)-3-ACPC | promotion |
| (1R,3S)-3-ACPC | inhibition |
| (1S,3R)-3-ACPC | inhibition |
| (1S,3S)-3-ACPC | promotion |
| (1R,3R)-3-ACHC | promotion |
| (1R,3S)-3-ACHC | inhibition |
| (1S,3R)-3-ACHC | — |
| (1S,3S)-3-ACHC | — |

Example 8: Incorporation Test of Aromatic Amino Acid into Peptide

The incorporation test of the following aromatic amino acids was performed. The σ values of β-hydroxy-, β-methoxy-, and β-fluoro-substituted aromatic amino acids as the aromatic amino acid having a substituent are shown.

[Chemical formula 38]

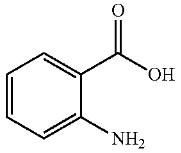

2-Aminobenzoic acid (Abz)

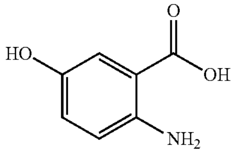

2-Amino-5-hydroxy benzoic acid ($Abz^{5OH}$) $\sigma_p$-OH = -0.37

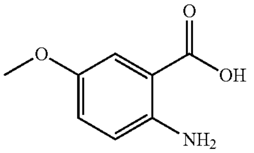

2-Amino-5-methoxy benzoic acid ($Abz^{5OMe}$) $\sigma_p$-OMe = -0.27

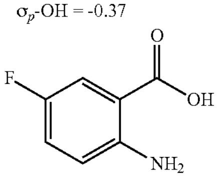

2-Amino-5-fluoro benzoic acid ($Abz^{5F}$) $\sigma_p$-F = 0.06

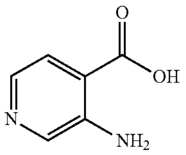

3-Aminopyridine-4-carboxylic acid (Apy)

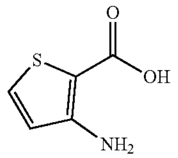

3-Aminothiophene-2-carboxylic acid (Atp)

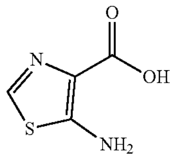

5-Aminothiazole-4-carboxylic acid (Atz)

-continued

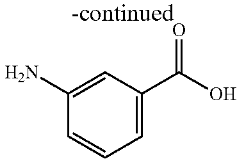

3-Aminobenzoic acid-
($^{3N}$Abz)

(Preparation of tRNA)

The tRNAs to be charged with the aromatic amino acid were prepared in a manner similar to that described above (preparation of tRNA). Refer to Table 14 about the sequence of a primer. From top to bottom, the sequence identifiers of the RNA sequences in Table 14 are SEQ ID NOs: 8, 9, 11, 304, 10, 305, 12, 306, 13, 307, 14, and 18, respectively. From top to bottom, the sequence identifiers of the Extension primer (forward) in Table 14 are SEQ ID NOs: 19, 20, 22, 308, 21, 309, 23, 310, 24, 311, 25, and 29, respectively. From top to bottom, the sequence identifiers of the Extension primer (reverse) in Table 14 are SEQ ID NOs: 30, 31, 33, 312, 32, 313, 34, 314, 35, 315, 36, and 40, respectively. From top to bottom, the sequence identifiers of the PCT primer (forward) in Table 14 are SEQ ID NOs: 41, 42, 44, 316, 43, 317, 45, 318, 46, 319, 47, and 51, respectively. From top to bottom, the sequence identifiers of the PCT primer (reverse) in Table 14 are SEQ ID NOs: 52, 53, 55, 320, 54, 321, 56, 322, 57, 323, 58 and 62.

TABLE 14

| RNA name | RNA sequence | Extension primer (forward) |
|---|---|---|
| dFx | GGAUCGAAAGAUUUCCGCAUCCCCGAAAGGGUACAUGGCGUUAGGU | GTAATACGACTCACTATAGGATCGAAAGATTCCGC |
| eFx | GGAUCGAAAGAUUUCCGCGGCCCCGAAAGGGGAUUAGCGUUAGGU | GTAATACGACTCAGTATAGGATCGAAAGATTTCCGC |
| tRNA, Pro1E2(CAU) | GGGUGAUUGGCGCAGCCUGGUAGCGCACUUCGCUCAUAACGAAGGGUCAGGGGUUCGAAUCCCCUAUCACCCGCCA | GTAATACGACTCACTATAGGGTGATTGGCGCAGCCTGGTAGCGCACTTCG |
| tRNA, Pro1E2(CGG) | GGGUGAUUGGCGCAGCCUGGUAGCGCACUUCGUUCGGGACGAAGGGGUCAGGGGUUCGAAUCCCCUAUCACCCGCCA | GTAATACGACTCACTATAGGGTGATTGGCGCAGCCTGGTAGCGCACTTCG |
| tRNA, Pro1E2(GAU) | GGGUGAUGGCGCAGGCUGGUAGCGCACUUCGCUGAUAACGAAGGGGUCAGGGGUUCGAAUCCCCUAUCACCCGCCA | GTAATACGACTCACTATAGGGTGATTGGCGCAGCCTGGTAGCGCACTTCG |
| tRNA, Pro1E2(GUG) | GGGUGAUUGGCGCAGCCUGGUAGCGCACUUCGUUGUGAACGAAGGGGUCAGGGGUUCGAAUCCCCUAUCACCCGCCA | GTAATACGACTCACTATAGGGTGATTGGCGCAGCCTGGTAGCGCACTTCG |
| tRNA, GluE2(GAU) | GUCCCCUUCGUCUAGAGGCCCAGGACACCGCCCUGAUAAGGCGGUAACAGGGGUUCGAAUUCCCCUAGGGGACGCCA | CACTATAGTCCCCTTCGTCTAGAGGCCCAGGACACCGCCCTGATAAGGCGGTAACAGGGGTTCG |
| tRNA, GluE2(GCA) | GUCCCCUUCGUCUAGAGGCCCAGGACACCGCCCUGCAAAGGCGGUAACAGGGGUUCGAAUCCCCUAGGGGACGCCA | CACTATAGTCCCCTTCGTCTAGAGGCCCAGGACACCGCCCTGCAAAGGCGGTAACAGGGGTTCG |
| tRNA, GluE2(GGU) | GUCCCCUUCGUCUAGACGCCCAGGACACCGCCUUGGUAAGGCGGUAACAGGGGUUCGAAUCCCCUAGGGGACGCCA | CACTATAGTCCCCTTCGTCTAGAGGCCCAGGACACCGCCTTGTGAAGGCGGTAACAGGGGTTCG |
| tRNA, GluE2(GUG) | GUCCCCUUGGUCUAGAGGCCCAGGACACCGCCUUGUGAAGGCGGUAACAGGGGUUCGAAUCCCCUAGGGGACGCCA | CACTATAGTCCCCTTCGTCTAGAGGCCCAGGACACCGCCTTGTGAAGGCGGTAACAGGGGTTCG |
| tRNA, fMet(CAU) | CGCGGGGUGGAGCAGCCCUGGUAGCUCGUCGGGCUCAUAACCCGAAGAUCGUCGGUUCAAAUCCGGCCCCCGCAACCA | GTAATACGACTCACTATACGCGGGGTGGAGCAGCCTGGTAGCTCGTCGGGCTCATAACCCGAAGATCG |

| RNA name | Extension primer (reverse) | PCR primer (forward) | PCR primer (reverse) |
|---|---|---|---|
| dFx | ACCTAACGCCATGTACCCTTTCGGGGATGCGGAAATCTTTCGATCC | GGCGTAATACGACTCACTATAG | ACCTAACGCCATGTACCCT |
| eFx | ACCTAACGCTAATCCCCTTTCGGGGCCCCGGAAATCTTTCGATCC | GGCGTAATACGACTCACTATAG | ACCTAACGCTAATCCCCT |
| tRNA, Pro1E2(CAU) | TGGCGGGTGATAGGGGATTCGAACCCGTGACCCCTTCGTTATGAGCGAAGTGCGCTACCAGG | GGCGTAATACGACTCACTATAG | TGmGCGGGTGATAGGGGATTC |
| tRNA, Pro1E2(CGG) | TGGCGGGTGATAGGGGATTGGAACCCGTGAGCCCTTCGTCGCGAACGAAGTGCGGTACCAGG | GGCGTAATACGACTCACTATAG | TGmGCGGGTGATAGGGGATTC |
| tRNA, Pro1EZ(GAU) | TGGCGGGTGATAGGGGATTCGAACCCCTGACCCCTTCGTTATCAGCGAAGTGCGCTACCAGG | GGCGTAATACGACTCACTATAG | TGmGCGGGTGATAGGGGATTC |
| tRNA, Pro1E2(GU3) | TGGCGGGTGATAGAGGATTCGAACCTCCGACCCCTTCGTTCACAACGAAGTGCGCTACCAGG | GGCGTAATACGACTCACTATAG | TGmGCGGGTGATAGGGGATTC |

TABLE 14-continued

| | | | |
|---|---|---|---|
| tRNA, GluE2(GAU) | TGGCGTCCCCTAGGGGATTCGAACCCCTGTTACCGCC | GTAATACGACTGACTATAGTCCCCTTCGTCTAG | TGmGCGTCCCCTAGGGGATTC |
| tRNA, GluE2(GCA) | TGGCGTCCCCTAGGGGATTCGAACGCGTGTTACCGCC | GTAATACGACTCACTATAGTCCCCTTCGTCTAG | TGmGCGTCCCCTAGGGGATTC |
| tRNA, GluE2(GGU) | TGGCGTCCCCTAGGGGATTCGAACCCCTGTTACCGCC | GTAATACGACTCACTATAGTCCCCTTCGTCTAG | TGmGCGTCCCCTAGGGGATTC |
| tRNA, GluE2(GUG) | TGGCGTCCCCTAGGGGATTCGAACCCCTGTTACCGCC | GTAATACGACTCACTATAGTCCCCTTCGTCTAG | TGmGCGTCCCCTAGGGGATTC |
| tRNA, fMet(CAU) | TGGTTGCGGGGGCCGGATTTGAACCGACGATCTTCGGGTTATGAGC | GGCGTAATACGACTCACTATAG | TGmGTTGCGGGGGCCGGA |

μhRNA, isatoic anhydride, 5-hydroxyisatoic anhydride, 5-methoxyisatoic anhydride, and 5-fluoroisatoic anhydride were purchased from Eurofin Genomics, Tokyo Chemical Industry, FUJIFILM Wako Chemicals, Combi-Blocks, and BLD Pharm, respectively (the anhydrides used in the experiment have the following structures).

[Chemical formula 39]

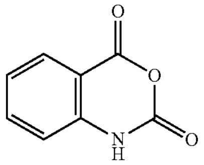

isatoic anhydride

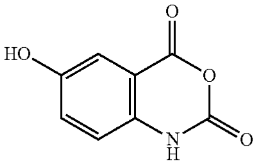

5-Hydroxy-isatoic anhydride

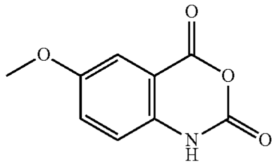

5-Methoxy-isatoic anhydride

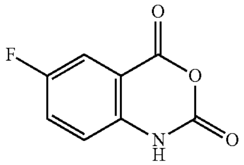

5-Fluoro-isatoic anhydride

The aminoacylation using those anhydrides was performed at 25° C. for 1 to 3 hours in 25 μL of a reaction mixture containing 80 μM μhRNA or tRNA containing 50 mM Bicine-KOH (pH 9.0), CHES-KOH (pH 9.5 or 10.0), or CAPS-KOH (pH 10.5). The concentration of the anhydrides except 5-fluoroisatoic anhydride (8 mM) was set at 10 mM.

The $^{Me}$Ser, (1S,2S)-2-ACPC, and D-Cys were preactivated as a 3,5-dinitrobenzyl ester (DBE) form and the Apy, Atp, Atz, $^{3N}$Abz, and $^{ClaAc}$D-Phe were preactivated as a cyanomethyl ester (CME) form. Those activated amino acids were charged onto μhRNA or tRNA by using flexizyme (dFx for DBE and eFx for CME).

The aminoacylation of Apy, Atp, Atz, and $^{3N}$Abz was performed at 4° C. for 24 to 336 hours in a reaction mixture containing 600 mM $MgCl_2$, 20% DMSO, 25 μM eFx, 25 μM μhRNA or tRNA, and 20 mM activated amino acid. The pH of the mixture was adjusted with 50 mM Bicine-KOH (pH 9.0), CHES-KOH (pH 9.5 or 10.0), or CAPS-KOH (pH 10.5).

The aminoacylation of $^{ClAc}$D-Phe, $^{Me}$Ser, (1S,2S)-2-ACPC, and D-Cys was performed at 4° C. in a 50 mM buffer (Bicine-KOH (pH 8.7) for (1S,2S)-2-ACPC and HEPES-KOH (pH 7.5) for $^{ClAc}$D-Phe, $^{Me}$Ser and D-Cys), 600 mM $MgCl_2$, 20% DMSO, 25 μM dFx or eFx, 25 μM tRNA, and 5 mM activated amino acid. The reaction time was 2 hours for $^{ClAc}$D-Phe, 6 hours for $^{Me}$Ser and D-Cys, and 16 hours for (1S,2S)-2-ACPC. Then, the aminoacyl-tRNAs thus obtained were subjected to ethanol precipitation and the pellet was washed twice with 70% ethanol.

Aminoacyl-μhRNA (20 μmol) was analyzed using 20% polyacrylamide gel containing 6 M urea. The pH was adjusted to 5.2 with 50 mM sodium acetate (pH 5.2) except in the analysis of Atp-μhRNA and Atz-μhRNA (pH 3.5). Electrophoresis was performed for 2.5 hours at 120 V, followed by ethidium bromide staining and detection using Typhoon FLA 7000 (GE Healthcare).

(Translation of Peptide and Electrophoresis)

The translation of the peptide was performed at 37° C. for 30 minutes in a system similar to the *Escherichia-coli* reconstituted translation system having the composition of Table 5 except for the addition of 0.11 μM LysRS, 0.68 μM PheRS, and 0.5 mM Phe. Then, 5 μL of a stop solution [0.9M Tris-HCl (pH 8.45), 8% SDS, 30% glycerol, and 0.001% xylene cyanol] was added to 5 μL of the reaction mixtures and the resulting mixtures were incubated at 95° C. for 3 minutes. Then, the samples were subjected to 15% tricine SDS-PAGE and analyzed by autoradiography using Typhoon FLA 7000 (GE Healthcare). The expression level of the peptide was normalized by the intensity of the [$^{14}$C]-Asp band.

(MALDI-TOF MS of Peptide and Aminoacyl-μhRNA)

For MALDI-TOF MS, the translation reaction was performed for 60 minutes in the presence of 0.5 mM non-radioactive Asp instead of [$^{14}$C]-Asp. The translation of the cyclic peptides (rP5 to rP10, refer to FIG. 14) was performed while omitting MetRS, Met, and 10-formyl-5,6,7,8-tetrahydrofolic acid from the aforesaid reaction mixture. For rP5 to rP7, PheRS and Phe were also omitted and instead, the following aminoacyl-tRNA synthetases and amino acids corresponding thereto were added: 0.04 μM SerRS, 0.02 μM HisRS, 0.16 μM ProRS, 0.09 μM ThrRS, 0.03 μM ArgRS, 0.38 μM AsnRS, 0.73 μM AlaRS, 0.02 μM ValRS, 0.5 mM Ser, 0.5 mM His, 0.5 mM Pro, 0.5 mM Thr, 0.5 mM Arg, 0.5 mM Asn, 0.5 mM Ala, and 0.5 mM Val. To the translation reaction mixture was added an equivalent amount of an HBS buffer (100 mM HEPES-KOH (pH 7.6) and 300 mM NaCl) twice. The resulting mixture was mixed with 5 μL of an ANTI-FLAG M2 affinity gel (Sigma), followed by incubation at room temperature for 30 minutes. The peptides bound to the affinity gel were eluted by washing the gel twice with 25 μL of an HBS buffer (50 mM HEPES-KOH (pH 7.6) and 150 mM NaCl) and adding 20 μL of 0.2% trifluoroacetic acid. Then, the peptides were desalted using SPE C-Tip (Nikkyo Technos) and co-crystallized with α-cyano-4-hydroxycinnamic acid. Peptide calibration standard II (Bruker Daltonics), was used as external mass calibration. MALDI-TOF MS analysis was performed in a reflector/positive mode by using UltrafleXtreme (Bruker Daltonics). The aminoacyl-μhRNA was desalted with SPE C-Tip (Nikkyo Technos), cocrystallized with 3-hydroxypicolic acid, and then, analyzed in a linear/positive mode by UltrafleXtreme (Bruker Daltonics).

The conditions of the following table were applied to the preparation of aminoacyl-tRNA$^{Pro1E2}_{CGG}$.

TABLE 15

| Amino acid | Substrate | Conc. of substrate (mM) | pH | Temperature (°C) | Time (h) |
|---|---|---|---|---|---|
| Abz | Isatoic anhydride | 10 | 9.5 | 25 | 3 |
| Abz$^{5OH}$ | 5-Hydroxyisatoic anhydride | 10 | 10.5 | 25 | 1 |
| Abz$^{5OMe}$ | 5-Methoxyisatoic anhydride | 10 | 10 | 25 | 3 |
| Abz$^{5F}$ | 5-Fluoroisatoic anhydride | 8 | 10 | 25 | 3 |
| $^{3N}$Abz | $^{3N}$Ahz-CME (+eFx) | 20 | 10 | 4 | 144 |
| Apy | Apy-CME (+eFx) | 20 | 9 | 4 | 144 |
| Atp | Atp-CME (+eFx) | 20 | 9.5 | 4 | 192 |
| Atz | Atz-CME (+eFx) | 20 | 10.5 | 4 | 192 |

By introducing the respective aminoacyl-tRNA$^{Pro1E2}_{CGG}$ (Abz, Abz$^{5OH}$, Abz$^{5OMe}$, Abz$^{5F}$, Apy, Atp, and Atz) into the CCG codon of the mRNA (mR1), rP1 peptides were synthesized (FIG. 12*a*). The translation reaction was performed using a flexible in vitro translation (FIT) system including 6 amino acids ((Met, Tyr, Lys, Phe, Asp, and Gly) and aminoacyl-tRNA synthetases (ARS) corresponding thereto but lacking the other 14 amino acids and aminoacyl-tRNA synthetases thereof. The identity of the peptides was confirmed by MALDI-TOF MS and the desired m/z values of $[M+H]^+$ and $[M+2H]^{2+}$ ions without a byproduct were obtained (FIG. 12*b*). The same peptides were translated in the presence of $[^{14}C]$-labeled Asp, subjected to tricine SDS-PAGE, and then, quantified by autoradiography (FIG. 20). The rP1 expression levels in the presence of EF-P, compared with that in the absence of EF-P, was raised from 1.5 times to 7 times (FIG. 12*c*).

Next, mRNAs (mR2 to mR4) were prepared to express peptides (rP2 to rP4, FIG. 13*a*) in the presence of Abz-$tRNA^{Pro1E2}_{CGG}$ and EF-P in order to study the possibility of consecutive or multiple incorporation of Abz. The rP2 peptide has two consecutive Abz residues, while rP3 and rP4 peptides have one or two Phe residues inserted between two Abz residues. The expression of each of the peptides (rP2 to rP4) labeled with $[^{14}C]$Asp was analyzed by tricine SDS-PAGE. Discrete bands in the rP4 expression were observed with a level (0.065 vs. 0.072 pmol/μL) comparable to that of rP1 (FIG. 13*b* and FIG. 21) and the identity of rP4 peptide with the expected molecular weight was confirmed by MALDI-TOF MS spectrum (FIG. 13*c*).

Next, cyclic peptides containing a plurality of extraneous amino acids including an Abz derivative were expressed. Template mRNAs (mR5 to mR10) were designed to express peptides (rP5 to rP10) in a reprogrammed genetic code (FIG. 14*a*). The reprogramming was performed to use N-chloroacetyl-D-tyrosine ($^{ClAc}$D-Tyr) or N-chloroacetyl-D-phenylalanine ($^{ClAc}$D-Phe) as an initiator ($tRNA^{fMet}$CAU was charged with eFx/$^{ClAc}$D-Tyr-CME or eFx/$^{ClAc}$D-Phe-CME) and to introduce D-Cys at the downstream position ($tRNA^{Pro1E2}$GUG was charged with dFx/D-Cys-DBE, in which DBE was a 3,5-dinitrobenzyl ester). The ClAc group on the D-amino acid and sulfhydryl group were spontaneously cyclized via a thioether bond when the entire peptide was synthesized (FIG. 14*a*). Between those residues for cyclization, an amino acid bound to $tRNA^{Pro1E2}_{NNN}$ (NNN was an anticodon corresponding thereto) was introduced into the amino acid sequence of the peptide (rP5, rP6, or rP7) (FIG. 14*a*). As a result of the MALDI-TOF MS spectra of those peptides (rP5 to rP7) (FIG. 14*b*), it was confirmed that correct cyclic peptides were expressed. In order to express rP8 peptide, N-methyl-1-α-Ser ($^{Me}$Ser), (1S,2S)-2-ACPC, Abz, and $AbZ^{5OMe}$ were introduced using $^{Me}$Ser-$tRNA^{Pro1E2}$GAU, (1S,2S)-2-ACPC-$tRNA^{GluE2}_{CGG}$, and Abz-$tRNA^{Pro1E2}_{GAU}$ or $AbZ^{5OMe}$-$tRNA^{Pro1E2}$GGU. The MALDI-TOF MS spectrum of the rP8 peptide containing Abz or $AbZ^{5OMe}$ showed a desirable peak (FIG. 14*b*).

In the end, two Abz derivatives were incorporated into the cyclic structure of peptides (rP9 and rP10) to confirm the incorporation possibility of a plurality of Abz derivatives (FIG. 14*b*).

From the present examples, it was confirmed that one or more aromatic amino acids can be introduced into the main chain bond in the middle of the peptide sequence in the elongation process of a non-N-terminal site peptide chain. The most important advantage of the ribosomal peptide synthesis over the chemical synthesis is that since it can be confirmed that by the present invention, an aromatic amino acid-containing cyclic peptide can be expressed by the FIT system, it becomes a first step for developing a RaPID (Random Non-standard Peptides Integrated Discovery) platform of a physiologically active aromatic amino acid-containing cyclic peptide and sending a physiologically active "foldamer-like" peptide to a research program.

What is claimed is:

1. A method of producing a library including two or more cyclic peptides, wherein at least one of the cyclic peptides included in the library has a cyclic structure having 4 to 30 amino acids or derivatives thereof and comprises, in the cyclic structure, at least one selected from cyclic β-, γ-, and δ-amino acids (cAAs), comprising:

preparing an mRNA library encoding a peptide comprising a sequence represented by formula (1):

$$-(Xaa)_{n1}- \quad (1)$$

wherein each Xaa is independently an arbitrary amino acid or derivative thereof, at least one Xaa is a cyclic β-, γ-, or δ-amino acid (cAA), and n1 is an integer of 2 to 28; and using the mRNA library to express the peptide in a cell-free translation system and produce the library, wherein the peptide comprising the sequence represented by the formula (1) is represented by the following formula (2);

$$Xaa1-(Xaa)_{n1}-Xaa2-(Xaa_x)_m \quad (2)$$

wherein each Xaa is independently an arbitrary amino acid or derivative thereof, at least one Xaa is a cyclic β-, γ-, or δ-amino acid (cAA), Xaa1 and Xaa2 are each independently an amino acid or derivative thereof which forms a ring of the cyclic peptide, each $Xaa_x$ is independently an arbitrary amino acid or derivative thereof, and n1 is an integer of 2 to 28, and m is an integer of 0 to 10.

2. The method of producing a library according to claim 1, wherein the cyclic β-, γ-, or δ-amino acid is each represented by any one of the following formulas:

(I-1)

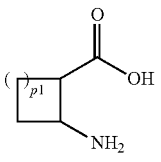

wherein p1 is any integer of 1 to 4;

(I-2)

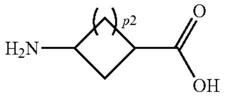

wherein p2 is any integer of 1 to 4;

(I-3)

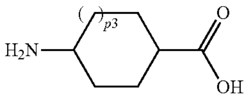

wherein p3 is an integer of 1 or 2; and $$H_2N—Ar—COOH \quad (I-4)$$

wherein Ar is a divalent aromatic group whose aromatic ring may be substituted with one or more substituents.

3. The method of producing a library according to claim 1, wherein the cAA is at least one cyclic β- or γ-amino acid (i) selected from:

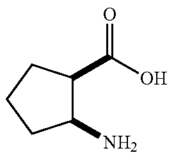

(1R,2S)-2-ACPC

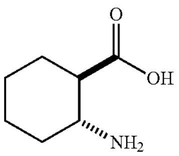

(1R,2R)-2-ACHC

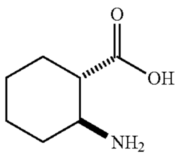

(1S,2S)-2-ACHC

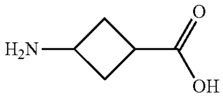

cis-3-ACBC

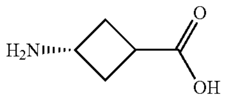

trans-3-ACBC

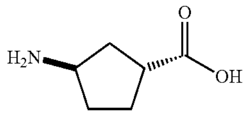

(1R,3R)-3-ACPC

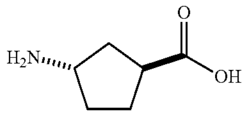

(1S,3S)-3-ACPC

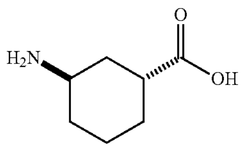

(1R,3R)-3-ACHC and/or at least one cyclic β- or γ-amino acid (ii) selected from:

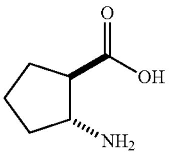

(1R,2R)-2-ACPC

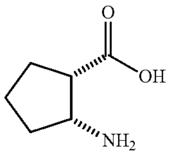

(1S,2R)-2-ACPC

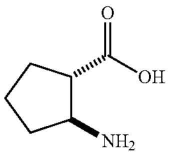

(1S,2S)-2-ACPC

-continued

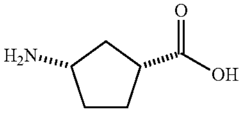

(1R,3S)-3-ACPC

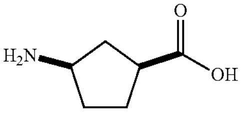

(1S,3R)-3-ACPC

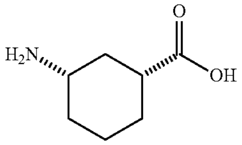

(1R,3S)-3-ACHC and the cell-free translation system comprises a tRNA charged with the cyclic β- or γ-amino acid (i) and having a D-arm structure interactive with EF-P, and/or a tRNA charged with the cyclic β- or γ-amino acid (ii) and not having a D-arm structure interactive with EF-P.

4. The method of producing a library according to claim 3, wherein the tRNA charged with the cyclic β- or γ-amino acid (i) and having a D-arm structure interactive with EF-P is $tRNA^{Pro1E2}$ and the tRNA charged with the cyclic β- or γ-amino acid (ii) and not having a D-arm structure interactive with EF-P is $tRNA^{GluE2}$.

5. The method of producing a library according to claim 1, further comprising binding puromycin to the 3' end of each of the mRNAs of the mRNA library to produce a puromycin-bound mRNA library; and using the puromycin-bound mRNA library to express the peptide in a cell-free translation system and produce a peptide-mRNA complex library.

6. The method of producing a library according to claim 1, wherein the cell-free translation system comprises a tRNA charged with an amino acid residue selected from cyclic β-, γ-, and δ-amino acids (cAAs) and the tRNA is a tRNA having a D-arm structure interactive with EF-P or a tRNA not having a D-arm structure interactive with EF-P.

7. The method of producing a library according to claim 1, wherein the cell-free translation system comprises a tRNA charged with an amino acid residue one selected from cyclic β-, γ-, and δ-amino acids (cAAs) and the tRNA is at least one selected from $tRNA^{Pro1E2}$ and $tRNA^{GluE2}$.

8. A method of producing a library including two or more cyclic peptides, wherein at least one of the cyclic peptides included in the library has a cyclic structure having 4 to 30 amino acids or derivatives thereof and comprises, in the cyclic structure, at least one selected from cyclic β-, γ-, and δ-amino acids (cAAs), comprising:

preparing an mRNA library encoding a peptide comprising a sequence represented by formula (1):

$$-(Xaa)_{n1}- \qquad (1)$$

wherein each Xaa is independently an arbitrary amino acid or derivative thereof, at least one Xaa is a cyclic β-, γ-, or δ-amino acid (cAA), and n1 is an integer of 2 to 28; and using the mRNA library to express the peptide in a cell-free translation system and produce the library, wherein the cyclic β-, γ-, or δ-amino acid is each represented by any one of the following formulas:

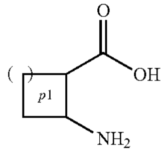

wherein p1 is any integer of 1 to 4;

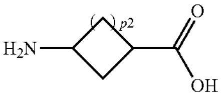

wherein p2 is any integer of 1 to 4;

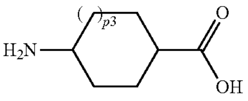

wherein p3 is an integer of 1 or 2; and wherein Ar is a divalent aromatic group whose aromatic ring may be substituted with one or more substituents.

9. The method of producing a library according to claim 8, wherein the cAA is at least one cyclic β- or γ-amino acid (i) selected from:

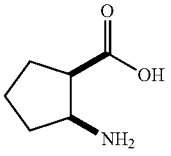

(1R,2S)-2-ACPC

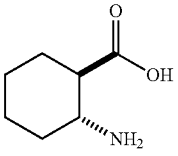

(1R,2R)-2-ACPC

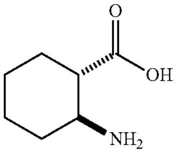

(1S,2S)-2-ACPC

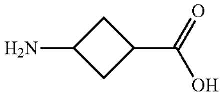

cis-3-ACBC

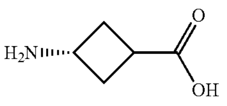

trans-3-ACBC

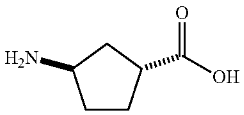

(1R,3R)-3-ACPC

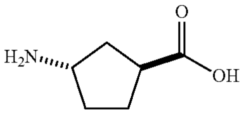

(1S,3S)-3-ACPC

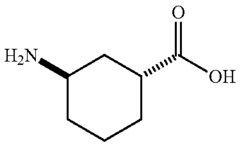

(1R,3R)-3-ACPC and/or at least one cyclic β- or γ-amino acid (ii) selected from:

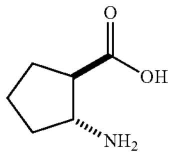

(1R,2R)-2-ACPC

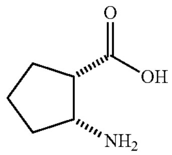

(1S,2R)-2-ACPC

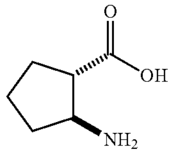

(1S,2S)-2-ACPC

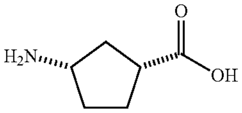

(1R,3S)-3-ACPC

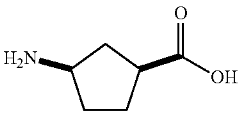

(1S,3R)-3-ACPC

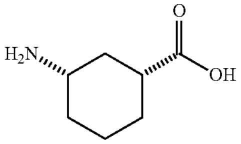

(1R,3S)-3-ACHC and the cell-free translation system comprises a tRNA charged with the cyclic β- or γ-amino acid (i) and having a D-arm structure interactive with EF-P, and/or a tRNA charged with the cyclic β- or γ-amino acid (ii) and not having a D-arm structure interactive with EF-P.

10. The method of producing a library according to claim 8, further comprising binding puromycin to the 3' end of each of the mRNAs of the mRNA library to produce a puromycin-bound mRNA library; and using the puromycin-bound mRNA library to express the peptide in a cell-free translation system and produce a peptide-mRNA complex library.

11. The method of producing a library according to claim 8, wherein the cell-free translation system comprises a tRNA charged with an amino acid residue selected from cyclic β-, γ-, and δ-amino acids (cAAs) and the tRNA is a tRNA having a D-arm structure interactive with EF-P or a tRNA not having a D-arm structure interactive with EF-P.

12. The method of producing a library according to claim 8, wherein the cell-free translation system comprises a tRNA charged with an amino acid residue one selected from cyclic β-, γ-, and δ-amino acids (cAAs) and the tRNA is at least one selected from $tRNA^{Pro1E2}$ and $tRNA^{GluE2}$.

13. The method of producing a library according to claim 8, wherein the cell-free translation system comprises a tRNA charged with the cyclic β- or γ-amino acid and having a D-arm structure interactive with EF-P, and/or a tRNA charged with the cyclic β- or γ-amino acid lacking a D-arm structure interactive with EF-P, and wherein the tRNA charged with the cyclic β- or γ-amino acid and having a D-arm structure interactive with EF-P is $tRNA^{Pro1E2}$ and the tRNA charged with the cyclic β- or γ-amino acid and lacking a D-arm structure interactive with EF-P is $tRNA^{GluE2}$.

* * * * *

SEQUENCE LISTING

```
<160> NUMBER OF SEQ ID NOS: 365

<210> SEQ ID NO 1
<211> LENGTH: 17
<212> TYPE: RNA
<213> ORGANISM: Artificial Sequence
<220> FEATURE:
<223> OTHER INFORMATION: D-arm of tRNA
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (5)..(13)
<223> OTHER INFORMATION: n is a, c, g, or u
<220> FEATURE:
<221> NAME/KEY: misc_feature
<222> LOCATION: (16)..(17)
<223> OTHER INFORMATION: n is a, c, g, or u

<400> SEQUENCE: 1

nngcnnnnnn nnngcnn                                                    17


<210> SEQ ID NO 2
<211> LENGTH: 11
<212> TYPE: RNA
<213> ORGANISM: Artificial Sequence
<220> FEATURE:
<223> OTHER INFORMATION: T-arm of tRNA
<220> FEATURE:
<221> NAME/KEY: misc_feature
<222> LOCATION: (6)..(6)
```

<223> OTHER INFORMATION: n is a, c, g, or u

<400> SEQUENCE: 2
aggggncccc u 11

<210> SEQ ID NO 3
<211> LENGTH: 17
<212> TYPE: RNA
<213> ORGANISM: Artificial Sequence
<220> FEATURE:
<223> OTHER INFORMATION: D-arm of tRNA
<220> FEATURE:
<221> NAME/KEY: misc_feature
<222> LOCATION: (5)..(13)
<223> OTHER INFORMATION: n is a, c, g, or u

<400> SEQUENCE: 3
gcgcnnnnnn nnngcgc 17

<210> SEQ ID NO 4
<211> LENGTH: 9
<212> TYPE: RNA
<213> ORGANISM: Artificial Sequence
<220> FEATURE:
<223> OTHER INFORMATION: D-loop of tRNA

<400> SEQUENCE: 4 agccuggua 9

<210> SEQ ID NO 5
<211> LENGTH: 21
<212> TYPE: RNA
<213> ORGANISM: Artificial Sequence
<220> FEATURE:
<223> OTHER INFORMATION: D-arm of tRNA
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 5
nngcgcagcc ugguagcgcn n 21

<210> SEQ ID NO 6
<211> LENGTH: 21
<212> TYPE: RNA
<213> ORGANISM: Artificial Sequence
<220> FEATURE:
<223> OTHER INFORMATION: D-arm of tRNA

<400> SEQUENCE: 6
gcgcgcagcc ugguagcgcg c 21

<210> SEQ ID NO 7
<211> LENGTH: 7
<212> TYPE: RNA
<213> ORGANISM: Artificial Sequence
<220> FEATURE:
<223> OTHER INFORMATION: T-loop of tRNA

<400> SEQUENCE: 7 uucgaau 7

<210> SEQ ID NO 8
<211> LENGTH: 46
<212> TYPE: RNA
<213> ORGANISM: Artificial Sequence
<220> FEATURE:
<223> OTHER INFORMATION: dFx

<400> SEQUENCE: 8
ggaucgaaag auuuccgcau ccccgaaagg guacauggcg uuaggu 46

<210> SEQ ID NO 9
<211> LENGTH: 45
<212> TYPE: RNA
<213> ORGANISM: Artificial Sequence
<220> FEATURE:
<223> OTHER INFORMATION: eFx

<400> SEQUENCE: 9
ggaucgaaag auuuccgcgg ccccgaaagg ggauuagcgu uaggu 45

<210> SEQ ID NO 10
<211> LENGTH: 77
<212> TYPE: RNA
<213> ORGANISM: Artificial Sequence
<220> FEATURE:
<223> OTHER INFORMATION: tRNA, Pro1E2(CAU)

<400> SEQUENCE: 10
gggugauugg cgcagccugg uagcgcacuu cgcucauaac gaagggguca gggguucgaa 60
uccccuauca cccgcca 77

<210> SEQ ID NO 11
<211> LENGTH: 77
<212> TYPE: RNA
<213> ORGANISM: Artificial Sequence
<220> FEATURE:
<223> OTHER INFORMATION: tRNA, Pro1E2(CGG)

<400> SEQUENCE: 11
gggugauugg cgcagccugg uagcgcacuu cguucgggac gaagggguca gggguucgaa 60
uccccuauca cccgcca 77

<210> SEQ ID NO 12
<211> LENGTH: 77
<212> TYPE: RNA
<213> ORGANISM: Artificial Sequence
<220> FEATURE:
<223> OTHER INFORMATION: tRNA, Pro1E2(GAU)

<400> SEQUENCE: 12
gggugauugg cgcagccugg uagcgcacuu cgcugauaac gaagggguca gggguucgaa 60
uccccuauca cccgcca 77

<210> SEQ ID NO 13
<211> LENGTH: 77
<212> TYPE: RNA
<213> ORGANISM: Artificial Sequence
<220> FEATURE:
<223> OTHER INFORMATION: tRNA, Pro1E2(GUG)

<400> SEQUENCE: 13
gggugauugg cgcagccugg uagcgcacuu cguugugaac gaagggguca gggguucgaa 60
uccccuauca cccgcca 77

-continued

<210> SEQ ID NO 14
<211> LENGTH: 76
<212> TYPE: RNA
<213> ORGANISM: Artificial Sequence
<220> FEATURE:
<223> OTHER INFORMATION: tRNA, GluE2(GAU)

<400> SEQUENCE: 14
guccccuucg ucuagaggcc caggacaccg cccugauaag gcgguaacag ggguucgaau 60
ccccuagggg acgcca 76

<210> SEQ ID NO 15
<211> LENGTH: 76
<212> TYPE: RNA
<213> ORGANISM: Artificial Sequence
<220> FEATURE:
<223> OTHER INFORMATION: tRNA, GluE2(GCA)

<400> SEQUENCE: 15
guccccuucg ucuagaggcc caggacaccg cccugcaaag gcgguaacag ggguucgaau 60
ccccuagggg acgcca 76

<210> SEQ ID NO 16
<211> LENGTH: 76
<212> TYPE: RNA
<213> ORGANISM: Artificial Sequence
<220> FEATURE:
<223> OTHER INFORMATION: tRNA, GluE2(GGU)

<400> SEQUENCE: 16
guccccuucg ucuagaggcc caggacaccg ccuugguaag gcgguaacag ggguucgaau 60
ccccuagggg acgcca 76

<210> SEQ ID NO 17
<211> LENGTH: 76
<212> TYPE: RNA
<213> ORGANISM: Artificial Sequence
<220> FEATURE:
<223> OTHER INFORMATION: tRNA, GluE2(GUG)

<400> SEQUENCE: 17
guccccuucg ucuagaggcc caggacaccg ccuugugaag gcgguaacag ggguucgaau 60
ccccuagggg acgcca 76

<210> SEQ ID NO 18
<211> LENGTH: 77
<212> TYPE: RNA
<213> ORGANISM: Artificial Sequence
<220> FEATURE:
<223> OTHER INFORMATION: tRNA, fMet(CAU)

<400> SEQUENCE: 18
cgcggggugg agcagccugg uagcucgucg ggcucauaac ccgaagaucg ucgguucaaa 60 uccggcccccc gcaacca 77

<210> SEQ ID NO 19
<211> LENGTH: 36
<212> TYPE: DNA
<213> ORGANISM: Artificial Sequence
<220> FEATURE:
<223> OTHER INFORMATION: Extension primer (forward) for dFx

<400> SEQUENCE: 19
gtaatacgac tcactatagg atcgaaagat ttccgc 36

<210> SEQ ID NO 20
<211> LENGTH: 36
<212> TYPE: DNA
<213> ORGANISM: Artificial Sequence
<220> FEATURE:
<223> OTHER INFORMATION: Extension primer (forward) for eFx

<400> SEQUENCE: 20
gtaatacgac tcactatagg atcgaaagat ttccgc 36

<210> SEQ ID NO 21
<211> LENGTH: 50
<212> TYPE: DNA
<213> ORGANISM: Artificial Sequence
<220> FEATURE:
<223> OTHER INFORMATION: Extension primer (forward) for tRNA, Pro1E2(CAU)

<400> SEQUENCE: 21
gtaatacgac tcactatagg gtgattggcg cagcctggta gcgcacttcg 50

<210> SEQ ID NO 22
<211> LENGTH: 50
<212> TYPE: DNA
<213> ORGANISM: Artificial Sequence
<220> FEATURE:
<223> OTHER INFORMATION: Extension primer (forward) for tRNA, Pro1E2(CGG)

<400> SEQUENCE: 22
gtaatacgac tcactatagg gtgattggcg cagcctggta gcgcacttcg 50

<210> SEQ ID NO 23
<211> LENGTH: 50
<212> TYPE: DNA
<213> ORGANISM: Artificial Sequence
<220> FEATURE:
<223> OTHER INFORMATION: Extension primer (forward) for tRNA, Pro1E2(GAU)

<400> SEQUENCE: 23
gtaatacgac tcactatagg gtgattggcg cagcctggta gcgcacttcg 50

<210> SEQ ID NO 24
<211> LENGTH: 50
<212> TYPE: DNA
<213> ORGANISM: Artificial Sequence
<220> FEATURE:
<223> OTHER INFORMATION: Extension primer (forward) for tRNA, Pro1E2(GUG)

<400> SEQUENCE: 24
gtaatacgac tcactatagg gtgattggcg cagcctggta gcgcacttcg 50

<210> SEQ ID NO 25
<211> LENGTH: 64
<212> TYPE: DNA
<213> ORGANISM: Artificial Sequence
<220> FEATURE:
<223> OTHER INFORMATION: Extension primer (forward) for tRNA, GluE2(GAU)

<400> SEQUENCE: 25
cactatagtc cccttcgtct agaggcccag gacaccgccc tgataaggcg gtaacagggg 60
ttcg 64

<210> SEQ ID NO 26
<211> LENGTH: 64
<212> TYPE: DNA
<213> ORGANISM: Artificial Sequence
<220> FEATURE:
<223> OTHER INFORMATION: Extension primer (forward) for tRNA, GluE2(GCA)

<400> SEQUENCE: 26
cactatagtc cccttcgtct agaggcccag gacaccgccc tgcaaaggcg gtaacagggg 60
ttcg 64

<210> SEQ ID NO 27
<211> LENGTH: 64
<212> TYPE: DNA
<213> ORGANISM: Artificial Sequence
<220> FEATURE:
<223> OTHER INFORMATION: Extension primer (forward) for tRNA, GluE2(GGU)

<400> SEQUENCE: 27
cactatagtc cccttcgtct agaggcccag gacaccgcct tggtaaggcg gtaacagggg 60
ttcg 64

<210> SEQ ID NO 28
<211> LENGTH: 64
<212> TYPE: DNA
<213> ORGANISM: Artificial Sequence
<220> FEATURE:
<223> OTHER INFORMATION: Extension primer (forward) for tRNA, GluE2(GUG)

<400> SEQUENCE: 28
cactatagtc cccttcgtct agaggcccag gacaccgcct tgtgaaggcg gtaacagggg 60
ttcg 64

<210> SEQ ID NO 29
<211> LENGTH: 68
<212> TYPE: DNA
<213> ORGANISM: Artificial Sequence
<220> FEATURE:
<223> OTHER INFORMATION: Extension primer (forward) for tRNA, fMet(CAU)

<400> SEQUENCE: 29
gtaatacgac tcactatacg cggggtggag cagcctggta gctcgtcggg ctcataaccc 60
gaagatcg 68

<210> SEQ ID NO 30
<211> LENGTH: 46
<212> TYPE: DNA
<213> ORGANISM: Artificial Sequence
<220> FEATURE:
<223> OTHER INFORMATION: Extension primer (reverse) for dFx

<400> SEQUENCE: 30
acctaacgcc atgtaccctt tcggggatgc ggaaatcttt cgatcc 46

<210> SEQ ID NO 31
<211> LENGTH: 45
<212> TYPE: DNA

-continued

```
<213> ORGANISM: Artificial Sequence
<220> FEATURE:
<223> OTHER INFORMATION: Extension primer (reverse) for eFx

<400> SEQUENCE: 31

acctaacgct aatccccttt cggggccgcg gaaatctttc gatcc                     45


<210> SEQ ID NO 32
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E2(CAU)

<400> SEQUENCE: 32

tggcgggtga taggggattc gaacccctga ccccttcgtt atgagcgaag tgcgctacca     60

gg                                                                    62


<210> SEQ ID NO 33
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E2(CGG)

<400> SEQUENCE: 33

tggcgggtga taggggattc gaacccctga ccccttcgtc ccgaacgaag tgcgctacca     60

gg                                                                    62


<210> SEQ ID NO 34
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E2(GAU)

<400> SEQUENCE: 34

tggcgggtga taggggattc gaacccctga ccccttcgtt atcagcgaag tgcgctacca     60

gg                                                                    62


<210> SEQ ID NO 35
<211> LENGTH: 62
<212> TYPE: DNA
<213> ORGANISM: Artificial Sequence
<220> FEATURE:
<223> OTHER INFORMATION: Extension primer (reverse) for tRNA,
      Pro1E2(GUG)

<400> SEQUENCE: 35

tggcgggtga tagaggattc gaacctccga ccccttcgtt cacaacgaag tgcgctacca     60

gg                                                                    62


<210> SEQ ID NO 36
<211> LENGTH: 37
<212> TYPE: DNA
<213> ORGANISM: Artificial Sequence
<220> FEATURE:
<223> OTHER INFORMATION: Extension primer (reverse) for tRNA, GluE2(GAU)

<400> SEQUENCE: 36

tggcgtcccc taggggattc gaacccctgt taccgcc                              37
```

-continued

<210> SEQ ID NO 37
<211> LENGTH: 37
<212> TYPE: DNA
<213> ORGANISM: Artificial Sequence
<220> FEATURE:
<223> OTHER INFORMATION: Extension primer (reverse) for tRNA, GluE2(GCA)

<400> SEQUENCE: 37
tggcgtcccc taggggattc gaacccctgt taccgcc 37

<210> SEQ ID NO 38
<211> LENGTH: 37
<212> TYPE: DNA
<213> ORGANISM: Artificial Sequence
<220> FEATURE:
<223> OTHER INFORMATION: Extension primer (reverse) for tRNA, GluE2(GGU)

<400> SEQUENCE: 38
tggcgtcccc taggggattc gaacccctgt taccgcc 37

<210> SEQ ID NO 39
<211> LENGTH: 37
<212> TYPE: DNA
<213> ORGANISM: Artificial Sequence
<220> FEATURE:
<223> OTHER INFORMATION: Extension primer (reverse) for tRNA, GluE2(GUG)

<400> SEQUENCE: 39
tggcgtcccc taggggattc gaacccctgt taccgcc 37

<210> SEQ ID NO 40
<211> LENGTH: 46
<212> TYPE: DNA
<213> ORGANISM: Artificial Sequence
<220> FEATURE:
<223> OTHER INFORMATION: Extension primer (reverse) for tRNA, fMet(CAU)

<400> SEQUENCE: 40
tggttgcggg ggccggattt gaaccgacga tcttcgggtt atgagc 46

<210> SEQ ID NO 41
<211> LENGTH: 22
<212> TYPE: DNA
<213> ORGANISM: Artificial Sequence
<220> FEATURE:
<223> OTHER INFORMATION: PCT primer (forward) for dFx

<400> SEQUENCE: 41
ggcgtaatac gactcactat ag 22

<210> SEQ ID NO 42
<211> LENGTH: 22
<212> TYPE: DNA
<213> ORGANISM: Artificial Sequence
<220> FEATURE:
<223> OTHER INFORMATION: PCT primer (forward) for eFx

<400> SEQUENCE: 42
ggcgtaatac gactcactat ag 22

<210> SEQ ID NO 43
<211> LENGTH: 22
<212> TYPE: DNA
<213> ORGANISM: Artificial Sequence
<220> FEATURE:

<223> OTHER INFORMATION: PCT primer (forward) for tRNA, Pro1E2(CAU)

<400> SEQUENCE: 43
ggcgtaatac gactcactat ag 22

<210> SEQ ID NO 44
<211> LENGTH: 22
<212> TYPE: DNA
<213> ORGANISM: Artificial Sequence
<220> FEATURE:
<223> OTHER INFORMATION: PCT primer (forward) for tRNA, Pro1E2(CGG)

<400> SEQUENCE: 44
ggcgtaatac gactcactat ag 22

<210> SEQ ID NO 45
<211> LENGTH: 22
<212> TYPE: DNA
<213> ORGANISM: Artificial Sequence
<220> FEATURE:
<223> OTHER INFORMATION: PCT primer (forward) for tRNA, Pro1E2(GAU)

<400> SEQUENCE: 45
ggcgtaatac gactcactat ag 22

<210> SEQ ID NO 46
<211> LENGTH: 22
<212> TYPE: DNA
<213> ORGANISM: Artificial Sequence
<220> FEATURE:
<223> OTHER INFORMATION: PCT primer (forward) for tRNA, Pro1E2(GUG)

<400> SEQUENCE: 46
ggcgtaatac gactcactat ag 22

<210> SEQ ID NO 47
<211> LENGTH: 33
<212> TYPE: DNA
<213> ORGANISM: Artificial Sequence
<220> FEATURE:
<223> OTHER INFORMATION: PCT primer (forward) for tRNA, GluE2(GAU)

<400> SEQUENCE: 47
gtaatacgac tcactatagt ccccttcgtc tag 33

<210> SEQ ID NO 48
<211> LENGTH: 33
<212> TYPE: DNA
<213> ORGANISM: Artificial Sequence
<220> FEATURE:
<223> OTHER INFORMATION: PCT primer (forward) for tRNA, GluE2(GCA)

<400> SEQUENCE: 48
gtaatacgac tcactatagt ccccttcgtc tag 33

<210> SEQ ID NO 49
<211> LENGTH: 33
<212> TYPE: DNA
<213> ORGANISM: Artificial Sequence
<220> FEATURE:
<223> OTHER INFORMATION: PCT primer (forward) for tRNA, GluE2(GGU)

<400> SEQUENCE: 49
gtaatacgac tcactatagt ccccttcgtc tag 33

<210> SEQ ID NO 50
<211> LENGTH: 33
<212> TYPE: DNA
<213> ORGANISM: Artificial Sequence
<220> FEATURE:
<223> OTHER INFORMATION: PCT primer (forward) for tRNA, GluE2(GUG)

<400> SEQUENCE: 50
gtaatacgac tcactatagt ccccttcgtc tag 33

<210> SEQ ID NO 51
<211> LENGTH: 22
<212> TYPE: DNA
<213> ORGANISM: Artificial Sequence
<220> FEATURE:
<223> OTHER INFORMATION: PCT primer (forward) for tRNA, fMet(CAU)

<400> SEQUENCE: 51
ggcgtaatac gactcactat ac 22

<210> SEQ ID NO 52
<211> LENGTH: 19
<212> TYPE: DNA
<213> ORGANISM: Artificial Sequence
<220> FEATURE:
<223> OTHER INFORMATION: PCT primer (reverse) for dFx

<400> SEQUENCE: 52
acctaacgcc atgtaccct 19

<210> SEQ ID NO 53
<211> LENGTH: 18
<212> TYPE: DNA
<213> ORGANISM: Artificial Sequence
<220> FEATURE:
<223> OTHER INFORMATION: PCT primer (reverse) for eFx

<400> SEQUENCE: 53
acctaacgct aatcccct 18

<210> SEQ ID NO 54
<211> LENGTH: 20
<212> TYPE: DNA
<213> ORGANISM: Artificial Sequence
<220> FEATURE:
<223> OTHER INFORMATION: PCT primer (reverse) for tRNA, Pro1E2(CAU)
<220> FEATURE:
<221> NAME/KEY: misc_feature
<222> LOCATION: (2)..(2)
<223> OTHER INFORMATION: gm

<400> SEQUENCE: 54
tggcgggtga taggggattc 20

<210> SEQ ID NO 55
<211> LENGTH: 20
<212> TYPE: DNA
<213> ORGANISM: Artificial Sequence
<220> FEATURE:
<223> OTHER INFORMATION: PCT primer (reverse) for tRNA, Pro1E2(CGG)
<220> FEATURE:
<221> NAME/KEY: misc_feature
<222> LOCATION: (2)..(2)
<223> OTHER INFORMATION: gm

<400> SEQUENCE: 55
tggcgggtga taggggattc 20

<210> SEQ ID NO 56
<211> LENGTH: 20
<212> TYPE: DNA
<213> ORGANISM: Artificial Sequence
<220> FEATURE:
<223> OTHER INFORMATION: PCT primer (reverse) for tRNA, Pro1E2(GAU)
<220> FEATURE:
<221> NAME/KEY: misc_feature
<222> LOCATION: (2)..(2)
<223> OTHER INFORMATION: gm

<400> SEQUENCE: 56
tggcgggtga taggggattc 20

<210> SEQ ID NO 57
<211> LENGTH: 20
<212> TYPE: DNA
<213> ORGANISM: Artificial Sequence
<220> FEATURE:
<223> OTHER INFORMATION: PCT primer (reverse) for tRNA, Pro1E2(GUG)
<220> FEATURE:
<221> NAME/KEY: misc_feature
<222> LOCATION: (2)..(2)
<223> OTHER INFORMATION: gm

<400> SEQUENCE: 57
tggcgggtga taggggattc 20

<210> SEQ ID NO 58
<211> LENGTH: 20
<212> TYPE: DNA
<213> ORGANISM: Artificial Sequence
<220> FEATURE:
<223> OTHER INFORMATION: PCT primer (reverse) for tRNA, GluE2(GAU)
<220> FEATURE:
<221> NAME/KEY: misc_feature
<222> LOCATION: (2)..(2)
<223> OTHER INFORMATION: gm

<400> SEQUENCE: 58
tggcgtcccc taggggattc 20

<210> SEQ ID NO 59
<211> LENGTH: 20
<212> TYPE: DNA
<213> ORGANISM: Artificial Sequence
<220> FEATURE:
<223> OTHER INFORMATION: PCT primer (reverse) for tRNA, GluE2(GCA)
<220> FEATURE:
<221> NAME/KEY: misc_feature
<222> LOCATION: (2)..(2)
<223> OTHER INFORMATION: gm

<400> SEQUENCE: 59
tggcgtcccc taggggattc 20

<210> SEQ ID NO 60
<211> LENGTH: 20
<212> TYPE: DNA
<213> ORGANISM: Artificial Sequence
<220> FEATURE:
<223> OTHER INFORMATION: PCT primer (reverse) for tRNA, GluE2(GGU)
<220> FEATURE:
<221> NAME/KEY: misc_feature
<222> LOCATION: (2)..(2)
<223> OTHER INFORMATION: gm

<400> SEQUENCE: 60
tggcgtcccc taggggattc 20

<210> SEQ ID NO 61
<211> LENGTH: 20
<212> TYPE: DNA
<213> ORGANISM: Artificial Sequence
<220> FEATURE:
<223> OTHER INFORMATION: PCT primer (reverse) for tRNA, GluE2(GUG)
<220> FEATURE:
<221> NAME/KEY: misc_feature
<222> LOCATION: (2)..(2)
<223> OTHER INFORMATION: gm

<400> SEQUENCE: 61
tggcgtcccc taggggattc 20

<210> SEQ ID NO 62
<211> LENGTH: 17
<212> TYPE: DNA
<213> ORGANISM: Artificial Sequence
<220> FEATURE:
<223> OTHER INFORMATION: PCT primer (reverse) for tRNA, fMet(CAU)
<220> FEATURE:
<221> NAME/KEY: misc_feature
<222> LOCATION: (2)..(2)
<223> OTHER INFORMATION: gm

<400> SEQUENCE: 62
tggttgcggg ggccgga 17

<210> SEQ ID NO 63
<211> LENGTH: 11
<212> TYPE: PRT
<213> ORGANISM: Artificial Sequence
<220> FEATURE:
<223> OTHER INFORMATION: partial structure of cyclic peptide f1
<220> FEATURE:
<221> NAME/KEY: MISC_FEATURE
<222> LOCATION: (7)..(7)
<223> OTHER INFORMATION: beta-cyclic amino acid

<400> SEQUENCE: 63

Asn Asp Arg Ser Thr Arg Xaa Arg Leu Val Ala
1               5                   10

<210> SEQ ID NO 64
<211> LENGTH: 11
<212> TYPE: PRT
<213> ORGANISM: Artificial Sequence
<220> FEATURE:
<223> OTHER INFORMATION: partial structure of cyclic peptide f2
<220> FEATURE:
<221> NAME/KEY: MISC_FEATURE
<222> LOCATION: (6)..(6)
<223> OTHER INFORMATION: beta-cyclic amino acid

<400> SEQUENCE: 64

Pro Arg Leu Phe Asn Xaa Ser Tyr Leu Arg Arg
1               5                   10

<210> SEQ ID NO 65
<211> LENGTH: 15
<212> TYPE: PRT
<213> ORGANISM: Artificial Sequence
<220> FEATURE:
<223> OTHER INFORMATION: partial structure of cyclic peptide f3
<220> FEATURE:
<221> NAME/KEY: MISC_FEATURE
<222> LOCATION: (7)..(7)
<223> OTHER INFORMATION: beta-cyclic amino acid
<220> FEATURE:

<221> NAME/KEY: MISC_FEATURE
<222> LOCATION: (12)..(12)
<223> OTHER INFORMATION: beta-cyclic amino acid

<400> SEQUENCE: 65

Phe Ala Tyr Asp Arg Arg Xaa Leu Ser Asn Asn Xaa Arg Asn Thr
1               5                   10                  15

<210> SEQ ID NO 66
<211> LENGTH: 11
<212> TYPE: PRT
<213> ORGANISM: Artificial Sequence
<220> FEATURE:
<223> OTHER INFORMATION: partial structure of cyclic peptide f4
<220> FEATURE:
<221> NAME/KEY: MISC_FEATURE
<222> LOCATION: (4)..(4)
<223> OTHER INFORMATION: beta-cyclic amino acid
<220> FEATURE:
<221> NAME/KEY: MISC_FEATURE
<222> LOCATION: (9)..(9)
<223> OTHER INFORMATION: beta-cyclic amino acid

<400> SEQUENCE: 66

Arg Tyr Thr Xaa Asn Arg Leu Phe Xaa Asn Ala
1               5                   10

<210> SEQ ID NO 67
<211> LENGTH: 13
<212> TYPE: PRT
<213> ORGANISM: Artificial Sequence
<220> FEATURE:
<223> OTHER INFORMATION: partial structure of cyclic peptide F1
<220> FEATURE:
<221> NAME/KEY: MISC_FEATURE
<222> LOCATION: (8)..(8)
<223> OTHER INFORMATION: beta-cyclic amino acid

<400> SEQUENCE: 67

Tyr Asn Asp Arg Ser Thr Arg Xaa Arg Leu Val Ala Cys
1               5                   10

<210> SEQ ID NO 68
<211> LENGTH: 13
<212> TYPE: PRT
<213> ORGANISM: Artificial Sequence
<220> FEATURE:
<223> OTHER INFORMATION: partial structure of cyclic peptide F2
<220> FEATURE:
<221> NAME/KEY: MISC_FEATURE
<222> LOCATION: (7)..(7)
<223> OTHER INFORMATION: beta-cyclic amino acid

<400> SEQUENCE: 68

Tyr Pro Arg Leu Phe Asn Xaa Ser Tyr Leu Arg Arg Cys
1               5                   10

<210> SEQ ID NO 69
<211> LENGTH: 17
<212> TYPE: PRT
<213> ORGANISM: Artificial Sequence
<220> FEATURE:
<223> OTHER INFORMATION: partial structure of cyclic peptide F3
<220> FEATURE:
<221> NAME/KEY: MISC_FEATURE
<222> LOCATION: (8)..(8)
<223> OTHER INFORMATION: beta-cyclic amino acid
<220> FEATURE:
<221> NAME/KEY: MISC_FEATURE
<222> LOCATION: (13)..(13)
<223> OTHER INFORMATION: beta-cyclic amino acid

<400> SEQUENCE: 69

Tyr Phe Ala Tyr Asp Arg Arg Xaa Leu Ser Asn Asn Xaa Arg Asn Thr
1 5 10 15

Cys

<210> SEQ ID NO 70
<211> LENGTH: 13
<212> TYPE: PRT
<213> ORGANISM: Artificial Sequence
<220> FEATURE:
<223> OTHER INFORMATION: partial structure of cyclic peptide F4
<220> FEATURE:
<221> NAME/KEY: misc_feature
<222> LOCATION: (5)..(5)
<223> OTHER INFORMATION: beta-cyclic amino acid
<220> FEATURE:
<221> NAME/KEY: misc_feature
<222> LOCATION: (10)..(10)
<223> OTHER INFORMATION: beta-cyclic amino acid

<400> SEQUENCE: 70

Tyr Arg Tyr Thr Xaa Asn Arg Leu Phe Xaa Asn Ala Cys
1 5 10

<210> SEQ ID NO 71
<211> LENGTH: 10
<212> TYPE: PRT
<213> ORGANISM: Artificial Sequence
<220> FEATURE:
<223> OTHER INFORMATION: partial structure of cyclic peptide i1-1
<220> FEATURE:
<221> NAME/KEY: MISC_FEATURE
<222> LOCATION: (5)..(5)
<223> OTHER INFORMATION: beta-cyclic amino acid

<400> SEQUENCE: 71

Phe Gly Val Arg Xaa Phe Tyr Asn Arg Thr
1 5 10

<210> SEQ ID NO 72
<211> LENGTH: 10
<212> TYPE: PRT
<213> ORGANISM: Artificial Sequence
<220> FEATURE:
<223> OTHER INFORMATION: partial structure of cyclic peptide i1-2
<220> FEATURE:
<221> NAME/KEY: MISC_FEATURE
<222> LOCATION: (5)..(5)
<223> OTHER INFORMATION: beta-cyclic amino acid

<400> SEQUENCE: 72

Val Gly Leu Asn Xaa Ser Leu Asn Arg Thr
1 5 10

<210> SEQ ID NO 73
<211> LENGTH: 12
<212> TYPE: PRT
<213> ORGANISM: Artificial Sequence
<220> FEATURE:
<223> OTHER INFORMATION: partial structure of cyclic peptide i1-3
<220> FEATURE:
<221> NAME/KEY: MISC_FEATURE
<222> LOCATION: (5)..(5)
<223> OTHER INFORMATION: beta-cyclic amino acid

<400> SEQUENCE: 73

Phe Ser Leu Arg Xaa Ser Phe Asn Arg Ser Arg Gly
1 5 10

<210> SEQ ID NO 74
<211> LENGTH: 10
<212> TYPE: PRT
<213> ORGANISM: Artificial Sequence
<220> FEATURE:
<223> OTHER INFORMATION: partial structure of cyclic peptide i1-4
<220> FEATURE:
<221> NAME/KEY: MISC_FEATURE
<222> LOCATION: (5)..(5)
<223> OTHER INFORMATION: beta-cyclic amino acid
<220> FEATURE:
<221> NAME/KEY: MISC_FEATURE
<222> LOCATION: (7)..(7)
<223> OTHER INFORMATION: beta-cyclic amino acid

<400> SEQUENCE: 74

Phe Ala Leu Asn Xaa Arg Xaa Asn Arg Arg
1               5                   10

<210> SEQ ID NO 75
<211> LENGTH: 10
<212> TYPE: PRT
<213> ORGANISM: Artificial Sequence
<220> FEATURE:
<223> OTHER INFORMATION: partial structure of cyclic peptide i1-5
<220> FEATURE:
<221> NAME/KEY: MISC_FEATURE
<222> LOCATION: (4)..(4)
<223> OTHER INFORMATION: beta-cyclic amino acid
<220> FEATURE:
<221> NAME/KEY: MISC_FEATURE
<222> LOCATION: (5)..(5)
<223> OTHER INFORMATION: beta-cyclic amino acid

<400> SEQUENCE: 75

Phe Gly Val Xaa Xaa Phe Tyr Asn Arg Thr
1               5                   10

<210> SEQ ID NO 76
<211> LENGTH: 14
<212> TYPE: PRT
<213> ORGANISM: Artificial Sequence
<220> FEATURE:
<223> OTHER INFORMATION: partial structure of cyclic peptide i1-6
<220> FEATURE:
<221> NAME/KEY: MISC_FEATURE
<222> LOCATION: (6)..(6)
<223> OTHER INFORMATION: beta-cyclic amino acid
<220> FEATURE:
<221> NAME/KEY: MISC_FEATURE
<222> LOCATION: (13)..(13)
<223> OTHER INFORMATION: beta-cyclic amino acid

<400> SEQUENCE: 76

Pro Arg Tyr Asn Leu Xaa Gly Ala Ser Pro Arg Phe Xaa Asn
1               5                   10

<210> SEQ ID NO 77
<211> LENGTH: 12
<212> TYPE: PRT
<213> ORGANISM: Artificial Sequence
<220> FEATURE:
<223> OTHER INFORMATION: partial structure of cyclic peptide I1-1
<220> FEATURE:
<221> NAME/KEY: MISC_FEATURE
<222> LOCATION: (6)..(6)
<223> OTHER INFORMATION: beta-cyclic amino acid

<400> SEQUENCE: 77

Tyr Phe Gly Val Arg Xaa Phe Tyr Asn Arg Thr Cys
1 5 10

<210> SEQ ID NO 78
<211> LENGTH: 12
<212> TYPE: PRT
<213> ORGANISM: Artificial Sequence
<220> FEATURE:
<223> OTHER INFORMATION: partial structure of cyclic peptide I1-2
<220> FEATURE:
<221> NAME/KEY: MISC_FEATURE
<222> LOCATION: (6)..(6)
<223> OTHER INFORMATION: beta-cyclic amino acid

<400> SEQUENCE: 78

Tyr Val Gly Leu Asn Xaa Ser Leu Asn Arg Thr Cys
1 5 10

<210> SEQ ID NO 79
<211> LENGTH: 13
<212> TYPE: PRT
<213> ORGANISM: Artificial Sequence
<220> FEATURE:
<223> OTHER INFORMATION: partial structure of cyclic peptide I1-3
<220> FEATURE:
<221> NAME/KEY: MISC_FEATURE
<222> LOCATION: (6)..(6)
<223> OTHER INFORMATION: beta-cyclic amino acid

<400> SEQUENCE: 79

Tyr Phe Ser Leu Arg Xaa Ser Phe Asn Arg Ser Arg Gly
1 5 10

<210> SEQ ID NO 80
<211> LENGTH: 12
<212> TYPE: PRT
<213> ORGANISM: Artificial Sequence
<220> FEATURE:
<223> OTHER INFORMATION: partial structure of cyclic peptide I1-4
<220> FEATURE:
<221> NAME/KEY: MISC_FEATURE
<222> LOCATION: (6)..(6)
<223> OTHER INFORMATION: beta-cyclic amino acid
<220> FEATURE:
<221> NAME/KEY: MISC_FEATURE
<222> LOCATION: (8)..(8)
<223> OTHER INFORMATION: beta-cyclic amino acid

<400> SEQUENCE: 80

Tyr Phe Ala Leu Asn Xaa Arg Xaa Asn Arg Arg Cys
1 5 10

<210> SEQ ID NO 81
<211> LENGTH: 12
<212> TYPE: PRT
<213> ORGANISM: Artificial Sequence
<220> FEATURE:
<223> OTHER INFORMATION: partial structure of cyclic peptide I1-5
<220> FEATURE:
<221> NAME/KEY: MISC_FEATURE
<222> LOCATION: (5)..(5)
<223> OTHER INFORMATION: beta-cyclic amino acid
<220> FEATURE:
<221> NAME/KEY: MISC_FEATURE
<222> LOCATION: (6)..(6)
<223> OTHER INFORMATION: beta-cyclic amino acid

<400> SEQUENCE: 81

Tyr Phe Gly Val Xaa Xaa Phe Tyr Asn Arg Thr Cys
1 5 10

<210> SEQ ID NO 82
<211> LENGTH: 16
<212> TYPE: PRT
<213> ORGANISM: Artificial Sequence
<220> FEATURE:
<223> OTHER INFORMATION: partial structure of cyclic peptide I1-6
<220> FEATURE:
<221> NAME/KEY: MISC_FEATURE
<222> LOCATION: (7)..(7)
<223> OTHER INFORMATION: beta-cyclic amino acid
<220> FEATURE:
<221> NAME/KEY: MISC_FEATURE
<222> LOCATION: (14)..(14)
<223> OTHER INFORMATION: beta-cyclic amino acid

<400> SEQUENCE: 82

Tyr Pro Arg Tyr Asn Leu Xaa Gly Ala Ser Pro Arg Phe Xaa Asn Cys
1 5 10 15

<210> SEQ ID NO 83
<211> LENGTH: 63
<212> TYPE: RNA
<213> ORGANISM: Artificial Sequence
<220> FEATURE:
<223> OTHER INFORMATION: mRNA (mR1)

<400> SEQUENCE: 83
auguacaaga aguacaaaaa guacaaaccg gguggugacu acaaggacga cgacgacaag 60
uaa 63

<210> SEQ ID NO 84
<211> LENGTH: 63
<212> TYPE: RNA
<213> ORGANISM: Artificial Sequence
<220> FEATURE:
<223> OTHER INFORMATION: mRNA (mR2)

<400> SEQUENCE: 84
auguacaaga aguacaaaaa guacaaaccg ccgggugacu acaaggacga cgacgacaag 60
uaa 63

<210> SEQ ID NO 85
<211> LENGTH: 63
<212> TYPE: RNA
<213> ORGANISM: Artificial Sequence
<220> FEATURE:
<223> OTHER INFORMATION: mRNA (mR3)

<400> SEQUENCE: 85
auguacaaga aguacaaaaa guacaaaccg ccgccggacu acaaggacga cgacgacaag 60
uaa 63

<210> SEQ ID NO 86
<211> LENGTH: 66
<212> TYPE: RNA
<213> ORGANISM: Artificial Sequence
<220> FEATURE:
<223> OTHER INFORMATION: mRNA (mR4)

<400> SEQUENCE: 86
auguacaaga aguacaaaaa guacaaaccg ccgccgccgg acuacaagga cgacgacgac 60
aaguaa 66

<210> SEQ ID NO 87
<211> LENGTH: 69
<212> TYPE: RNA
<213> ORGANISM: Artificial Sequence
<220> FEATURE:
<223> OTHER INFORMATION: mRNA (mR5)

<400> SEQUENCE: 87
auguacaaga aguacaaaaa guacaaaccg ccgccgccgc cggacuacaa ggacgacgac 60
gacaaguaa 69

<210> SEQ ID NO 88
<211> LENGTH: 72
<212> TYPE: RNA
<213> ORGANISM: Artificial Sequence
<220> FEATURE:
<223> OTHER INFORMATION: mRNA (mR6)

<400> SEQUENCE: 88
auguacaaga aguacaaaaa guacaaaccg ccgccgccgc cgccggacua caaggacgac 60
gacgacaagu aa 72

<210> SEQ ID NO 89
<211> LENGTH: 75
<212> TYPE: RNA
<213> ORGANISM: Artificial Sequence
<220> FEATURE:
<223> OTHER INFORMATION: mRNA (mR7)

<400> SEQUENCE: 89
auguacaaga aguacaaaaa guacaaaccg ccgccgccgc cgccgccgga cuacaaggac 60
gacgacgaca aguaa 75

<210> SEQ ID NO 90
<211> LENGTH: 78
<212> TYPE: RNA
<213> ORGANISM: Artificial Sequence
<220> FEATURE:
<223> OTHER INFORMATION: mRNA (mR8)

<400> SEQUENCE: 90
auguacaaga aguacaaaaa guacaaaccg ccgccgccgc cgccgccgcc ggacuacaag 60
gacgacgacg acaaguaa 78

<210> SEQ ID NO 91
<211> LENGTH: 81
<212> TYPE: RNA
<213> ORGANISM: Artificial Sequence
<220> FEATURE:
<223> OTHER INFORMATION: mRNA (mR9)

<400> SEQUENCE: 91
auguacaaga aguacaaaaa guacaaaccg ccgccgccgc cgccgccgcc gccggacuac 60
aaggacgacg acgacaagua a 81

<210> SEQ ID NO 92

-continued

<211> LENGTH: 84
<212> TYPE: RNA
<213> ORGANISM: Artificial Sequence
<220> FEATURE:
<223> OTHER INFORMATION: mRNA (mR10)

<400> SEQUENCE: 92
auguacaaga aguacaaaaa guacaaaccg ccgccgccgc cgccgccgcc gccgccggac 60
uacaaggacg acgacgacaa guaa 84

<210> SEQ ID NO 93
<211> LENGTH: 63
<212> TYPE: RNA
<213> ORGANISM: Artificial Sequence
<220> FEATURE:
<223> OTHER INFORMATION: mRNA (mR11)

<400> SEQUENCE: 93
auguacaaga aguacaaaaa guacaaaauu cauauugacu acaaggacga cgacgacaag 60
uaa 63

<210> SEQ ID NO 94
<211> LENGTH: 54
<212> TYPE: RNA
<213> ORGANISM: Artificial Sequence
<220> FEATURE:
<223> OTHER INFORMATION: mRNA (mR12)

<400> SEQUENCE: 94
augacuacua cuacucauaa gaagaaggac uacaaggacg acgacgacaa guaa 54

<210> SEQ ID NO 95
<211> LENGTH: 84
<212> TYPE: RNA
<213> ORGANISM: Artificial Sequence
<220> FEATURE:
<223> OTHER INFORMATION: mRNA (mR13)

<400> SEQUENCE: 95
auguacaaga aguacaaaaa guacaaaccg uacuauccgu auuacccgua cuauccggac 60
uacaaggacg acgacgacaa guaa 84

<210> SEQ ID NO 96
<211> LENGTH: 20
<212> TYPE: PRT
<213> ORGANISM: Artificial Sequence
<220> FEATURE:
<223> OTHER INFORMATION: reprogrammed peptide rP1
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: beta-cyclic amino acid

<400> SEQUENCE: 96

```
Met Tyr Lys Lys Tyr Lys Lys Tyr Lys Xaa Gly Gly Asp Tyr Lys Asp
1               5                   10                  15

Asp Asp Asp Lys
            20
```

<210> SEQ ID NO 97
<211> LENGTH: 20

```
<212> TYPE: PRT
<213> ORGANISM: Artificial Sequence
<220> FEATURE:
<223> OTHER INFORMATION: reprogrammed peptide rP2
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(11)
<223> OTHER INFORMATION: beta-cyclic amino acid

<400> SEQUENCE: 97

Met Tyr Lys Lys Tyr Lys Lys Tyr Lys Xaa Xaa Gly Asp Tyr Lys Asp
1               5                   10                  15

Asp Asp Asp Lys
            20


<210> SEQ ID NO 98
<211> LENGTH: 20
<212> TYPE: PRT
<213> ORGANISM: Artificial Sequence
<220> FEATURE:
<223> OTHER INFORMATION: reprogrammed peptide rP3
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(12)
<223> OTHER INFORMATION: beta-cyclic amino acid

<400> SEQUENCE: 98

Met Tyr Lys Lys Tyr Lys Lys Tyr Lys Xaa Xaa Xaa Asp Tyr Lys Asp
1               5                   10                  15

Asp Asp Asp Lys
            20


<210> SEQ ID NO 99
<211> LENGTH: 21
<212> TYPE: PRT
<213> ORGANISM: Artificial Sequence
<220> FEATURE:
<223> OTHER INFORMATION: reprogrammed peptide rP4
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(13)
<223> OTHER INFORMATION: beta-cyclic amino acid

<400> SEQUENCE: 99

Met Tyr Lys Lys Tyr Lys Lys Tyr Lys Xaa Xaa Xaa Xaa Asp Tyr Lys
1               5                   10                  15

Asp Asp Asp Asp Lys
            20


<210> SEQ ID NO 100
<211> LENGTH: 22
<212> TYPE: PRT
<213> ORGANISM: Artificial Sequence
<220> FEATURE:
<223> OTHER INFORMATION: reprogrammed peptide rP5
<220> FEATURE:
<221> NAME/KEY: MISC_FEATURE
<222> LOCATION: (1)..(1)
```

-continued

<223> OTHER INFORMATION: N-Formylmethionine
<220> FEATURE:
<221> NAME/KEY: MISC_FEATURE
<222> LOCATION: (10)..(14)
<223> OTHER INFORMATION: beta-cyclic amino acid

<400> SEQUENCE: 100

Met Tyr Lys Lys Tyr Lys Lys Tyr Lys Xaa Xaa Xaa Xaa Xaa Asp Tyr
1 5 10 15

Lys Asp Asp Asp Asp Lys
20

<210> SEQ ID NO 101
<211> LENGTH: 23
<212> TYPE: PRT
<213> ORGANISM: Artificial Sequence
<220> FEATURE:
<223> OTHER INFORMATION: reprogrammed peptide rP6
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(15)
<223> OTHER INFORMATION: beta-cyclic amino acid

<400> SEQUENCE: 101

Met Tyr Lys Lys Tyr Lys Lys Tyr Lys Xaa Xaa Xaa Xaa Xaa Xaa Asp
1 5 10 15

Tyr Lys Asp Asp Asp Asp Lys
20

<210> SEQ ID NO 102
<211> LENGTH: 24
<212> TYPE: PRT
<213> ORGANISM: Artificial Sequence
<220> FEATURE:
<223> OTHER INFORMATION: reprogrammed peptide rP7
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(16)
<223> OTHER INFORMATION: beta-cyclic amino acid

<400> SEQUENCE: 102

Met Tyr Lys Lys Tyr Lys Lys Tyr Lys Xaa Xaa Xaa Xaa Xaa Xaa Xaa
1 5 10 15

Asp Tyr Lys Asp Asp Asp Asp Lys
20

<210> SEQ ID NO 103
<211> LENGTH: 25
<212> TYPE: PRT
<213> ORGANISM: Artificial Sequence
<220> FEATURE:
<223> OTHER INFORMATION: reprogrammed peptide rP8
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(17)
<223> OTHER INFORMATION: beta-cyclic amino acid

<400> SEQUENCE: 103

```
Met Tyr Lys Lys Tyr Lys Lys Tyr Lys Xaa Xaa Xaa Xaa Xaa Xaa Xaa
1               5                   10                  15

Xaa Asp Tyr Lys Asp Asp Asp Asp Lys
            20                  25
```

<210> SEQ ID NO 104
<211> LENGTH: 26
<212> TYPE: PRT
<213> ORGANISM: Artificial Sequence
<220> FEATURE:
<223> OTHER INFORMATION: reprogrammed peptide rP9
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(18)
<223> OTHER INFORMATION: beta-cyclic amino acid

<400> SEQUENCE: 104

```
Met Tyr Lys Lys Tyr Lys Lys Tyr Lys Xaa Xaa Xaa Xaa Xaa Xaa Xaa
1               5                   10                  15

Xaa Xaa Asp Tyr Lys Asp Asp Asp Asp Lys
            20                  25
```

<210> SEQ ID NO 105
<211> LENGTH: 27
<212> TYPE: PRT
<213> ORGANISM: Artificial Sequence
<220> FEATURE:
<223> OTHER INFORMATION: reprogrammed peptide rP10
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(19)
<223> OTHER INFORMATION: beta-cyclic amino acid

<400> SEQUENCE: 105

```
Met Tyr Lys Lys Tyr Lys Lys Tyr Lys Xaa Xaa Xaa Xaa Xaa Xaa Xaa
1               5                   10                  15

Xaa Xaa Xaa Asp Tyr Lys Asp Asp Asp Asp Lys
            20                  25
```

<210> SEQ ID NO 106
<211> LENGTH: 20
<212> TYPE: PRT
<213> ORGANISM: Artificial Sequence
<220> FEATURE:
<223> OTHER INFORMATION: reprogrammed peptide rP11
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: (1S,2S)-2-ACPC
<220> FEATURE:
<221> NAME/KEY: MISC_FEATURE
<222> LOCATION: (11)..(11)
<223> OTHER INFORMATION: (1S,2S)-2-ACHC
<220> FEATURE:
<221> NAME/KEY: MISC_FEATURE
<222> LOCATION: (12)..(12)

<223> OTHER INFORMATION: (1S,2S)-2-ACPC

<400> SEQUENCE: 106

```
Met Tyr Lys Lys Tyr Lys Lys Tyr Lys Xaa Xaa Xaa Asp Tyr Lys Asp
1               5                   10                  15

Asp Asp Asp Lys
            20
```

<210> SEQ ID NO 107
<211> LENGTH: 17
<212> TYPE: PRT
<213> ORGANISM: Artificial Sequence
<220> FEATURE:
<223> OTHER INFORMATION: reprogrammed peptide rP12
<220> FEATURE:
<221> NAME/KEY: MISC_FEATURE
<222> LOCATION: (1)..(1)
<223> OTHER INFORMATION: N-Chloroacetyl phnylalanine
<220> FEATURE:
<221> NAME/KEY: MISC_FEATURE
<222> LOCATION: (2)..(5)
<223> OTHER INFORMATION: (1S,2S)-2-ACPC

<400> SEQUENCE: 107

```
Phe Xaa Xaa Xaa Xaa Cys Lys Lys Lys Asp Tyr Lys Asp Asp Asp Asp
1               5                   10                  15

Lys
```

<210> SEQ ID NO 108
<211> LENGTH: 27
<212> TYPE: PRT
<213> ORGANISM: Artificial Sequence
<220> FEATURE:
<223> OTHER INFORMATION: reprogrammed peptide rP13
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (10)..(10)
<223> OTHER INFORMATION: (1S,2S)-2-ACPC
<220> FEATURE:
<221> NAME/KEY: MISC_FEATURE
<222> LOCATION: (13)..(13)
<223> OTHER INFORMATION: (1S,2S)-2-ACPC
<220> FEATURE:
<221> NAME/KEY: MISC_FEATURE
<222> LOCATION: (16)..(16)
<223> OTHER INFORMATION: (1S,2S)-2-ACPC
<220> FEATURE:
<221> NAME/KEY: MISC_FEATURE
<222> LOCATION: (19)..(19)
<223> OTHER INFORMATION: (1S,2S)-2-ACPC

<400> SEQUENCE: 108

```
Met Tyr Lys Lys Tyr Lys Lys Tyr Lys Xaa Tyr Tyr Xaa Tyr Tyr Xaa
1               5                   10                  15

Tyr Tyr Xaa Asp Tyr Lys Asp Asp Asp Asp Lys
            20                  25
```

<210> SEQ ID NO 109
<211> LENGTH: 13
<212> TYPE: PRT
<213> ORGANISM: Artificial Sequence
<220> FEATURE:
<223> OTHER INFORMATION: Peptide obtained from FXIIa binder selection
(F1)
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 109

Tyr Asn Asp Arg Ser Thr Arg Xaa Arg Leu Val Ala Cys
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Peptide obtained from FXIIa binder selection
(F2)
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1S,2S)-2-ACHC

<400> SEQUENCE: 110

Tyr Pro Arg Leu Phe Asn Xaa Ser Tyr Leu Arg Arg Cys
1               5                   10

<210> SEQ ID NO 111
<211> LENGTH: 17
<212> TYPE: PRT
<213> ORGANISM: Artificial Sequence
<220> FEATURE:
<223> OTHER INFORMATION: Peptide obtained from FXIIa binder selection
(F3)
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1S,2S)-2-ACHC
<220> FEATURE:
<221> NAME/KEY: misc_feature
<222> LOCATION: (13)..(13)
<223> OTHER INFORMATION: Xaa can be any naturally occurring amino acid

<400> SEQUENCE: 111

Tyr Phe Ala Tyr Asp Arg Arg Xaa Leu Ser Asn Asn Xaa Arg Asn Tyr
1               5                   10                  15

Cys

<210> SEQ ID NO 112
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 112

Tyr Xaa Ala Phe Asp Arg Thr Phe Asn Xaa Arg Thr Xaa Thr Arg Tyr
1               5                   10                  15

Cys

<210> SEQ ID NO 113
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 113

Tyr Ser Asp Arg Ser Asp Tyr Asn Arg Arg Val Gly Cys
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 114

Tyr Arg Tyr Arg Asn Asn Asn Tyr Arg Arg Cys
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Peptide obtained from FXIIa binder selection
      (F4)
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACHC
<220> FEATURE:
<221> NAME/KEY: MISC_FEATURE
<222> LOCATION: (10)..(10)
<223> OTHER INFORMATION: (1S,2S)-2-ACHC

<400> SEQUENCE: 115

Tyr Arg Tyr Thr Xaa Asn Arg Leu Phe Xaa Asn Ala Cys
1               5                   10

<210> SEQ ID NO 116
<211> LENGTH: 16
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1S,2S)-2-ACHC
<220> FEATURE:
<221> NAME/KEY: MISC_FEATURE
<222> LOCATION: (12)..(12)
<223> OTHER INFORMATION: (1S,2S)-2-ACHC

<400> SEQUENCE: 116

Tyr Phe Leu Tyr Pro Xaa Pro Arg Tyr Asn Arg Xaa Phe Thr Asn Cys
1               5                   10                  15

<210> SEQ ID NO 117
<211> LENGTH: 14
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (3)..(3)
<223> OTHER INFORMATION: (1S,2S)-2-ACPC

<400> SEQUENCE: 117

Tyr Arg Xaa Phe Ser Asp Leu Asn Ser Leu Tyr Thr Ser Cys
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 118

Tyr Asn Asp Arg Ser Thr Arg Xaa Arg Pro Val Ala Cys
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 119

Tyr Ser Asp Arg Ser Thr Arg Xaa Arg Leu Val Ala Cys
1 5 10

<210> SEQ ID NO 120
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC

<400> SEQUENCE: 120

Tyr Pro Arg Pro Phe Asn Xaa Ser Tyr Leu Arg Arg Cys
1 5 10

<210> SEQ ID NO 121
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC

<400> SEQUENCE: 121

Tyr Pro Arg Leu Phe Ser Xaa Ser Tyr Leu Arg Arg Cys
1 5 10

<210> SEQ ID NO 122
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 122

Tyr Asn Asp Arg Ser Thr Arg His Arg Leu Val Ala Cys
1 5 10

<210> SEQ ID NO 123
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)

<223> OTHER INFORMATION: (1R,2R)-2-ACPC

<400> SEQUENCE: 123

```
Tyr Pro Arg Leu Phe Lys Xaa Ser Tyr Leu Arg Arg Cys
1               5                   10
```

<210> SEQ ID NO 124
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC

<400> SEQUENCE: 124

```
Tyr Pro Arg Leu Phe Asn Xaa Ser Tyr Pro Arg Arg Cys
1               5                   10
```

<210> SEQ ID NO 125
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC
<220> FEATURE:
<221> NAME/KEY: MISC_FEATURE
<222> LOCATION: (10)..(10)
<223> OTHER INFORMATION: (1S,2S)-2-ACHC
<220> FEATURE:
<221> NAME/KEY: MISC_FEATURE
<222> LOCATION: (14)..(14)
<223> OTHER INFORMATION: (1S,2S)-2-ACHC

<400> SEQUENCE: 125

```
Tyr Ser Asp Arg Ser Thr Phe Xaa Arg Xaa Val Leu Gly Xaa Asn Ser
1               5                   10                  15

Cys
```

<210> SEQ ID NO 126
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC

<400> SEQUENCE: 126

```
Tyr Pro Arg Leu Ser Asn Xaa Ser Tyr Leu Arg Arg Cys
1               5                   10
```

<210> SEQ ID NO 127
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 127

Tyr Asn Asp Arg Ser Thr Arg Arg Arg Leu Val Ala Cys
1 5 10

<210> SEQ ID NO 128
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 128

Tyr Asn Asp Arg Ser Thr Arg Xaa Arg Leu Ala Ala Cys
1 5 10

<210> SEQ ID NO 129
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 129

Tyr Phe Ala Tyr Asp Arg Arg Xaa Leu Ser Asn Asn Ile Arg Asn Tyr
1 5 10 15

Cys

<210> SEQ ID NO 130
<211> LENGTH: 12
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 130

Tyr Pro Arg Leu Leu Ile Ile Val Ile Phe Val Val
1 5 10

<210> SEQ ID NO 131
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (10)..(10)
<223> OTHER INFORMATION: (1R,2R)-2-ACPC
<220> FEATURE:
<221> NAME/KEY: MISC_FEATURE
<222> LOCATION: (13)..(13)
<223> OTHER INFORMATION: (1S,2S)-2-ACHC

<400> SEQUENCE: 131

```
Tyr Xaa Ala Val Asp Arg Ser Tyr Ser Xaa Ser Thr Xaa Arg Tyr Tyr
1               5                   10                  15

Cys
```

<210> SEQ ID NO 132
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (7)..(7)
<223> OTHER INFORMATION: (1R,2R)-2-ACPC

<400> SEQUENCE: 132

```
Ile Pro Arg Leu Phe Asn Xaa Ser Tyr Leu Arg Arg Cys
1               5                   10
```

<210> SEQ ID NO 133
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACHC
<220> FEATURE:
<221> NAME/KEY: MISC_FEATURE
<222> LOCATION: (10)..(10)
<223> OTHER INFORMATION: (1S,2S)-2-ACHC

<400> SEQUENCE: 133

```
Tyr Val Asp Thr Xaa Leu Arg Thr Leu Xaa Asn Val Cys
1               5                   10
```

<210> SEQ ID NO 134
<211> LENGTH: 17
<212> TYPE: PRT
<213> ORGANISM: Artificial Sequence
<220> FEATURE:

<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1S,2S)-2-ACPC
<220> FEATURE:
<221> NAME/KEY: MISC_FEATURE
<222> LOCATION: (10)..(10)
<223> OTHER INFORMATION: (1R,2R)-2-ACPC
<220> FEATURE:
<221> NAME/KEY: MISC_FEATURE
<222> LOCATION: (13)..(13)
<223> OTHER INFORMATION: (1S,2S)-2-ACPC

<400> SEQUENCE: 134

Tyr Ser Asn Val Pro Xaa Arg Tyr Ser Xaa Asp Ser Xaa Arg Tyr Ser
1 5 10 15

Cys

<210> SEQ ID NO 135
<211> LENGTH: 12
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (3)..(3)
<223> OTHER INFORMATION: (1S,2S)-2-ACPC

<400> SEQUENCE: 135

Tyr Arg Xaa Pro Ala Asp Leu Asn Arg Leu Phe Gln
1 5 10

<210> SEQ ID NO 136
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 136

Tyr Asn Asp Arg Ser Thr Arg Xaa Arg Leu Val Thr Cys
1 5 10

<210> SEQ ID NO 137
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:

<221> NAME/KEY: MISC_FEATURE
<222> LOCATION: (7)..(7)
<223> OTHER INFORMATION: (1R,2R)-2-ACPC

<400> SEQUENCE: 137

Tyr Pro Arg Leu Leu Asn Xaa Ser Tyr Leu Arg Arg Cys
1 5 10

<210> SEQ ID NO 138
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (13)..(13)
<223> OTHER INFORMATION: (1S,2S)-2-ACHC

<400> SEQUENCE: 138

Tyr Xaa Ala Phe Asp Arg Thr Phe Asn Arg Arg Thr Xaa Thr Arg Tyr
1 5 10 15

Cys

<210> SEQ ID NO 139
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC
<220> FEATURE:
<221> NAME/KEY: MISC_FEATURE
<222> LOCATION: (12)..(12)
<223> OTHER INFORMATION: (1R,2R)-2-ACPC

<400> SEQUENCE: 139

Tyr Pro Arg Leu Phe Asn Xaa Ser Tyr Leu Arg Xaa Cys
1 5 10

<210> SEQ ID NO 140
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC
<220> FEATURE:
<221> NAME/KEY: MISC_FEATURE
<222> LOCATION: (11)..(11)

<223> OTHER INFORMATION: (1S,2S)-2-ACPC

<400> SEQUENCE: 140

Tyr Pro Arg Leu Phe Asn Xaa Ser Tyr Leu Xaa Arg Cys
1 5 10

<210> SEQ ID NO 141
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC

<400> SEQUENCE: 141

Tyr Pro Arg Leu Phe Asn Xaa Gly Tyr Leu Arg Arg Cys
1 5 10

<210> SEQ ID NO 142
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 142

Tyr Asn Gly Arg Ser Thr Arg Xaa Arg Leu Val Ala Cys
1 5 10

<210> SEQ ID NO 143
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1S,2S)-2-ACHC
<220> FEATURE:
<221> NAME/KEY: MISC_FEATURE
<222> LOCATION: (13)..(13)
<223> OTHER INFORMATION: (1S,2S)-2-ACHC

<400> SEQUENCE: 143

Tyr Phe Ala Tyr Asp Arg Arg Xaa Leu Ser Ser Asn Xaa Arg Asn Tyr
1 5 10 15

Cys

<210> SEQ ID NO 144
<211> LENGTH: 13

<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACHC
<220> FEATURE:
<221> NAME/KEY: MISC_FEATURE
<222> LOCATION: (10)..(10)
<223> OTHER INFORMATION: (1S,2S)-2-ACHC

<400> SEQUENCE: 144

Tyr Arg Tyr Thr Xaa Asn Arg Leu Leu Xaa Asn Ala Cys
1 5 10

<210> SEQ ID NO 145
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1S,2S)-2-ACHC
<220> FEATURE:
<221> NAME/KEY: MISC_FEATURE
<222> LOCATION: (13)..(13)
<223> OTHER INFORMATION: (1S,2S)-2-ACHC

<400> SEQUENCE: 145

Tyr Phe Ala Tyr Asp Arg Arg Xaa Leu Ser Asn Ser Xaa Arg Asn Tyr
1 5 10 15

Cys

<210> SEQ ID NO 146
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC
<220> FEATURE:
<221> NAME/KEY: MISC_FEATURE
<222> LOCATION: (12)..(12)
<223> OTHER INFORMATION: (1S,2S)-2-ACPC

<400> SEQUENCE: 146

Tyr Pro Arg Leu Phe Asn Xaa Ser Tyr Leu Arg Xaa Cys
1 5 10

<210> SEQ ID NO 147
<211> LENGTH: 13
<212> TYPE: PRT
<213> ORGANISM: Artificial Sequence -continued
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1S,2S)-2-ACPC
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 147

Tyr Asn Asp Arg Ser Thr Xaa Xaa Arg Leu Val Ala Cys
1 5 10

<210> SEQ ID NO 148
<211> LENGTH: 11
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 148

Tyr Arg Tyr Arg Asn Asp Asn Tyr Arg Arg Cys
1 5 10

<210> SEQ ID NO 149
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC
<220> FEATURE:
<221> NAME/KEY: MISC_FEATURE
<222> LOCATION: (9)..(9)
<223> OTHER INFORMATION: (1R,2R)-2-ACPC

<400> SEQUENCE: 149

Tyr Pro Arg Leu Phe Asn Xaa Ser Xaa Leu Arg Arg Cys
1 5 10

<210> SEQ ID NO 150
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1R,2R)-2-ACPC
<220> FEATURE:
<221> NAME/KEY: MISC_FEATURE

<222> LOCATION: (11)..(11)
<223> OTHER INFORMATION: (1R,2R)-2-ACPC

<400> SEQUENCE: 150

Tyr Pro Arg Leu Phe Asn Xaa Ser Tyr Leu Xaa Arg Cys
1 5 10

<210> SEQ ID NO 151
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC
<220> FEATURE:
<221> NAME/KEY: MISC_FEATURE
<222> LOCATION: (9)..(9)
<223> OTHER INFORMATION: (1S,2S)-2-ACPC

<400> SEQUENCE: 151

Tyr Asn Asp Arg Ser Thr Arg Xaa Xaa Leu Val Ala Cys
1 5 10

<210> SEQ ID NO 152
<211> LENGTH: 12
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACHC

<400> SEQUENCE: 152

Tyr Thr Asn Thr Xaa Leu Arg Leu Leu Ser Asn Cys
1 5 10

<210> SEQ ID NO 153
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC
<220> FEATURE:
<221> NAME/KEY: MISC_FEATURE
<222> LOCATION: (9)..(9)
<223> OTHER INFORMATION: (1R,2R)-2-ACPC

<400> SEQUENCE: 153

Tyr Asn Asp Arg Ser Thr Arg Xaa Xaa Leu Val Ala Cys
1 5 10

<210> SEQ ID NO 154
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 154

Tyr Asn Asp Arg Ser Ala Arg Xaa Arg Leu Val Ala Cys
1 5 10

<210> SEQ ID NO 155
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (4)..(4)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 155

Tyr Asn Asp Xaa Ser Thr Arg Xaa Arg Leu Val Ala Cys
1 5 10

<210> SEQ ID NO 156
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 156

Tyr Pro Arg Leu Phe Asn Arg Ser Tyr Leu Arg Arg Cys
1 5 10

<210> SEQ ID NO 157
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:

<221> NAME/KEY: MISC_FEATURE
<222> LOCATION: (8)..(8)
<223> OTHER INFORMATION: (1S,2S)-2-ACPC
<220> FEATURE:
<221> NAME/KEY: MISC_FEATURE
<222> LOCATION: (13)..(13)
<223> OTHER INFORMATION: (1S,2S)-2-ACHC
<220> FEATURE:
<221> NAME/KEY: MISC_FEATURE
<222> LOCATION: (14)..(14)
<223> OTHER INFORMATION: (1S,2S)-2-ACPC

<400> SEQUENCE: 157

Tyr Xaa Ala Thr Asn Arg Val Xaa Val Asn Arg Thr Xaa Xaa Asn Tyr
1 5 10 15

Cys

<210> SEQ ID NO 158
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (3)..(3)
<223> OTHER INFORMATION: (1R,2R)-2-ACPC
<220> FEATURE:
<221> NAME/KEY: MISC_FEATURE
<222> LOCATION: (7)..(7)
<223> OTHER INFORMATION: (1R,2R)-2-ACPC

<400> SEQUENCE: 158

Tyr Pro Xaa Leu Phe Asn Xaa Ser Tyr Leu Arg Arg Cys
1 5 10

<210> SEQ ID NO 159
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC
<220> FEATURE:
<221> NAME/KEY: MISC_FEATURE
<222> LOCATION: (11)..(11)
<223> OTHER INFORMATION: (1S,2S)-2-ACHC

<400> SEQUENCE: 159

Tyr Asn Asp Arg Ser Thr Arg Xaa Arg Leu Xaa Ala Cys
1 5 10

<210> SEQ ID NO 160
<211> LENGTH: 8
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)

<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACPC

<400> SEQUENCE: 160

Tyr Gly Tyr Leu Xaa Phe Thr Cys
1 5

<210> SEQ ID NO 161
<211> LENGTH: 13
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 161

Ile Asn Asp Arg Ser Thr Arg Xaa Arg Leu Val Ala Cys
1 5 10

<210> SEQ ID NO 162
<211> LENGTH: 17
<212> TYPE: PRT
<213> ORGANISM: Artificial Sequence
<220> FEATURE:
<223> OTHER INFORMATION: Peptide obtained from FXIIa binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (13)..(13)
<223> OTHER INFORMATION: (1S,2S)-2-ACHC

<400> SEQUENCE: 162

Tyr Phe Ala Tyr Asp Arg Arg Ile Leu Ser Asn Asn Xaa Arg Asn Tyr
1 5 10 15

Cys

<210> SEQ ID NO 163
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 163

Tyr Phe Gly Val Arg Xaa Phe Tyr Asn Arg Thr Cys
1 5 10

<210> SEQ ID NO 164
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 164

Tyr Xaa Gly Leu Ser Xaa Tyr Val Asn Arg Ser Cys
1 5 10

<210> SEQ ID NO 165
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 165

Tyr Val Gly Leu Asn Xaa Ser Leu Asn Arg Thr Cys
1 5 10

<210> SEQ ID NO 166
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 166

Tyr Phe Gly Leu Ser Xaa Phe Tyr Arg Arg Ser Cys
1 5 10

<210> SEQ ID NO 167
<211> LENGTH: 14
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 167

Tyr Phe Ser Leu Arg Xaa Ser Phe Asn Arg Ser Arg Gly Cys
1 5 10

<210> SEQ ID NO 168
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

<400> SEQUENCE: 168

Tyr Xaa Gly Leu Ser His Tyr Val Asn Arg Ser Cys
1 5 10

<210> SEQ ID NO 169
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 169

Tyr Tyr Gly Val Asn Xaa Ser Tyr Asn Arg Ser Cys
1 5 10

<210> SEQ ID NO 170
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 170

Tyr Tyr Ser Val Ser Xaa Arg Phe Asn Arg Thr Cys
1 5 10

<210> SEQ ID NO 171
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)

<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 171

```
Tyr Phe Asp Leu Arg Xaa Arg Leu Ala Asn Cys
1               5                   10
```

<210> SEQ ID NO 172
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 172

```
Tyr Phe Ala Leu Asn Xaa Arg Xaa Asn Arg Arg Cys
1               5                   10
```

<210> SEQ ID NO 173
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 173

```
Tyr Tyr Asp Leu Arg Xaa Arg Leu Tyr Arg Asn Cys
1               5                   10
```

<210> SEQ ID NO 174
<211> LENGTH: 15
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

<400> SEQUENCE: 174

```
Tyr Xaa Ala Leu Ser Arg Ser Arg Arg Thr Thr Arg Asp Asn Cys
1               5                   10                  15
```

<210> SEQ ID NO 175
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (7)..(7)
<223> OTHER INFORMATION: (1S,2S)-2-ACHC

<400> SEQUENCE: 175

```
Tyr Phe Gly Leu Ser Xaa Xaa Leu Ser Arg Cys
1               5                   10
```

<210> SEQ ID NO 176
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 176

```
Tyr Tyr Asp Leu Arg Xaa Arg Leu Ser Asn Cys
1               5                   10
```

<210> SEQ ID NO 177
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 177

```
Tyr Tyr Asp Leu Arg Xaa Arg Leu Tyr Ser Cys
1               5                   10
```

<210> SEQ ID NO 178
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE

<222> LOCATION: (6)..(6)
<223> OTHER INFORMATION: (1R,2R)-2-ACPC

<400> SEQUENCE: 178

Tyr Tyr Asn Val Arg Xaa Phe Val Asn Arg Thr Cys
1 5 10

<210> SEQ ID NO 179
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 179

Tyr Phe Asp Val Arg Xaa Arg Xaa Asn Ser Cys
1 5 10

<210> SEQ ID NO 180
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 180

Tyr Phe Gly Leu Ser Xaa Phe Val Ser Pro Cys
1 5 10

<210> SEQ ID NO 181
<211> LENGTH: 15
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

<400> SEQUENCE: 181

Tyr Xaa Gly Leu Asn Arg Ser Leu Pro Pro Arg Leu Tyr Asn Cys
1 5 10 15

<210> SEQ ID NO 182
<211> LENGTH: 11
<212> TYPE: PRT

<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 182

Tyr Tyr Asp Leu Arg Xaa Ala Xaa Asn Asn Cys
1 5 10

<210> SEQ ID NO 183
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 183

Tyr Xaa Gly Leu Ser Xaa Tyr Val Asn Arg Thr Cys
1 5 10

<210> SEQ ID NO 184
<211> LENGTH: 16
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

<400> SEQUENCE: 184

Tyr Xaa Ser Leu Ser Arg Asn Arg Val Pro Arg Leu Val Leu Thr Cys
1 5 10 15

<210> SEQ ID NO 185
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:

-continued

<221> NAME/KEY: MISC_FEATURE
<222> LOCATION: (6)..(6)
<223> OTHER INFORMATION: (1R,2R)-2-ACPC

<400> SEQUENCE: 185

Tyr Tyr Asp Val Arg Xaa Arg Val Ser Asn Cys
1 5 10

<210> SEQ ID NO 186
<211> LENGTH: 14
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 186

Tyr Tyr Ser Val Asn Xaa Tyr Xaa Asn Arg Ser Asn Asn Cys
1 5 10

<210> SEQ ID NO 187
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 187

Tyr Ile Gly Leu Ser Xaa Tyr Val Asn Arg Ser Cys
1 5 10

<210> SEQ ID NO 188
<211> LENGTH: 16
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1S,2S)-2-ACHC
<220> FEATURE:
<221> NAME/KEY: MISC_FEATURE
<222> LOCATION: (13)..(14)
<223> OTHER INFORMATION: (1R,2R)-2-ACPC

<400> SEQUENCE: 188

Tyr Arg Ser Ser Asn Xaa Arg Pro Arg Leu Arg Tyr Xaa Xaa Leu Cys
1 5 10 15

<210> SEQ ID NO 189
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 189

Tyr Tyr Gly Leu Ser Xaa Tyr Val Ser Asn Cys
1 5 10

<210> SEQ ID NO 190
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 190

Tyr Phe Gly Val Arg Xaa Leu Tyr Asn Arg Thr Cys
1 5 10

<210> SEQ ID NO 191
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 191

Tyr Phe Ser Val Tyr Xaa Phe Phe Asn Arg Leu Cys
1 5 10

<210> SEQ ID NO 192
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

```
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 192

Tyr Xaa Gly Leu Gly Xaa Tyr Val Asn Arg Ser Cys
1               5                   10


<210> SEQ ID NO 193
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 193

Tyr Tyr Asp Val Arg Xaa Arg Xaa Val Asn Cys
1               5                   10


<210> SEQ ID NO 194
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 194

Tyr Phe Gly Leu Thr Xaa Tyr Leu Asn Arg Asn Cys
1               5                   10


<210> SEQ ID NO 195
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 195

Tyr Leu Gly Val Arg Xaa Phe Tyr Asn Arg Thr Cys
1               5                   10


<210> SEQ ID NO 196
```

-continued

<211> LENGTH: 16
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1S,2S)-2-ACPC
<220> FEATURE:
<221> NAME/KEY: MISC_FEATURE
<222> LOCATION: (14)..(14)
<223> OTHER INFORMATION: (1R,2R)-2-ACPC

<400> SEQUENCE: 196

Tyr Pro Arg Tyr Asn Leu Xaa Gly Ala Ser Pro Arg Phe Xaa Asn Cys
1               5                   10                  15

<210> SEQ ID NO 197
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (5)..(5)
<223> OTHER INFORMATION: (1R,2R)-2-ACPC

<400> SEQUENCE: 197

Tyr Xaa Gly Arg Xaa Tyr Phe Asn Arg Ser Cys
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 198

Tyr Tyr Asp Leu Arg Xaa Tyr Xaa Arg Asn Cys
1               5                   10

<210> SEQ ID NO 199
<211> LENGTH: 12
<212> TYPE: PRT
<213> ORGANISM: Artificial Sequence
<220> FEATURE:

<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 199

Tyr Phe Gly Val Arg His Phe Tyr Asn Arg Thr Cys
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 200

Tyr Phe Gly Ala Arg Xaa Phe Tyr Asn Arg Thr Cys
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 201

Tyr Asn Ser Arg Val Arg Leu Tyr Leu Asn Pro Cys
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACPC
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 202

Tyr Tyr Asp Leu Xaa Xaa Arg Xaa Ser Asn Cys
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 203

Tyr Phe Gly Val Arg Xaa Phe Tyr Asn Arg Ala Cys
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(6)
<223> OTHER INFORMATION: (1R,2R)-2-ACPC

<400> SEQUENCE: 204

Tyr Phe Gly Arg Xaa Xaa Phe Asn Arg Ser Cys
1               5                   10

<210> SEQ ID NO 205
<211> LENGTH: 15
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (11)..(11)
<223> OTHER INFORMATION: (1S,2S)-2-ACPC

<400> SEQUENCE: 205

Tyr Xaa Gly Leu Ser Arg Ser Asn Pro Asn Xaa Arg Asn Pro Cys
1               5                   10                  15

<210> SEQ ID NO 206
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE

<222> LOCATION: (6)..(6)
<223> OTHER INFORMATION: (1R,2R)-2-ACPC

<400> SEQUENCE: 206

```
Tyr Phe Ala Leu Arg Xaa Phe Phe Ala Asn Cys
1               5                   10
```

<210> SEQ ID NO 207
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 207

```
Tyr Tyr Gly Leu Ser Xaa Tyr Phe Arg Asp Cys
1               5                   10
```

<210> SEQ ID NO 208
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 208

```
Tyr Tyr Asn Leu Arg Xaa Phe Xaa Ser Asn Cys
1               5                   10
```

<210> SEQ ID NO 209
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: misc_feature
<222> LOCATION: (8)..(8)
<223> OTHER INFORMATION: Xaa can be any naturally occurring amino acid

<400> SEQUENCE: 209

Tyr Xaa Gly Leu Ser Xaa Tyr Xaa Asn Arg Ser Cys
1 5 10

<210> SEQ ID NO 210
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 210

Tyr Phe Gly Val Arg Xaa Phe Tyr Asp Arg Thr Cys
1 5 10

<210> SEQ ID NO 211
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 211

Tyr Tyr Ser Val Arg Xaa Ala Xaa Asn Arg Val Cys
1 5 10

<210> SEQ ID NO 212
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 212

Tyr Phe Gly Val Arg Xaa Phe Tyr Asn Arg Ser Cys
1 5 10

<210> SEQ ID NO 213
<211> LENGTH: 11
<212> TYPE: PRT
<213> ORGANISM: Artificial Sequence
<220> FEATURE:

<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (7)..(7)
<223> OTHER INFORMATION: (1S,2S)-2-ACHC

<400> SEQUENCE: 213

Tyr Tyr Gly Leu Ser Xaa Xaa Val Ser Leu Cys
1 5 10

<210> SEQ ID NO 214
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 214

Tyr Xaa Gly Leu Ser Xaa Tyr Val Asn Arg Asn Cys
1 5 10

<210> SEQ ID NO 215
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 215

Tyr Phe Gly Leu Ser Xaa Phe Tyr Arg Arg Thr Cys
1 5 10

<210> SEQ ID NO 216
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)

<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 216

Tyr Xaa Gly Leu Ser Xaa Tyr Val Asp Arg Ser Cys
1 5 10

<210> SEQ ID NO 217
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 217

Tyr Tyr Asp Val Arg Xaa Arg Xaa Tyr Asn Cys
1 5 10

<210> SEQ ID NO 218
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACPC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 218

Tyr Phe Gly Val Xaa Xaa Phe Tyr Asn Arg Thr Cys
1 5 10

<210> SEQ ID NO 219
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 219

Tyr Val Gly Leu Ser Xaa Tyr Val Asn Arg Ser Cys
1 5 10

<210> SEQ ID NO 220
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 220

Tyr Tyr Asp Leu Arg Xaa Arg Xaa Val Arg Asn Cys
1 5 10

<210> SEQ ID NO 221
<211> LENGTH: 16
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

<400> SEQUENCE: 221

Tyr Xaa Ala Leu Ser Arg Arg Arg Arg Ser Tyr Arg Asn Gly Leu Cys
1 5 10 15

<210> SEQ ID NO 222
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 222

Tyr Ser Gly Val Arg Xaa Phe Tyr Asn Arg Thr Cys
1 5 10

<210> SEQ ID NO 223
<211> LENGTH: 11
<212> TYPE: PRT
<213> ORGANISM: Artificial Sequence
<220> FEATURE:

<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 223

Tyr Tyr Gly Leu Ser Xaa Phe Leu Ser Asn Cys
1 5 10

<210> SEQ ID NO 224
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 224

Tyr Xaa Asp Leu Arg Xaa Arg Leu Tyr Asp Cys
1 5 10

<210> SEQ ID NO 225
<211> LENGTH: 15
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: misc_feature
<222> LOCATION: (4)..(4)
<223> OTHER INFORMATION: Xaa can be any naturally occurring amino acid

<400> SEQUENCE: 225

Tyr Xaa Gly Xaa Tyr Arg Arg Tyr Leu Pro Arg Arg Ser Pro Cys
1 5 10 15

<210> SEQ ID NO 226
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)

<223> OTHER INFORMATION: (1R,2R)-2-ACPC

<400> SEQUENCE: 226

Tyr Thr Gly Leu Ser Xaa Tyr Val Asn Arg Ser Cys
1 5 10

<210> SEQ ID NO 227
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 227

Tyr Phe Gly Leu Ser His Phe Tyr Arg Arg Ser Cys
1 5 10

<210> SEQ ID NO 228
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 228

Tyr Phe Gly Val Arg Xaa Phe Tyr Ser Arg Thr Cys
1 5 10

<210> SEQ ID NO 229
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 229

Tyr Tyr Asp Val Arg Xaa Arg Leu Asn Pro Asn Cys
1 5 10

<210> SEQ ID NO 230
<211> LENGTH: 16
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1R,2R)-2-ACPC
<220> FEATURE:
<221> NAME/KEY: MISC_FEATURE
<222> LOCATION: (4)..(4)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1S,2S)-2-ACPC

<400> SEQUENCE: 230

Tyr Xaa Gly Xaa Ser Xaa Phe Ser Arg Asn Ser Val Asn Arg Ser Cys
1 5 10 15

<210> SEQ ID NO 231
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACPC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 231

Tyr Phe Asn Leu Xaa Xaa Phe Leu Ser Pro Cys
1 5 10

<210> SEQ ID NO 232
<211> LENGTH: 13
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 232

Tyr Tyr Asn Leu Arg Xaa Tyr Xaa Asn Arg Ser Asn Cys
1 5 10

<210> SEQ ID NO 233
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 233

Tyr Phe Gly Val Arg Xaa Phe Xaa Asn Arg Thr Cys
1 5 10

<210> SEQ ID NO 234
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (10)..(10)
<223> OTHER INFORMATION: (1R,2R)-2-ACPC

<400> SEQUENCE: 234

Tyr Phe Gly Val Arg Xaa Phe Tyr Asn Xaa Thr Cys
1 5 10

<210> SEQ ID NO 235
<211> LENGTH: 14
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 235

Tyr Phe Ser Leu Arg Xaa Ser Phe Asn Arg Ser Arg Ser Cys
1 5 10

<210> SEQ ID NO 236
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1R,2R)-2-ACPC
<220> FEATURE:
<221> NAME/KEY: MISC_FEATURE
<222> LOCATION: (10)..(10)
<223> OTHER INFORMATION: (1S,2S)-2-ACHC

<400> SEQUENCE: 236

Tyr Tyr Thr Arg Xaa Gly Arg Ser Arg Xaa Asn Cys
1 5 10

<210> SEQ ID NO 237
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(7)
<223> OTHER INFORMATION: (1R,2R)-2-ACPC

<400> SEQUENCE: 237

Tyr Xaa Gly Leu Ser Xaa Xaa Val Asn Arg Ser Cys
1 5 10

<210> SEQ ID NO 238
<211> LENGTH: 14
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: misc_feature
<222> LOCATION: (8)..(8)
<223> OTHER INFORMATION: Xaa can be any naturally occurring amino acid

<400> SEQUENCE: 238

Tyr Xaa Pro Val Asn Arg Tyr Xaa Arg Arg Phe Asn Arg Cys
1 5 10

<210> SEQ ID NO 239
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 239

Tyr Phe Gly Val Arg Xaa Ser Tyr Asn Arg Thr Cys
1 5 10

<210> SEQ ID NO 240

<211> LENGTH: 17
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (10)..(10)
<223> OTHER INFORMATION: (1S,2S)-2-ACPC
<220> FEATURE:
<221> NAME/KEY: MISC_FEATURE
<222> LOCATION: (11)..(11)
<223> OTHER INFORMATION: (1R,2R)-2-ACPC
<220> FEATURE:
<221> NAME/KEY: MISC_FEATURE
<222> LOCATION: (16)..(16)
<223> OTHER INFORMATION: (1R,2R)-2-ACPC

<400> SEQUENCE: 240

```
Tyr Tyr Asp Leu Arg Xaa Arg Phe Asn Xaa Xaa Asp Thr Ser Pro Xaa
1               5                   10                  15

Cys
```

<210> SEQ ID NO 241
<211> LENGTH: 17
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (8)..(8)
<223> OTHER INFORMATION: (1S,2S)-2-ACPC
<220> FEATURE:
<221> NAME/KEY: MISC_FEATURE
<222> LOCATION: (9)..(9)
<223> OTHER INFORMATION: (1S,2S)-2-ACHC
<220> FEATURE:
<221> NAME/KEY: MISC_FEATURE
<222> LOCATION: (12)..(12)
<223> OTHER INFORMATION: (1S,2S)-2-ACPC

<400> SEQUENCE: 241

```
Tyr Xaa Ser Val Arg Arg Tyr Xaa Xaa Leu Asn Xaa Asn Arg Ser Leu
1               5                   10                  15

Cys
```

<210> SEQ ID NO 242
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 242

Tyr Phe Asp Val Arg Xaa Phe Tyr Asn Arg Thr Cys
1 5 10

<210> SEQ ID NO 243
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 243

Tyr Phe Gly Leu Gly Xaa Phe Tyr Arg Arg Ser Cys
1 5 10

<210> SEQ ID NO 244
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 244

Tyr Tyr Asp Val Arg Xaa Phe Xaa Arg Thr Cys
1 5 10

<210> SEQ ID NO 245
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 245

Tyr Tyr Asp Val Arg Xaa Phe Leu Arg Thr Cys
1 5 10

<210> SEQ ID NO 246

<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 246

Tyr Xaa Ala Leu Asn Xaa Ala Xaa Asn Arg Ser Cys
1 5 10

<210> SEQ ID NO 247
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (7)..(7)
<223> OTHER INFORMATION: (1S,2S)-2-ACHC

<400> SEQUENCE: 247

Tyr Xaa Gly Leu Asn Xaa Xaa Leu Asn Arg Ala Cys
1 5 10

<210> SEQ ID NO 248
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 248

Tyr Xaa Gly Pro Ser Xaa Tyr Val Asn Arg Ser Cys
1 5 10

<210> SEQ ID NO 249
<211> LENGTH: 13
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (7)..(7)
<223> OTHER INFORMATION: (1R,2R)-2-ACPC

<400> SEQUENCE: 249

Tyr Xaa Ser Pro Arg Arg Xaa Thr Phe Asn Arg Thr Cys
1 5 10

<210> SEQ ID NO 250
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 250

Tyr Phe Gly Val Arg Xaa Phe Ile Ile Val Leu
1 5 10

<210> SEQ ID NO 251
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 251

Tyr Xaa Gly Leu Ser Xaa Tyr Ala Asn Arg Ser Cys
1 5 10

<210> SEQ ID NO 252

<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 252

Tyr Xaa Ser Leu Ser Xaa Tyr Val Asn Arg Ser Cys
1 5 10

<210> SEQ ID NO 253
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACPC

<400> SEQUENCE: 253

Tyr Phe Gly Val Arg Xaa Phe Xaa Asn Arg Thr Cys
1 5 10

<210> SEQ ID NO 254
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 254

Tyr Xaa Gly Leu Ser Xaa Tyr Val Ser Arg Ser Cys
1 5 10

<210> SEQ ID NO 255
<211> LENGTH: 12
<212> TYPE: PRT
<213> ORGANISM: Artificial Sequence
<220> FEATURE:

<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 255

Tyr Xaa Gly Val Arg Xaa Phe Tyr Asn Arg Thr Cys
1 5 10

<210> SEQ ID NO 256
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 256

Tyr Phe Gly Leu Ser Xaa Leu Tyr Arg Arg Ser Cys
1 5 10

<210> SEQ ID NO 257
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 257

Tyr Val Gly Leu Asn His Ser Leu Asn Arg Thr Cys
1 5 10

<210> SEQ ID NO 258
<211> LENGTH: 14
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 258

Tyr Xaa Ala Val Thr Xaa Phe Val Asn Arg Ser Asn Asp Cys
1 5 10

<210> SEQ ID NO 259
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 259

Tyr Xaa Gly Leu Asn Xaa Tyr Val Asn Arg Ser Cys
1 5 10

<210> SEQ ID NO 260
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

<400> SEQUENCE: 260

Tyr Xaa Gly Leu Ser Arg Tyr Val Asn Arg Ser Cys
1 5 10

<210> SEQ ID NO 261
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACPC
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 261

Tyr Xaa Asp Val Arg Xaa Arg Xaa Ser Asn Cys
1 5 10

<210> SEQ ID NO 262
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 262

Tyr Phe Gly Leu Ser Xaa Tyr Val Asn Arg Ser Cys
1 5 10

<210> SEQ ID NO 263
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 263

Tyr Phe Gly Val Arg Arg Phe Tyr Asn Arg Thr Cys
1 5 10

<210> SEQ ID NO 264
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC
<220> FEATURE:
<221> NAME/KEY: MISC_FEATURE
<222> LOCATION: (10)..(10)
<223> OTHER INFORMATION: (1S,2S)-2-ACPC

<400> SEQUENCE: 264

Tyr Tyr Gly Leu Asn Xaa Thr Xaa Asn Xaa Gly Cys
1 5 10

<210> SEQ ID NO 265
<211> LENGTH: 12
<212> TYPE: PRT
<213> ORGANISM: Artificial Sequence
<220> FEATURE:

-continued

<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 265

Tyr Tyr Gly Val Asn Xaa Ser Tyr Asn Arg Thr Cys
1 5 10

<210> SEQ ID NO 266
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 266

Tyr Xaa Asp Leu Ser Xaa Tyr Val Asn Arg Ser Cys
1 5 10

<210> SEQ ID NO 267
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 267

Tyr Xaa Gly Leu Ser Xaa Tyr Val Asn Arg Gly Cys
1 5 10

<210> SEQ ID NO 268
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)

<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC
<220> FEATURE:
<221> NAME/KEY: MISC_FEATURE
<222> LOCATION: (9)..(9)
<223> OTHER INFORMATION: (1S,2S)-2-ACPC

<400> SEQUENCE: 268

Tyr Phe Asp Leu Arg Xaa Tyr Xaa Xaa Asn Cys
1 5 10

<210> SEQ ID NO 269
<211> LENGTH: 13
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (4)..(4)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 269

Tyr Arg Ala Xaa Arg Xaa Ser Gly Arg Leu Asn Ser Cys
1 5 10

<210> SEQ ID NO 270
<211> LENGTH: 9
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (3)..(3)
<223> OTHER INFORMATION: (1S,2S)-2-ACHC
<220> FEATURE:
<221> NAME/KEY: MISC_FEATURE
<222> LOCATION: (6)..(7)
<223> OTHER INFORMATION: (1R,2R)-2-ACPC

<400> SEQUENCE: 270

Tyr Tyr Xaa Arg Tyr Xaa Xaa Leu Cys
1 5

<210> SEQ ID NO 271
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)

<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 271

Tyr Tyr Asp Leu Arg Xaa Arg Xaa Arg Thr Cys
1 5 10

<210> SEQ ID NO 272
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 272

Tyr Tyr Gly Leu Ser Xaa Phe Leu Ser Ser Cys
1 5 10

<210> SEQ ID NO 273
<211> LENGTH: 14
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 273

Tyr Phe Ser Leu Arg His Ser Phe Asn Arg Ser Arg Gly Cys
1 5 10

<210> SEQ ID NO 274
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 274

Tyr Ala Gly Leu Asn Xaa Ser Leu Asn Arg Thr Cys
1 5 10

<210> SEQ ID NO 275
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 275

Tyr Phe Gly Leu Ser Xaa Phe Tyr Arg Arg Asn Cys
1 5 10

<210> SEQ ID NO 276
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (10)..(10)
<223> OTHER INFORMATION: (1S,2S)-2-ACPC

<400> SEQUENCE: 276

Tyr Phe Gly Val Arg Xaa Phe Tyr Asn Xaa Thr Cys
1 5 10

<210> SEQ ID NO 277
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 277

Tyr Phe Ser Val Arg Xaa Phe Tyr Asn Arg Thr Cys
1 5 10

<210> SEQ ID NO 278
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 278

Tyr Tyr Gly Val Arg Xaa Phe Tyr Asn Arg Thr Cys
1 5 10

<210> SEQ ID NO 279
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 279

Ile Xaa Gly Leu Ser Xaa Tyr Val Asn Arg Ser Cys
1 5 10

<210> SEQ ID NO 280
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

<400> SEQUENCE: 280

Tyr Xaa Gly Leu Ser His Tyr Val Asn Arg Thr Cys
1 5 10

<210> SEQ ID NO 281
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 281

Tyr Phe Gly Leu Ser Xaa Ser Tyr Arg Arg Ser Cys
1 5 10

<210> SEQ ID NO 282
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (4)..(4)
<223> OTHER INFORMATION: (1S,2S)-2-ACHC
<220> FEATURE:

<221> NAME/KEY: MISC_FEATURE
<222> LOCATION: (6)..(6)
<223> OTHER INFORMATION: (1R,2R)-2-ACPC

<400> SEQUENCE: 282

Tyr Phe Ser Xaa Arg Xaa Val Phe Asn Arg Ser Cys
1 5 10

<210> SEQ ID NO 283
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (4)..(4)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 283

Tyr Tyr Asp Xaa Arg Xaa Arg Leu Asn Ala Cys
1 5 10

<210> SEQ ID NO 284
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 284

Tyr Tyr Ser Val Arg Xaa Ala Ile Asn Arg Val Cys
1 5 10

<210> SEQ ID NO 285
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC

<400> SEQUENCE: 285

Tyr Xaa Gly Leu Gly His Tyr Val Asn Arg Ser Cys
1 5 10

<210> SEQ ID NO 286
<211> LENGTH: 12

<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 286

Tyr Xaa Gly Leu Asn Xaa Ser Leu Asn Arg Thr Cys
1               5                   10

<210> SEQ ID NO 287
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (4)..(4)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 287

Tyr Phe Gly Xaa Arg Xaa Phe Tyr Asn Arg Thr Cys
1               5                   10

<210> SEQ ID NO 288
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(6)
<223> OTHER INFORMATION: (1R,2R)-2-ACPC

<400> SEQUENCE: 288

Tyr Phe Gly Val Xaa Xaa Phe Tyr Asn Arg Thr Cys
1               5                   10

<210> SEQ ID NO 289
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine -continued
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 289

Tyr Val Gly Leu Asn Xaa Ser Leu Asn Arg Ser Cys
1 5 10

<210> SEQ ID NO 290
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 290

Ile Phe Gly Val Arg Xaa Phe Tyr Asn Arg Thr Cys
1 5 10

<210> SEQ ID NO 291
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 291

Tyr Xaa Gly Leu Arg Xaa Tyr Val Asn Arg Ser Cys
1 5 10

<210> SEQ ID NO 292
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 292

Tyr Xaa Ser Leu Thr Xaa Phe Val Asn Arg Arg Cys
1 5 10

<210> SEQ ID NO 293
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 293

Tyr Phe Gly Leu Asn Xaa Phe Tyr Arg Arg Ser Cys
1 5 10

<210> SEQ ID NO 294
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 294

Tyr Phe Gly Val Arg Xaa Phe Tyr Asn Arg Asn Cys
1 5 10

<210> SEQ ID NO 295
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 295

Tyr Ile Gly Leu Ser His Tyr Val Asn Arg Ser Cys
1 5 10

<210> SEQ ID NO 296
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)

<223> OTHER INFORMATION: (1R,2R)-2-ACPC

<400> SEQUENCE: 296

Tyr Val Gly Leu Asn Xaa Ser Pro Asn Arg Thr Cys
1 5 10

<210> SEQ ID NO 297
<211> LENGTH: 11
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 297

Tyr Tyr Ala Leu Asn Xaa Tyr Xaa Ser Asn Cys
1 5 10

<210> SEQ ID NO 298
<211> LENGTH: 10
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 298

Tyr Tyr Asp Leu Arg Xaa Arg Xaa Gly Cys
1 5 10

<210> SEQ ID NO 299
<211> LENGTH: 12
<212> TYPE: PRT
<213> ORGANISM: Artificial Sequence
<220> FEATURE:
<223> OTHER INFORMATION: Peptide obtained from IFNGR1 binder selection
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 299

Tyr Tyr Asn Leu Arg Xaa Ala Xaa Asn Thr Asn Cys
1 5 10

<210> SEQ ID NO 300
<211> LENGTH: 63
<212> TYPE: RNA
<213> ORGANISM: Artificial Sequence
<220> FEATURE:
<223> OTHER INFORMATION: mRNA (mR1) for gammma-cyclic amino acid

<400> SEQUENCE: 300
auguacaaga aguacaaaaa guacaaagcu ccgggugacu acaaggacga cgacgacaag 60
uaa 63

<210> SEQ ID NO 301
<211> LENGTH: 20
<212> TYPE: PRT
<213> ORGANISM: Artificial Sequence
<220> FEATURE:
<223> OTHER INFORMATION: reprogrammed peptide rP1 for gammma-cyclic amino acid
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (11)..(11)
<223> OTHER INFORMATION: gamma-cyclic amino acid

<400> SEQUENCE: 301

Met Tyr Lys Lys Tyr Lys Lys Tyr Lys Phe Xaa Gly Asp Tyr Lys Asp
1 5 10 15

Asp Asp Asp Lys
20

<210> SEQ ID NO 302
<211> LENGTH: 38
<212> TYPE: DNA
<213> ORGANISM: Artificial Sequence
<220> FEATURE:
<223> OTHER INFORMATION: primer (NNUAUG-GT3.R38)

<400> SEQUENCE: 302
tttccgcccc ccgtcctagg tccccgtacc cgtgccca 38

<210> SEQ ID NO 303
<211> LENGTH: 52
<212> TYPE: DNA
<213> ORGANISM: Artificial Sequence
<220> FEATURE:
<223> OTHER INFORMATION: primer (T7.F52)

<400> SEQUENCE: 303
ggcgtaatac gactcactat agggttgaac tttaagtagg agatatatcc at 52

<210> SEQ ID NO 304
<211> LENGTH: 77
<212> TYPE: RNA
<213> ORGANISM: Artificial Sequence
<220> FEATURE:
<223> OTHER INFORMATION: tRNA, Pro1E2(GAA)

<400> SEQUENCE: 304
gggugauugg cgcagccugg uagcgcacuu cgcugaaaac gaagggguca gggguucgaa 60
uccccuauca cccgcca 77

<210> SEQ ID NO 305
<211> LENGTH: 77
<212> TYPE: RNA
<213> ORGANISM: Artificial Sequence
<220> FEATURE:
<223> OTHER INFORMATION: tRNA, Pro1E2(GAG)

<400> SEQUENCE: 305
gggugauugg cgcagccugg uagcgcacuu cguugagguc gaagggguca gggguucgaa 60
uccccuauca cccgcca 77

<210> SEQ ID NO 306
<211> LENGTH: 77
<212> TYPE: RNA
<213> ORGANISM: Artificial Sequence
<220> FEATURE:
<223> OTHER INFORMATION: tRNA, Pro1E2(GGU)

<400> SEQUENCE: 306
gggugauugg cgcagccugg uagcgcacuu cguugguaac gaagggguca gggguucgaa 60
uccccuauca cccgcca 77

<210> SEQ ID NO 307
<211> LENGTH: 76
<212> TYPE: RNA
<213> ORGANISM: Artificial Sequence
<220> FEATURE:
<223> OTHER INFORMATION: tRNA, GluE2(CGG)

<400> SEQUENCE: 307
guccccuucg ucuagaggcc caggacaccg ccuucgggag gcgguaacag ggguucgaau 60
ccccuagggg acgcca 76

<210> SEQ ID NO 308
<211> LENGTH: 50
<212> TYPE: DNA
<213> ORGANISM: Artificial Sequence
<220> FEATURE:
<223> OTHER INFORMATION: Extension primer (forward) for tRNA,
Pro1E2(GAA)

<400> SEQUENCE: 308
gtaatacgac tcactatagg gtgattggcg cagcctggta gcgcacttcg 50

<210> SEQ ID NO 309
<211> LENGTH: 50
<212> TYPE: DNA
<213> ORGANISM: Artificial Sequence
<220> FEATURE:
<223> OTHER INFORMATION: Extension primer (forward) for tRNA,
Pro1E2(GAG)

<400> SEQUENCE: 309
gtaatacgac tcactatagg gtgattggcg cagcctggta gcgcacttcg 50

<210> SEQ ID NO 310
<211> LENGTH: 50
<212> TYPE: DNA

<213> ORGANISM: Artificial Sequence
<220> FEATURE:
<223> OTHER INFORMATION: Extension primer (forward) for tRNA,
Pro1E2(GGU)

<400> SEQUENCE: 310
gtaatacgac tcactatagg gtgattggcg cagcctggta gcgcacttcg 50

<210> SEQ ID NO 311
<211> LENGTH: 64
<212> TYPE: DNA
<213> ORGANISM: Artificial Sequence
<220> FEATURE:
<223> OTHER INFORMATION: Extension primer (forward) for tRNA, GluE2(CGG)

<400> SEQUENCE: 311
cactatagtc cccttcgtct agaggcccag gacaccgcct tcgggaggcg gtaacagggg 60
ttcg 64

<210> SEQ ID NO 312
<211> LENGTH: 62
<212> TYPE: DNA
<213> ORGANISM: Artificial Sequence
<220> FEATURE:
<223> OTHER INFORMATION: Extension primer (reverse) for tRNA,
Pro1E2(GAA)

<400> SEQUENCE: 312
tggcgggtga taggggattc gaacccctga ccccttcgtt ttcagcgaag tgcgctacca 60
gg 62

<210> SEQ ID NO 313
<211> LENGTH: 62
<212> TYPE: DNA
<213> ORGANISM: Artificial Sequence
<220> FEATURE:
<223> OTHER INFORMATION: Extension primer (reverse) for tRNA,
Pro1E2(GAG)

<400> SEQUENCE: 313
tggcgggtga taggggattc gaacccctga ccccttcgac ctcaacgaag tgcgctacca 60
gg 62

<210> SEQ ID NO 314
<211> LENGTH: 62
<212> TYPE: DNA
<213> ORGANISM: Artificial Sequence
<220> FEATURE:
<223> OTHER INFORMATION: Extension primer (reverse) for tRNA,
Pro1E2(GGU)

<400> SEQUENCE: 314
tggcgggtga tagaggattc gaacctccga ccccttcgtt accaacgaag tgcgctacca 60
gg 62

<210> SEQ ID NO 315
<211> LENGTH: 37
<212> TYPE: DNA
<213> ORGANISM: Artificial Sequence
<220> FEATURE:
<223> OTHER INFORMATION: Extension primer (reverse) for tRNA, GluE2(CGG)

<400> SEQUENCE: 315
tggcgtcccc taggggattc gaacccctgt taccgcc 37

<210> SEQ ID NO 316
<211> LENGTH: 22
<212> TYPE: DNA
<213> ORGANISM: Artificial Sequence
<220> FEATURE:
<223> OTHER INFORMATION: PCR primer (forward) for tRNA, Pro1E2(GAA)

<400> SEQUENCE: 316
ggcgtaatac gactcactat ag 22

<210> SEQ ID NO 317
<211> LENGTH: 22
<212> TYPE: DNA
<213> ORGANISM: Artificial Sequence
<220> FEATURE:
<223> OTHER INFORMATION: PCR primer (forward) for tRNA, Pro1E2(GAG)

<400> SEQUENCE: 317
ggcgtaatac gactcactat ag 22

<210> SEQ ID NO 318
<211> LENGTH: 22
<212> TYPE: DNA
<213> ORGANISM: Artificial Sequence
<220> FEATURE:
<223> OTHER INFORMATION: PCR primer (forward) for tRNA, Pro1E2(GGU)

<400> SEQUENCE: 318
ggcgtaatac gactcactat ag 22

<210> SEQ ID NO 319
<211> LENGTH: 33
<212> TYPE: DNA
<213> ORGANISM: Artificial Sequence
<220> FEATURE:
<223> OTHER INFORMATION: PCR primer (forward) for tRNA, GluE2(CGG)

<400> SEQUENCE: 319
gtaatacgac tcactatagt ccccttcgtc tag 33

<210> SEQ ID NO 320
<211> LENGTH: 20
<212> TYPE: DNA
<213> ORGANISM: Artificial Sequence
<220> FEATURE:
<223> OTHER INFORMATION: PCR primer (reverse) for tRNA, Pro1E2(GAA)
<220> FEATURE:
<221> NAME/KEY: misc_feature
<222> LOCATION: (2)..(2)
<223> OTHER INFORMATION: gm

<400> SEQUENCE: 320
tggcgggtga taggggattc 20

<210> SEQ ID NO 321
<211> LENGTH: 20
<212> TYPE: DNA
<213> ORGANISM: Artificial Sequence
<220> FEATURE:
<223> OTHER INFORMATION: PCR primer (reverse) for tRNA, Pro1E2(GAG)
<220> FEATURE:
<221> NAME/KEY: misc_feature
<222> LOCATION: (2)..(2)
<223> OTHER INFORMATION: gm

<400> SEQUENCE: 321
tggcgggtga taggggattc 20

<210> SEQ ID NO 322
<211> LENGTH: 20
<212> TYPE: DNA
<213> ORGANISM: Artificial Sequence
<220> FEATURE:
<223> OTHER INFORMATION: PCR primer (reverse) for tRNA, Pro1E2(GGU)
<220> FEATURE:
<221> NAME/KEY: misc_feature
<222> LOCATION: (2)..(2)
<223> OTHER INFORMATION: gm

<400> SEQUENCE: 322
tggcgggtga taggggattc 20

<210> SEQ ID NO 323
<211> LENGTH: 20
<212> TYPE: DNA
<213> ORGANISM: Artificial Sequence
<220> FEATURE:
<223> OTHER INFORMATION: PCR primer (reverse) for tRNA, GluE2(CGG)
<220> FEATURE:
<221> NAME/KEY: misc_feature
<222> LOCATION: (2)..(2)
<223> OTHER INFORMATION: gm

<400> SEQUENCE: 323
tggcgtcccc taggggattc 20

<210> SEQ ID NO 324
<211> LENGTH: 63
<212> TYPE: RNA
<213> ORGANISM: Artificial Sequence
<220> FEATURE:
<223> OTHER INFORMATION: mRNA (mR1)

<400> SEQUENCE: 324
auguacaaga aguacaaaaa guacaaauuc ccgggugacu acaaggacga cgacgacaag 60
uaa 63

<210> SEQ ID NO 325
<211> LENGTH: 66
<212> TYPE: RNA
<213> ORGANISM: Artificial Sequence
<220> FEATURE:
<223> OTHER INFORMATION: mRNA (mR2)

<400> SEQUENCE: 325
auguacaaga aguacaaaaa guacaaauuc ccgccgggug acuacaagga cgacgacgac 60
aaguaa 66

<210> SEQ ID NO 326
<211> LENGTH: 69
<212> TYPE: RNA
<213> ORGANISM: Artificial Sequence
<220> FEATURE:
<223> OTHER INFORMATION: mRNA (mR3)

<400> SEQUENCE: 326
auguacaaga aguacaaaaa guacaaauuc ccguucccgg gugacuacaa ggacgacgac 60
gacaaguaa 69

<210> SEQ ID NO 327
<211> LENGTH: 72
<212> TYPE: RNA
<213> ORGANISM: Artificial Sequence
<220> FEATURE:
<223> OTHER INFORMATION: mRNA (mR4)

<400> SEQUENCE: 327
auguacaaga aguacaaaaa guacaaauuc ccguucuucc cgggugacua caaggacgac 60
gacgacaagu aa 72

<210> SEQ ID NO 328
<211> LENGTH: 60
<212> TYPE: RNA
<213> ORGANISM: Artificial Sequence
<220> FEATURE:
<223> OTHER INFORMATION: mRNA (mR5)

<400> SEQUENCE: 328
augucucauc cuacucguaa uuuugcuggu auggacuaca aggacgacga cgacaaguaa 60

<210> SEQ ID NO 329
<211> LENGTH: 60
<212> TYPE: RNA
<213> ORGANISM: Artificial Sequence
<220> FEATURE:
<223> OTHER INFORMATION: mRNA (mR6)

<400> SEQUENCE: 329
augucucauc cuacucguaa ucuugcuggu auggacuaca aggacgacga cgacaaguaa 60

<210> SEQ ID NO 330
<211> LENGTH: 60
<212> TYPE: RNA
<213> ORGANISM: Artificial Sequence
<220> FEATURE:
<223> OTHER INFORMATION: mRNA (mR7)

<400> SEQUENCE: 330
augucucauc cuacucguaa uauugcuggu auggacuaca aggacgacga cgacaaguaa 60

<210> SEQ ID NO 331
<211> LENGTH: 66
<212> TYPE: RNA
<213> ORGANISM: Artificial Sequence
<220> FEATURE:
<223> OTHER INFORMATION: mRNA (mR8)

<400> SEQUENCE: 331
augaagauuu acccguacua cacuuaccau aagaagaagg acuacaagga cgacgacgac 60
aaguaa 66

<210> SEQ ID NO 332
<211> LENGTH: 75
<212> TYPE: RNA
<213> ORGANISM: Artificial Sequence
<220> FEATURE:
<223> OTHER INFORMATION: mRNA (mR9)

<400> SEQUENCE: 332
auguacaaga aauacaaaaa guacaaguuc ccguucuucc cggguaugga cuacaaggac 60
gacgacgaca aguaa 75

-continued

<210> SEQ ID NO 333
<211> LENGTH: 72
<212> TYPE: RNA
<213> ORGANISM: Artificial Sequence
<220> FEATURE:
<223> OTHER INFORMATION: mRNA (mR10)

<400> SEQUENCE: 333
augaaguaca uuaaggguua cacuuacggc uacccguaca ugaaggacua caaggacgac 60
gacgacaagu aa 72

<210> SEQ ID NO 334
<211> LENGTH: 20
<212> TYPE: PRT
<213> ORGANISM: Artificial Sequence
<220> FEATURE:
<223> OTHER INFORMATION: reprogrammed peptide rP1
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (11)..(11)
<223> OTHER INFORMATION: Abz derivatives

<400> SEQUENCE: 334

Met Tyr Lys Lys Tyr Lys Lys Tyr Lys Phe Xaa Gly Asp Tyr Lys Asp
1 5 10 15

Asp Asp Asp Lys
20

<210> SEQ ID NO 335
<211> LENGTH: 21
<212> TYPE: PRT
<213> ORGANISM: Artificial Sequence
<220> FEATURE:
<223> OTHER INFORMATION: reprogrammed peptide rP2
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (11)..(12)
<223> OTHER INFORMATION: Abz

<400> SEQUENCE: 335

Met Tyr Lys Lys Tyr Lys Lys Tyr Lys Phe Xaa Xaa Gly Asp Tyr Lys
1 5 10 15

Asp Asp Asp Asp Lys
20

<210> SEQ ID NO 336
<211> LENGTH: 22
<212> TYPE: PRT
<213> ORGANISM: Artificial Sequence
<220> FEATURE:
<223> OTHER INFORMATION: reprogrammed peptide rP3
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (11)..(11)
<223> OTHER INFORMATION: Abz
<220> FEATURE:
<221> NAME/KEY: MISC_FEATURE
<222> LOCATION: (13)..(13)

-continued

<223> OTHER INFORMATION: Abz

<400> SEQUENCE: 336

```
Met Tyr Lys Lys Tyr Lys Lys Tyr Lys Phe Xaa Phe Xaa Gly Asp Tyr
1               5                   10                  15

Lys Asp Asp Asp Asp Lys
            20
```

<210> SEQ ID NO 337
<211> LENGTH: 23
<212> TYPE: PRT
<213> ORGANISM: Artificial Sequence
<220> FEATURE:
<223> OTHER INFORMATION: reprogrammed peptide rP4
<220> FEATURE:
<221> NAME/KEY: MISC_FEATURE
<222> LOCATION: (1)..(1)
<223> OTHER INFORMATION: N-Formylmethionine
<220> FEATURE:
<221> NAME/KEY: MISC_FEATURE
<222> LOCATION: (11)..(11)
<223> OTHER INFORMATION: Abz
<220> FEATURE:
<221> NAME/KEY: MISC_FEATURE
<222> LOCATION: (14)..(14)
<223> OTHER INFORMATION: Abz

<400> SEQUENCE: 337

```
Met Tyr Lys Lys Tyr Lys Lys Tyr Lys Phe Xaa Phe Phe Xaa Gly Asp
1               5                   10                  15

Tyr Lys Asp Asp Asp Asp Lys
            20
```

<210> SEQ ID NO 338
<211> LENGTH: 19
<212> TYPE: PRT
<213> ORGANISM: Artificial Sequence
<220> FEATURE:
<223> OTHER INFORMATION: reprogrammed peptide rP5
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: Abz

<400> SEQUENCE: 338

```
Tyr Ser His Pro Thr Asp Asn Xaa Ala Gly Cys Asp Tyr Lys Asp Asp
1               5                   10                  15

Asp Asp Lys
```

<210> SEQ ID NO 339
<211> LENGTH: 19
<212> TYPE: PRT
<213> ORGANISM: Artificial Sequence
<220> FEATURE:
<223> OTHER INFORMATION: reprogrammed peptide rP6
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: Atp

<400> SEQUENCE: 339

Tyr Ser His Pro Thr Asp Asn Xaa Ala Gly Cys Asp Tyr Lys Asp Asp
1 5 10 15

Asp Asp Lys

<210> SEQ ID NO 340
<211> LENGTH: 19
<212> TYPE: PRT
<213> ORGANISM: Artificial Sequence
<220> FEATURE:
<223> OTHER INFORMATION: reprogrammed peptide rP7
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: Apy

<400> SEQUENCE: 340

Tyr Ser His Pro Thr Asp Asn Xaa Ala Gly Cys Asp Tyr Lys Asp Asp
1 5 10 15

Asp Asp Lys

<210> SEQ ID NO 341
<211> LENGTH: 21
<212> TYPE: PRT
<213> ORGANISM: Artificial Sequence
<220> FEATURE:
<223> OTHER INFORMATION: reprogrammed peptide rP8
<220> FEATURE:
<221> NAME/KEY: MISC_FEATURE
<222> LOCATION: (3)..(3)
<223> OTHER INFORMATION: MeSer
<220> FEATURE:
<221> NAME/KEY: MISC_FEATURE
<222> LOCATION: (5)..(5)
<223> OTHER INFORMATION: (1S,2S)-2-ACPC
<220> FEATURE:
<221> NAME/KEY: MISC_FEATURE
<222> LOCATION: (8)..(8)
<223> OTHER INFORMATION: Abz or Abz5OMe

<400> SEQUENCE: 341

Phe Lys Xaa Tyr Xaa Tyr Tyr Xaa Tyr Cys Lys Lys Lys Asp Tyr Lys
1 5 10 15

Asp Asp Asp Asp Lys
20

<210> SEQ ID NO 342
<211> LENGTH: 24
<212> TYPE: PRT
<213> ORGANISM: Artificial Sequence
<220> FEATURE:
<223> OTHER INFORMATION: reprogrammed peptide rP9
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (11)..(11)
<223> OTHER INFORMATION: Abz
<220> FEATURE:
<221> NAME/KEY: MISC_FEATURE
<222> LOCATION: (14)..(14)
<223> OTHER INFORMATION: Abz

<400> SEQUENCE: 342

Tyr Tyr Lys Lys Tyr Lys Lys Tyr Lys Phe Xaa Phe Phe Xaa Gly Cys
1 5 10 15

Asp Tyr Lys Asp Asp Asp Asp Lys
20

<210> SEQ ID NO 343
<211> LENGTH: 23
<212> TYPE: PRT
<213> ORGANISM: Artificial Sequence
<220> FEATURE:
<223> OTHER INFORMATION: reprogrammed peptide rP10
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (4)..(4)
<223> OTHER INFORMATION: (1S,2S)-2-ACPC
<220> FEATURE:
<221> NAME/KEY: MISC_FEATURE
<222> LOCATION: (8)..(8)
<223> OTHER INFORMATION: Apy
<220> FEATURE:
<221> NAME/KEY: MISC_FEATURE
<222> LOCATION: (12)..(12)
<223> OTHER INFORMATION: Abz

<400> SEQUENCE: 343

Tyr Lys Tyr Xaa Lys Gly Tyr Xaa Tyr Gly Tyr Xaa Tyr Cys Lys Asp
1 5 10 15

Tyr Lys Asp Asp Asp Asp Lys
20

<210> SEQ ID NO 344
<211> LENGTH: 24
<212> TYPE: RNA
<213> ORGANISM: Artificial Sequence
<220> FEATURE:
<223> OTHER INFORMATION: flag in mR1

<400> SEQUENCE: 344
gacuacaagg acgacgacga caag 24

<210> SEQ ID NO 345
<211> LENGTH: 8
<212> TYPE: PRT
<213> ORGANISM: Artificial Sequence
<220> FEATURE:
<223> OTHER INFORMATION: flag in rP1

<400> SEQUENCE: 345

Asp Tyr Lys Asp Asp Asp Asp Lys
1 5

<210> SEQ ID NO 346
<211> LENGTH: 116
<212> TYPE: RNA
<213> ORGANISM: Artificial Sequence
<220> FEATURE:
<223> OTHER INFORMATION: mRNA in peptide library
<220> FEATURE:
<221> NAME/KEY: misc_feature
<222> LOCATION: (33)..(34)
<223> OTHER INFORMATION: n is a, c, g, or u
<220> FEATURE:
<221> NAME/KEY: misc_feature
<222> LOCATION: (36)..(37)

<223> OTHER INFORMATION: n is a, c, g, or u
<220> FEATURE:
<221> NAME/KEY: misc_feature
<222> LOCATION: (39)..(40)
<223> OTHER INFORMATION: n is a, c, g, or u
<220> FEATURE:
<221> NAME/KEY: misc_feature
<222> LOCATION: (42)..(43)
<223> OTHER INFORMATION: n is a, c, g, or u
<220> FEATURE:
<221> NAME/KEY: misc_feature
<222> LOCATION: (45)..(46)
<223> OTHER INFORMATION: n is a, c, g, or u
<220> FEATURE:
<221> NAME/KEY: misc_feature
<222> LOCATION: (48)..(49)
<223> OTHER INFORMATION: n is a, c, g, or u
<220> FEATURE:
<221> NAME/KEY: mutation
<222> LOCATION: (51)..(77)
<223> OTHER INFORMATION: any NNUs can be deleted
<220> FEATURE:
<221> NAME/KEY: misc_feature
<222> LOCATION: (51)..(52)
<223> OTHER INFORMATION: n is a, c, g, or u
<220> FEATURE:
<221> NAME/KEY: misc_feature
<222> LOCATION: (54)..(55)
<223> OTHER INFORMATION: n is a, c, g, or u
<220> FEATURE:
<221> NAME/KEY: misc_feature
<222> LOCATION: (57)..(58)
<223> OTHER INFORMATION: n is a, c, g, or u
<220> FEATURE:
<221> NAME/KEY: misc_feature
<222> LOCATION: (60)..(61)
<223> OTHER INFORMATION: n is a, c, g, or u
<220> FEATURE:
<221> NAME/KEY: misc_feature
<222> LOCATION: (63)..(64)
<223> OTHER INFORMATION: n is a, c, g, or u
<220> FEATURE:
<221> NAME/KEY: misc_feature
<222> LOCATION: (66)..(67)
<223> OTHER INFORMATION: n is a, c, g, or u
<220> FEATURE:
<221> NAME/KEY: misc_feature
<222> LOCATION: (69)..(70)
<223> OTHER INFORMATION: n is a, c, g, or u
<220> FEATURE:
<221> NAME/KEY: misc_feature
<222> LOCATION: (72)..(73)
<223> OTHER INFORMATION: n is a, c, g, or u
<220> FEATURE:
<221> NAME/KEY: misc_feature
<222> LOCATION: (75)..(76)
<223> OTHER INFORMATION: n is a, c, g, or u

<400> SEQUENCE: 346
ggguugaacu uuaaguagga gauauaucca ugnnunnunn unnunnunnu nnunnunnun 60
nunnunnunn unnunnuaug ggcacgggua cggggaccua ggacgggggg cggaaa 116

<210> SEQ ID NO 347
<211> LENGTH: 23
<212> TYPE: PRT
<213> ORGANISM: Artificial Sequence
<220> FEATURE:
<223> OTHER INFORMATION: peptide in peptide library
<220> FEATURE:
<221> NAME/KEY: MISC_FEATURE
<222> LOCATION: (1)..(1)
<223> OTHER INFORMATION: N-Chloroacetyl D-tyrosine
<220> FEATURE:
<221> NAME/KEY: MISC_FEATURE
<222> LOCATION: (2)..(16)

-continued

<223> OTHER INFORMATION: each X can be independently Phe, Ser, Tyr Leu, Pro, Arg, Thr, Asn, Val, Ala, Asp, Gly, (1S, 2S)-2-ACHC, (1R, 2R)-2-ACPC, or (1S, 2S)-2-ACPC
<220> FEATURE:
<221> NAME/KEY: MISC_FEATURE
<222> LOCATION: (8)..(16)
<223> OTHER INFORMATION: any X can be deleted

<400> SEQUENCE: 347

```
Tyr Xaa Xaa Xaa Xaa Xaa Xaa Xaa Xaa Xaa Xaa Xaa Xaa Xaa Xaa Xaa
1               5                   10                  15

Cys Gly Thr Gly Thr Gly Thr
            20
```

<210> SEQ ID NO 348
<211> LENGTH: 14
<212> TYPE: PRT
<213> ORGANISM: Artificial Sequence
<220> FEATURE:
<223> OTHER INFORMATION: F1 in Table 11
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1R,2R)-2-ACPC

<400> SEQUENCE: 348

```
Tyr Asn Asp Arg Ser Thr Arg Xaa Arg Leu Val Ala Cys Gly
1               5                   10
```

<210> SEQ ID NO 349
<211> LENGTH: 14
<212> TYPE: PRT
<213> ORGANISM: Artificial Sequence
<220> FEATURE:
<223> OTHER INFORMATION: F1A in Table 11
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 349

```
Tyr Asn Asp Arg Ser Thr Arg Ala Arg Leu Val Ala Cys Gly
1               5                   10
```

<210> SEQ ID NO 350
<211> LENGTH: 14
<212> TYPE: PRT
<213> ORGANISM: Artificial Sequence
<220> FEATURE:
<223> OTHER INFORMATION: F2 in Table 11
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1S,2S)-2-ACHC

<400> SEQUENCE: 350

```
Tyr Pro Arg Leu Phe Asn Xaa Ser Tyr Leu Arg Arg Cys Gly
1               5                   10
```

<210> SEQ ID NO 351
<211> LENGTH: 14
<212> TYPE: PRT

<213> ORGANISM: Artificial Sequence
<220> FEATURE:
<223> OTHER INFORMATION: F2A in Table 11
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 351

Tyr Pro Arg Leu Phe Asn Ala Ser Tyr Leu Arg Arg Cys Gly
1 5 10

<210> SEQ ID NO 352
<211> LENGTH: 18
<212> TYPE: PRT
<213> ORGANISM: Artificial Sequence
<220> FEATURE:
<223> OTHER INFORMATION: F3 in Table 11
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (8)..(8)
<223> OTHER INFORMATION: (1S,2S)-2-ACHC
<220> FEATURE:
<221> NAME/KEY: MISC_FEATURE
<222> LOCATION: (13)..(13)
<223> OTHER INFORMATION: (1S,2S)-2-ACHC

<400> SEQUENCE: 352

Tyr Phe Ala Tyr Asp Arg Arg Xaa Leu Ser Asn Asn Xaa Arg Asn Tyr
1 5 10 15

Cys Gly

<210> SEQ ID NO 353
<211> LENGTH: 18
<212> TYPE: PRT
<213> ORGANISM: Artificial Sequence
<220> FEATURE:
<223> OTHER INFORMATION: F3A in Table 11
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 353

Tyr Phe Ala Tyr Asp Arg Arg Ala Leu Ser Asn Asn Ala Arg Asn Tyr
1 5 10 15

Cys Gly

<210> SEQ ID NO 354
<211> LENGTH: 14
<212> TYPE: PRT
<213> ORGANISM: Artificial Sequence
<220> FEATURE:
<223> OTHER INFORMATION: F4 in Table 11
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACHC
<220> FEATURE:
<221> NAME/KEY: MISC_FEATURE
<222> LOCATION: (10)..(10)
<223> OTHER INFORMATION: (1S,2S)-2-ACHC -continued

<400> SEQUENCE: 354

Tyr Arg Tyr Thr Xaa Asn Arg Leu Phe Xaa Asn Ala Cys Gly
1 5 10

<210> SEQ ID NO 355
<211> LENGTH: 14
<212> TYPE: PRT
<213> ORGANISM: Artificial Sequence
<220> FEATURE:
<223> OTHER INFORMATION: F4A in Table 11
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 355

Tyr Arg Tyr Thr Ala Asn Arg Leu Phe Ala Asn Ala Cys Gly
1 5 10

<210> SEQ ID NO 356
<211> LENGTH: 13
<212> TYPE: PRT
<213> ORGANISM: Artificial Sequence
<220> FEATURE:
<223> OTHER INFORMATION: I1-1 in Table 12
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 356

Tyr Phe Gly Val Arg Xaa Phe Tyr Asn Arg Thr Cys Gly
1 5 10

<210> SEQ ID NO 357
<211> LENGTH: 13
<212> TYPE: PRT
<213> ORGANISM: Artificial Sequence
<220> FEATURE:
<223> OTHER INFORMATION: I1-2 in Table 12
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (2)..(2)
<223> OTHER INFORMATION: (1S,2S)-2-ACHC
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 357

Tyr Xaa Gly Leu Ser Xaa Tyr Val Asn Arg Ser Cys Gly
1 5 10

<210> SEQ ID NO 358
<211> LENGTH: 13
<212> TYPE: PRT
<213> ORGANISM: Artificial Sequence
<220> FEATURE:
<223> OTHER INFORMATION: I1-3 in Table 12
<220> FEATURE:
<221> NAME/KEY: MISC_FEATURE
<222> LOCATION: (1)..(1)
<223> OTHER INFORMATION: N-Chloroacetyl tyrosine

```
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 358

Tyr Val Gly Leu Asn Xaa Ser Leu Asn Arg Thr Cys Gly
1               5                   10


<210> SEQ ID NO 359
<211> LENGTH: 15
<212> TYPE: PRT
<213> ORGANISM: Artificial Sequence
<220> FEATURE:
<223> OTHER INFORMATION: I1-4 in Table 12
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC

<400> SEQUENCE: 359

Tyr Phe Ser Leu Arg Xaa Ser Phe Asn Arg Ser Arg Gly Cys Gly
1               5                   10                  15


<210> SEQ ID NO 360
<211> LENGTH: 13
<212> TYPE: PRT
<213> ORGANISM: Artificial Sequence
<220> FEATURE:
<223> OTHER INFORMATION: I1-5 in Table 12
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (6)..(6)
<223> OTHER INFORMATION: (1R,2R)-2-ACPC
<220> FEATURE:
<221> NAME/KEY: MISC_FEATURE
<222> LOCATION: (8)..(8)
<223> OTHER INFORMATION: (1S,2S)-2-ACHC

<400> SEQUENCE: 360

Tyr Phe Ala Leu Asn Xaa Arg Xaa Asn Arg Arg Cys Gly
1               5                   10


<210> SEQ ID NO 361
<211> LENGTH: 13
<212> TYPE: PRT
<213> ORGANISM: Artificial Sequence
<220> FEATURE:
<223> OTHER INFORMATION: I1-6 in Table 12
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (5)..(5)
<223> OTHER INFORMATION: (1S,2S)-2-ACPC
<220> FEATURE:
<221> NAME/KEY: MISC_FEATURE
<222> LOCATION: (6)..(6)
<223> OTHER INFORMATION: (1R,2R)-2-ACPC
```

<400> SEQUENCE: 361

Tyr Phe Gly Val Xaa Xaa Phe Tyr Asn Arg Thr Cys Gly
1 5 10

<210> SEQ ID NO 362
<211> LENGTH: 13
<212> TYPE: PRT
<213> ORGANISM: Artificial Sequence
<220> FEATURE:
<223> OTHER INFORMATION: I1-1A in Table 12
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 362

Tyr Phe Gly Val Arg Ala Phe Tyr Asn Arg Thr Cys Gly
1 5 10

<210> SEQ ID NO 363
<211> LENGTH: 17
<212> TYPE: PRT
<213> ORGANISM: Artificial Sequence
<220> FEATURE:
<223> OTHER INFORMATION: I2 in Table 12
<220> FEATURE:
<221> NAME/KEY: MISC_FEATURE
<222> LOCATION: (1)..(1)
<223> OTHER INFORMATION: N-Chloroacetyl tyrosine
<220> FEATURE:
<221> NAME/KEY: MISC_FEATURE
<222> LOCATION: (7)..(7)
<223> OTHER INFORMATION: (1S,2S)-2-ACPC
<220> FEATURE:
<221> NAME/KEY: MISC_FEATURE
<222> LOCATION: (14)..(14)
<223> OTHER INFORMATION: (1R,2R)-2-ACPC

<400> SEQUENCE: 363

Tyr Pro Arg Tyr Asn Leu Xaa Gly Ala Ser Pro Arg Phe Xaa Asn Cys
1 5 10 15

Gly

<210> SEQ ID NO 364
<211> LENGTH: 17
<212> TYPE: PRT
<213> ORGANISM: Artificial Sequence
<220> FEATURE:
<223> OTHER INFORMATION: I2A in Table 12
<220> FEATURE:
<221> NAME/KEY: MISC_FEATURE
<222> LOCATION: (1)..(1)
<223> OTHER INFORMATION: N-Chloroacetyl tyrosine

<400> SEQUENCE: 364

Tyr Pro Arg Tyr Asn Leu Ala Gly Ala Ser Pro Arg Phe Ala Asn Cys
1 5 10 15

Gly

<210> SEQ ID NO 365
<211> LENGTH: 22
<212> TYPE: RNA
<213> ORGANISM: Artificial Sequence
<220> FEATURE:
<223> OTHER INFORMATION: microhelix RNA -continued

<400> SEQUENCE: 365
ggcucuguuc gcagagccgc ca 22